United States Patent
Ben-David et al.

(10) Patent No.: US 7,805,203 B2
(45) Date of Patent: Sep. 28, 2010

(54) METHOD FOR SURGICALLY IMPLANTING AN ELECTRODE DEVICE

(75) Inventors: Tamir Ben-David, Tel Aviv (IL); Shai Ayal, Jerusalem (IL); Omry Ben-Ezra, Tel Aviv (IL); Ehud Cohen, Ganei Tikva (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 403 days.

(21) Appl. No.: 11/975,646

(22) Filed: Oct. 19, 2007

(65) Prior Publication Data

US 2008/0161894 A1 Jul. 3, 2008

Related U.S. Application Data

(63) Continuation of application No. 11/064,446, filed on Feb. 22, 2005.

(51) Int. Cl.
*A61N 1/05* (2006.01)
(52) U.S. Cl. .................................................. 607/118
(58) Field of Classification Search ................. 607/118
See application file for complete search history.

(56) References Cited

U.S. PATENT DOCUMENTS

| | | | | |
|---|---|---|---|---|
| 6,066,136 | A * | 5/2000 | Geistert | 606/41 |
| 6,516,227 | B1 * | 2/2003 | Meadows et al. | 607/46 |
| 2003/0078643 | A1 * | 4/2003 | Schulman et al. | 607/116 |
| 2003/0236557 | A1 * | 12/2003 | Whitehurst et al. | 607/39 |

OTHER PUBLICATIONS

Akselrod, S. et al., (1981) "Power spectrum analysis of heart rate fluctuation: A quantitative probe of beat-to-beat cardiovascular control," *Science* 213:220-222.

Baratta, R. et al., (1989) "Orderly stimulation of skeletal muscle motor units with tripolar nerve cuff electrode," *IEEE Transactions on Biomedical Engineering* 36(1):836-843.

Billette, J. et al., (1975) "Roles of the AV junction in determining the ventricular response to atrial fibrillation," *Canadian Journal of Physiological Pharmacology* 53(4):575-585.

Borovikova, L. et al., (May 25, 2000) "Vagus nerve stimulation attenuates the systemic inflammatory response to endotoxin," *Nature* 405:458-462.

(Continued)

*Primary Examiner*—Michael Kahelin
(74) *Attorney, Agent, or Firm*—John P. White; Cooper & Dunham LLP

(57) ABSTRACT

A method is provided that includes surgically implanting an electrode device having a cuff and one or more electrodes mounted in the cuff, by placing the electrode device around a nerve such that the electrodes face the nerve. Conductive solution is introduced into the electrode device such that the solution is in contact with both the electrodes and the nerve. During implantation of the electrode device, an impedance is measured between one or more of the electrodes and an electrical contact point in electrical communication with the electrode device. Responsively to the impedance measurement, it is determined whether the electrode device is correctly sized for the nerve, and, if not, the electrode device is removed and another electrode device having a different size is implanted. Other embodiments are also described.

10 Claims, 8 Drawing Sheets

OTHER PUBLICATIONS

Chen, S. et al., (1998) "Intracardiac stimulation of human parasympathetic nerve fibers induces negative dromotropic effects: implication with the lesions of radiofrequency catheter ablation," *Journal of Cardiovascular Electrophysiology* 9(3):245-252.

De Ferrari, G. et al, (1991) "Vagal reflexes and survival during acute myocardial ischemia in conscious dogs with healed myocardial infarction," *American Journal of Physiology* 261(1 Pt 2):H63-H69.

Deurloo, K. et al., (1998) "Transverse tripolar stimulation of peripheral nerve: a modeling study of spatial selectivity," *Medical & Biological Engineering & Computing* 36(1):66-74.

Fitzpatrick, D.M. et al., (1991) "A nerve cuff design for the selective activation and blocking of myelinated nerve fibers," *Annual International Conference of the IEEE Engineering in Medicine and Biology* 13(2):906-907.

Garrigue, S. et al., (1998) "Post-ganglionic vagal stimulation of the atrioventricular node reduces ventricular rate during atrial fibrillation," *PACE* 21(4):356 (Part II).

Goodall, E. et al., (1996) "Position-selective activation of peripheral nerve fibers with a cuff electrode," *IEEE Transactions on Biomedical Engineering* 43(8):851-6.

Grill, W., (1997) "Inversion of the current-distance relationship by transient depolarization," *IEEE Transactions on Biomedical Engineering* 44(1):1-9.

Hayashi, H. et al., (1998) "Different effects of class Ic and III antiarrhythmic drugs on vagotonic atrial fibrillation in the canine heart," *Journal of Cardiovascular Pharmacology* 31:101-107.

Higgins, C. et al., S. , (1973) "Parasympathetic control of the heart," *Pharmacological. Reviews* 25(1):120-155.

Jideus, L,. (2001) "Atrial fibrillation after coronary artery bypass surgery: A study of causes and risk factors," *Acta Universitatis Upsaliensis* pp. 1-56.

Jones, J. et al., (1995) "Heart rate responses to selective stimulation of cardiac vagal C fibres in anaesthetized cats, rats and rabbits", *Journal of Physiology* 489(1):203-214.

Kamath, M. et al., (1992) "Effect of vagal nerve electrostimulation on the power spectrum of heart rate variability in man," PACE vol. 15, *Clinical Electrophysiology* 15:235-243.

Kwan, H. et al., (2001) "Cardiovascular adverse drug reactions during initiation of antiarrhythmic therapy for atrial fibrillation," *Canadian Journal of Hospital Pharmacy* 54(1):10-14.

Li, D. et al., (1999) "Promotion of Atrial Fibrillation by Heart Failure in Dogs: Atrial Remodeling of a Different Sort," *Circulation* 100(1):87-95.

Manfredi, M., (1970) "Differential block of conduction of larger fibers in peripheral nerve by direct current," *Archives Italiennes de Biologie* 108:52-55.

Martin, P. et al., (1983) "Phasic effects of repetitive vagal stimulation on atrial contraction," *Circulation Research* 52(6):657-663.

Morady, F. et al., (1990) "Effects of resting vagal tone on accessory atrioventricular connections," *Circulation* 81(1):86-90.

Mushahwar, V. and Korch, K., (2000) "Muscle recruitment through electrical stimulation of the lumbo-sacral spinal cord," *IEEE Transactions on Rehabilitation Engineering* 8(1):9-22.

Naples, G. et al., (1988) "A spiral nerve cuff electrode for peripheral nerve stimulation," *IEEE Transactions on Biomedical Engineering* 35(11):905-916.

Randall, W. ed., (1977) "Neural Regulation of the Heart", *Oxford University Press*, particularly pp. 100-106.

Rijkhoff, N. et al., (1994) "Acute animal studies on the use of anodal block to reduce urethral resistance in sacral root stimulation," *IEEE Transactions on Rehabilitation Engineering*, 2(2):92-99.

Rijkhoff, N. et al., (1998) "Orderly recruitment of motoneurons in an acute rabbit model," *Proc. of the Annual Conf. of the IEEE Engineering in Medicine and Biology Society* 20(5):2564-2565.

Stramba-Badiale, M. et al, (1991) "Sympathetic-Parasympathetic Interaction and Accentuated Antagonism in Conscious Dogs," *American Journal of Physiology* 260 (2Pt 2):H335-340.

Sweeney, J. et al., (1990) "A asymmetric two electrode cuff for generation of unidirectionally propagated action potentials," *IEEE Transactions on Biomedical Engineering* BME-33(6):541-549.

Sweeney, J. et al., (1986) "A nerve cuff technique for selective excitation of peripheral nerve trunk regions," *IEEE Transactions on Biomedical Engineering*, 37(7):706-715.

Takei, M. et al., (2001) "Vagal stimulation prior to atrial rapid pacing protects the atrium from electrical remodeling in anesthetized dogs," *Japanese Circulation Journal* 65(12):1077-1081.

Tarver, W. et al., (1992) "Clinical experience with a helical bipolar stimulating lead," *Pace* vol. 15, Oct., Part II 1545-1156.

Tsuboi, M. et al., (2000) "Inotropic, chronotropic, and dromotropic effects mediated via parasympathetic ganglia in the dog heart," *American Journal of Physiology Heart Circulation Physiology* 279:H1201-H1207.

Ungar, I. et al., (1986) "Generation of unidirectionally propagating action potentials using a monopolar electrode cuff," *Annals of Biomedical Engineering* 14:437-450.

Van Den Honert, C. et al., (1981) "A technique for collision block of peripheral nerve: Frequency dependence," *MP-12, IEEE Transactions on Biomedical Engineering* 28:373-378.

Van Den Honert, C. et al., (1979) "Generation of unidirectionally propagated action potentials in a peripheral nerve by brief stimuli," *Science* 206:1311-1312.

Vanoli, E. et al., (1991) "Vagal stimulation and prevention of sudden death in conscious dogs with a healed myocardial infarction," *Circulation Research* 68(5):1471-1481.

Veraart, C. et al., (1993) "Selective control of muscle activation with a multipolar nerve cuff electrode," *IEEE Transactions on Biomedical Engineering* 40(7):640-653.

Wallick, D. et al., (2001) "Selective AV nodal vagal stimulation improves hemodynamics during acute atrial fibrillation in dogs," *American Journal of Physiology Heart Circulation Physiology* 281:H1490-H1497.

Wang, H. et al., (2003) "Nicotinic acetylcholine receptor alpha-7 subunit is an essential regulator of inflammation," *Nature* 421:384-388.

Waninger, M. et al., (2000) "Electrophysiological control of ventricular rate during atrial fibrillation," *PACE* 23:1239-1244.

Wijffels, M. et al., (1995) "Atrial fibrillation begets atrial fibrillation," *Circulation* 92:1954-1968.

\* cited by examiner

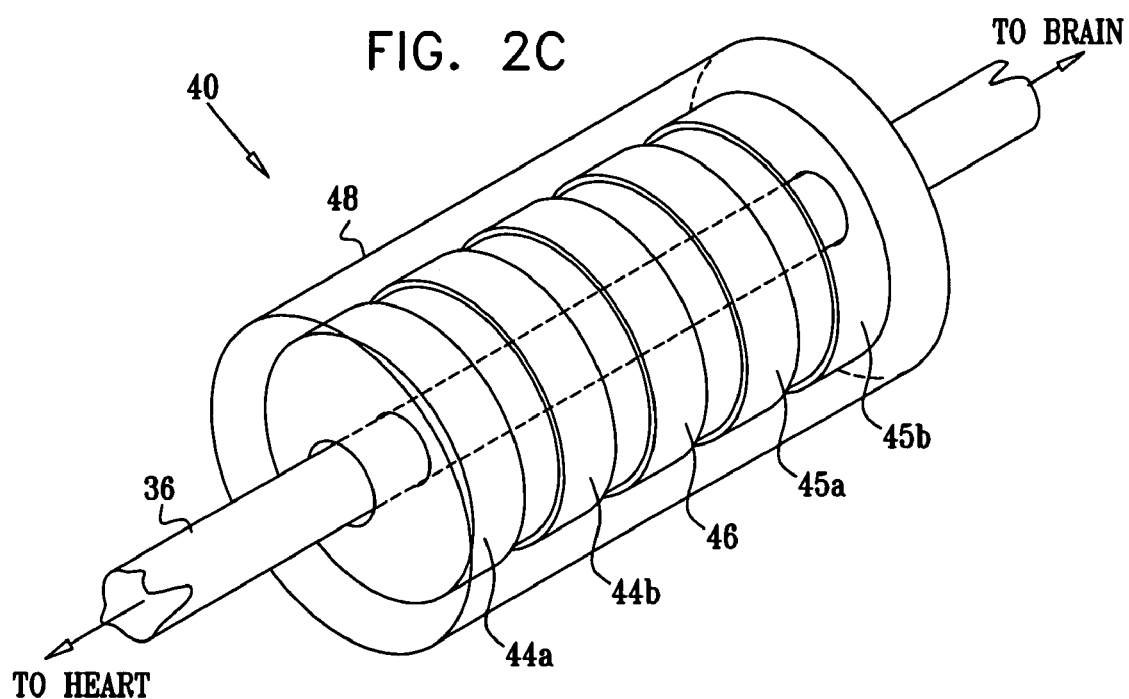

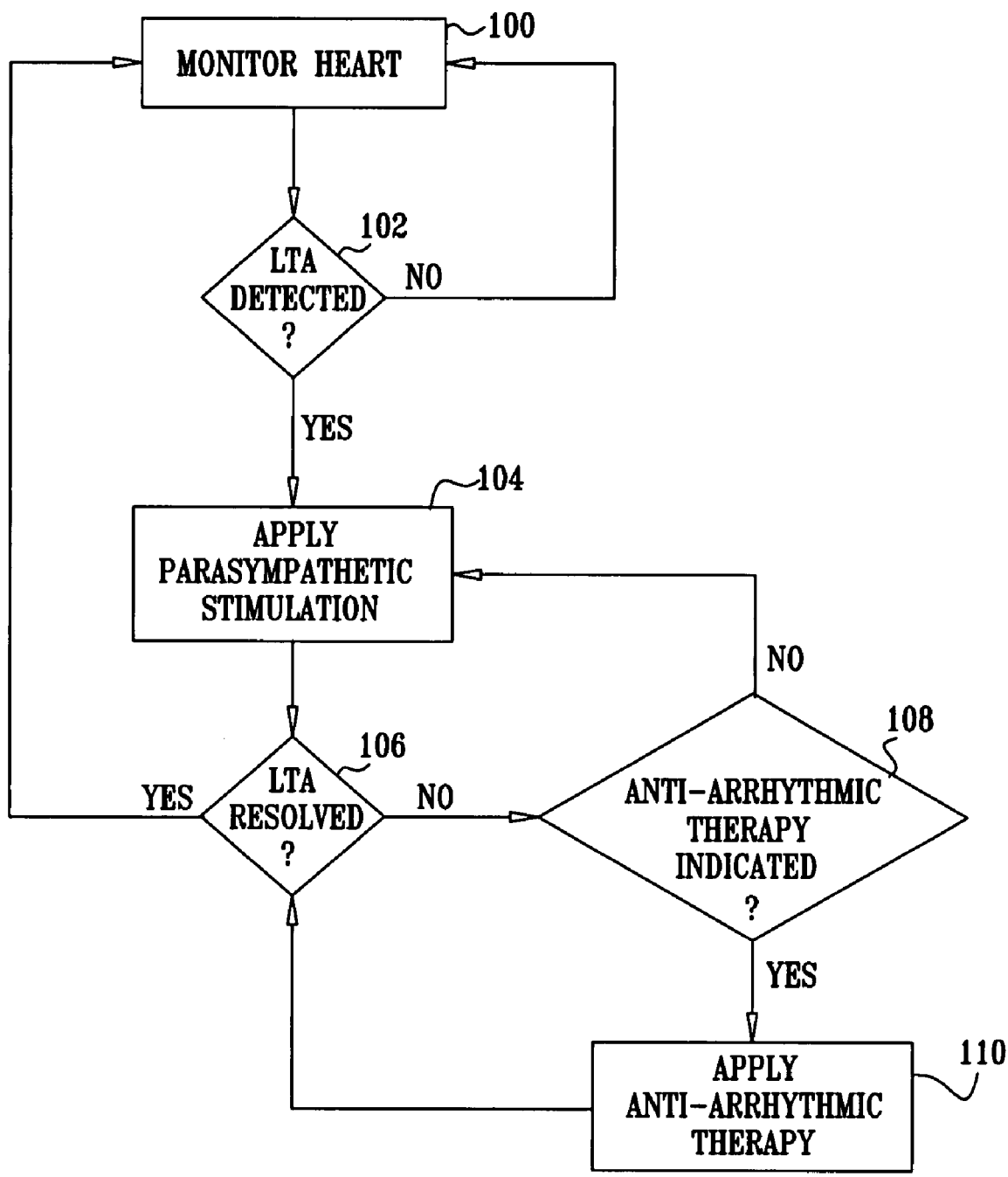

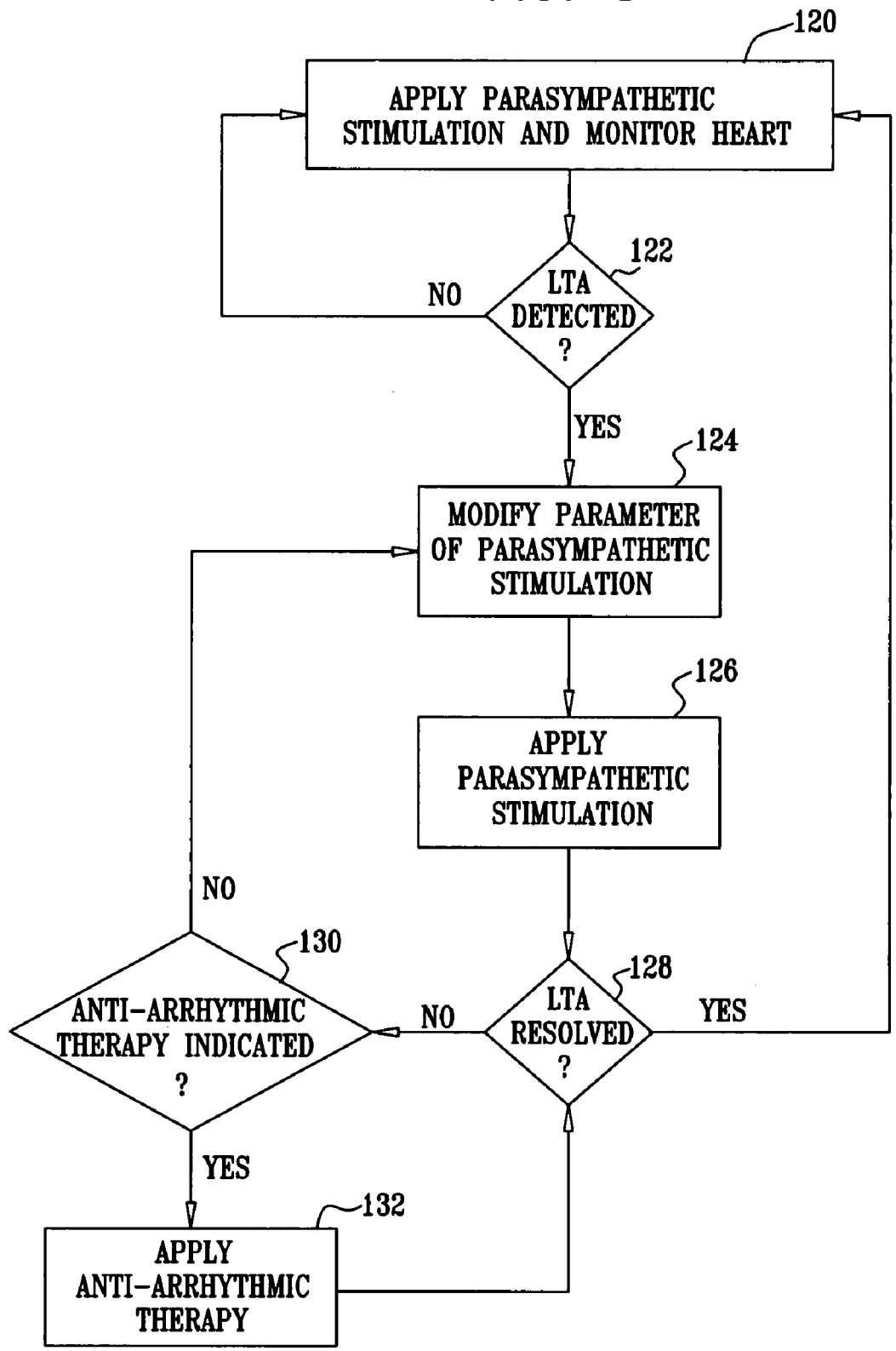

METHOD FOR SURGICALLY IMPLANTING AN ELECTRODE DEVICE

CROSS-REFERENCES TO RELATED APPLICATIONS

This application is a continuation of U.S. Serial No. 11/064,446, filed Feb. 22, 2005, the contents of which are hereby incorperated by reference.

FIELD OF THE INVENTION

The present invention relates generally to treating subjects by application of electrical signals to a selected nerve or nerve bundle, and specifically to methods and apparatus for stimulating the vagus nerve for treating heart conditions.

BACKGROUND OF THE INVENTION

The use of nerve stimulation for treating and controlling a variety of medical, psychiatric, and neurological disorders has seen significant growth over the last several decades. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic activity from the right and left vagus nerves. Low vagal nerve activity is considered to be related to various arrhythmias, including tachycardia, ventricular accelerated rhythm, and rapid atrial fibrillation. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Stimulation of the vagus nerve has been proposed as a method for treating various heart conditions, including heart failure and atrial fibrillation. Heart failure is a cardiac condition characterized by a deficiency in the ability of the heart to pump blood throughout the body and/or to prevent blood from backing up in the lungs. Customary treatment of heart failure includes medication and lifestyle changes. It is often desirable to lower the heart rates of subjects suffering from faster than normal heart rates. The effectiveness of beta blockers in treating heart disease is attributed in part to their heart-rate-lowering effect.

Bilgutay et al., in "Vagal tuning: a new concept in the treatment of supraventricular arrhythmias, angina pectoris, and heart failure," J. Thoracic Cardiovas. Surg. 56(1):71-82, July, 1968, which is incorporated herein by reference, studied the use of a permanently-implanted device with electrodes to stimulate the right vagus nerve for treatment of supraventricular arrhythmias, angina pectoris, and heart failure. Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats. The authors further studied the use of the implanted device in conjunction with the administration of Isuprel, a sympathomimetic drug. They found that Isuprel retained its inotropic effect of increasing contractility, while its chronotropic effect was controlled by the vagal stimulation: "An increased end diastolic volume brought about by slowing of the heart rate by vagal tuning, coupled with increased contractility of the heart induced by the inotropic effect of Isuprel, appeared to increase the efficiency of cardiac performance" (p. 79).

U.S. Pat. No. 6,473,644 to Terry, Jr. et al., which is incorporated herein by reference, describes a method for treating patients suffering from heart failure to increase cardiac output, by stimulating or modulating the vagus nerve with a sequence of substantially equally-spaced pulses by an implanted neurostimulator. The frequency of the stimulating pulses is adjusted until the patient's heart rate reaches a target rate within a relatively stable target rate range below the low end of the patient's customary resting heart rate.

US Patent Application Publication 2003/0040774 to Terry et al., which is incorporated herein by reference, describes a device for treating patients suffering from congestive heart failure. The device includes an implantable neurostimulator for stimulating the patient's vagus nerve at or above the cardiac branch with an electrical pulse waveform at a stimulating rate sufficient to maintain the patient's heart beat at a rate well below the patient's normal resting heart rate, thereby allowing rest and recovery of the heart muscle, to increase in coronary blood flow, and/or growth of coronary capillaries. A metabolic need sensor detects the patient's current physical state and concomitantly supplies a control signal to the neurostimulator to vary the stimulating rate. If the detection indicates a state of rest, the neurostimulator rate reduces the patient's heart rate below the patient's normal resting rate. If the detection indicates physical exertion, the neurostimulator rate increases the patient's heart rate above the normal resting rate.

US Patent Publication 2003/0045909 to Gross et al., which is assigned to the assignee of the present patent application and is incorporated herein by reference, describes apparatus for treating a heart condition of a subject, including an electrode device, which is adapted to be coupled to a vagus nerve of the subject. A control unit is adapted to drive the electrode device to apply to the vagus nerve a stimulating current, which is capable of inducing action potentials in a therapeutic direction in a first set and a second set of nerve fibers of the vagus nerve. The control unit is also adapted to drive the electrode device to apply to the vagus nerve an inhibiting current, which is capable of inhibiting the induced action potentials traveling in the therapeutic direction in the second set of nerve fibers, the nerve fibers in the second set having generally larger diameters than the nerve fibers in the first set.

U.S. Pat. Nos. 6,272,377 and 6,400,982 to Sweeney et al., which are incorporated herein by reference, describe a cardiac rhythm management system that predicts when an arrhythmia will occur and invokes a therapy to prevent or reduce the consequences of the arrhythmia. A cardiac arrhythmia trigger/marker is detected from a patient, and based on the trigger/marker, the system estimates a probability of a cardiac arrhythmia occurring during a predetermined future time interval. The system provides a list of triggers/markers, for which detection values are recurrently obtained at various predetermined time intervals. Based on detection values and conditional probabilities associated with the triggers/markers, a probability estimate of a future arrhythmia is computed. An arrhythmia prevention therapy is selected and activated based on the probability estimate of the future arrhythmia.

U.S. Pat. Nos. 5,411,531 and 5,507,784 to Hill et al., which are incorporated herein by reference, describe a device for controlling the duration of A-V conduction intervals in a patient's heart. Stimulation of the AV nodal fat pad is employed to maintain the durations of the A-V conduction intervals within a desired interval range, which may vary as a function of sensed heart rate or other physiological parameter. AV nodal fat pad stimulation may also be triggered in response to defined heart rhythms such as a rapid rate or the occurrence of premature ventricular depolarizations, to terminate or prevent induction of arrhythmias.

U.S. Pat. No. 6,628,987 to Hill et al., which is incorporated herein by reference, describes a system for performing a medical procedure, such as surgery. The system comprises a sensor to sense a state of cardiac tissue, such as an impending contraction and an indicator to indicate the state of the cardiac tissue.

U.S. Pat. No. 6,449,507 to Hill et al., which is incorporated herein by reference, describes a method for performing a medical procedure, such as surgery. A nerve is stimulated in order to adjust the beating of the heart to a first condition, such as a stopped or slowed condition. The medical procedure is performed on the heart or another organ. The stimulation of the nerve is stopped in order to adjust the beating of the heart to a second condition, such as a beating condition. The heart itself may also be stimulated to a beating condition, such as by pacing. The stimulation of the nerve may be continued in order to allow the medical procedure to be continued.

U.S. Pat. No. 6,542,774 to Hill et al., which is incorporated herein by reference, describes an electro-stimulation device including a pair of electrodes for connection to at least one location in the body that affects or regulates the heartbeat. The electro-stimulation device both electrically arrests the heartbeat and stimulates the heartbeat.

US Patent Application 2003/0216775 to Hill et al., which is incorporated herein by reference, describes a system for performing a medical procedure, such as surgery. The system comprises a compression member for compressing a body portion and a means for controlling the compression.

US Patent Application 2002/0035335 to Schauerte, which is incorporated herein by reference, describes an implantable device for diagnosing and distinguishing supraventricular and ventricular tachycardias. The device includes electrodes for stimulating parasympathetic nerves of the atrioventricular and/or sinus node; electrodes for stimulating the atria and ventricles and/or for ventricular cardioversion/defibrillation; a device for producing electrical parasympathetic stimulation pulses passed to the electrodes; a device for detecting the atrial and/or ventricular rate, by ascertaining a time interval between atrial and/or ventricular depolarization; a device for programming a frequency limit above which a rate of the ventricles is recognized as tachycardia; a comparison device for comparing the measured heart rate during parasympathetic stimulation to the heart rate prior to or without parasympathetic stimulation and/or to the frequency limit, which delivers an output signal when with parasympathetic stimulation the heart rate falls below the comparison value by more than a predetermined amount; and an inhibition unit which responds to the output signal to inhibit ventricular myocardial over-stimulation therapy.

U.S. Pat. Nos. 6,240,314 and 6,493,585 to Plicchi et al., which are incorporated herein by reference, describe electrodes adapted to generate electrical stimulation pulses at least one first intensity level and at least one second intensity level. The first and second intensity levels are above and below a given stimulation threshold, respectively. The synchronous or asynchronous delivery of second-level pulses is described as enabling the conduction of the atrioventricular node to be modulated by electrotonic effect, for example, to reduce ventricular frequency in the event of atrial fibrillation.

U.S. Pat. No. 6,381,499 to Taylor et al., which is incorporated herein by reference, describes techniques for facilitating coronary surgery on the beating heart by electrically stimulating the vagus nerve to purposely temporarily stop or substantially reduce the beating of the heart under precisely controlled conditions.

U.S. Pat. No. 6,564,096 to Mest, which is incorporated herein by reference, describes a method for regulating the heart rate of a patient, comprising inserting into a blood vessel of the patient a catheter having an electrode assembly at its distal end. The electrode assembly comprises a generally circular main region that is generally transverse to the axis of the catheter and on which is mounted at least one electrode. The catheter is directed to an intravascular location wherein the at least one electrode on the electrode assembly is adjacent a selected cardiac sympathetic or parasympathetic nerve. A stimulus is delivered through the at least one electrode, the stimulus being selected to stimulate the adjacent sympathetic or parasympathetic nerve to thereby cause a regulation of the patient's heart rate.

The effect of vagal stimulation on heart rate and other aspects of heart function, including the relationship between the timing of vagal stimulation within the cardiac cycle and the induced effect on heart rate, has been studied in animals. For example, Zhang Y et al., in "Optimal ventricular rate slowing during atrial fibrillation by feedback AV nodal-selective vagal stimulation," Am J Physiol Heart Circ Physiol 282:H1102-H1110 (2002), describe the application of selective vagal stimulation by varying the nerve stimulation intensity, in order to achieve graded slowing of heart rate. This article is incorporated herein by reference.

The following articles and book, which are incorporated herein by reference, may be of interest:

Levy M N et al., in "Parasympathetic Control of the Heart," *Nervous Control of Vascular Function*, Randall W C ed., Oxford University Press (1984)

Levy M N et al. ed., Vagal Control of the Heart: Experimental Basis and Clinical Implications (The Bakken Research Center Series Volume 7), Futura Publishing Company, Inc., Armonk, N.Y. (1993)

Randall W C ed., *Neural Regulation of the Heart*, Oxford University Press (1977), particularly pages 100-106.

Armour J A et al. eds., *Neurocardiology*, Oxford University Press (1994)

Perez M G et al., "Effect of stimulating non-myelinated vagal axon on atrio-ventricular conduction and left ventricular function in anaesthetized rabbits," Auton Neurosco 86 (2001)

Jones, J F X et al., "Heart rate responses to selective stimulation of cardiac vagal C fibres in anaesthetized cats, rats and rabbits," J Physiol 489 (Pt 1):203-14 (1995)

Wallick D W et al., "Effects of ouabain and vagal stimulation on heart rate in the dog," Cardiovasc. Res., 18(2):75-9 (1984)

Martin P J et al., "Phasic effects of repetitive vagal stimulation on atrial contraction," Circ. Res. 52(6):657-63 (1983)

Wallick D W et al., "Effects of repetitive bursts of vagal activity on atrioventricular junctional rate in dogs," Am J Physiol 237(3):H275-81 (1979)

Wallick D W et al., "Selective AV nodal vagal stimulation improves hemodynamics during acute atrial fibrillation in dogs," Am J Physiol Heart Circ Physiol 281: H1490-H1497 (2001)

Fuster V and Ryden L E et al., "ACC/AHA/ESC Practice Guidelines—Executive Summary," J Am Coll Cardiol 38(4): 1231-65 (2001)

Fuster V and Ryden L E et al., "ACC/AHA/ESC Practice Guidelines—Full Text," J Am Coll Cardiol 38(4):1266i-1266lxx (2001)

Morady F et al., "Effects of resting vagal tone on accessory atrioventricular connections," Circulation 81(1):86-90 (1990).

Waninger M S et al., "Electrophysiological control of ventricular rate during atrial fibrillation," PACE 23:1239-1244 (2000)

Wijffels M C et al., "Electrical remodeling due to atrial fibrillation in chronically instrumented conscious goats: roles of neurohumoral changes, ischemia, atrial stretch, and high rate of electrical activation," Circulation 96(10):3710-20 (1997)

Wijffels M C et al., "Atrial fibrillation begets atrial fibrillation," Circulation 92:1954-1968 (1995)

Goldberger A L et al., "Vagally-mediated atrial fibrillation in dogs: conversion with bretylium tosylate," Int J Cardiol 13(1):47-55 (1986)

Takei M et al., "Vagal stimulation prior to atrial rapid pacing protects the atrium from electrical remodeling in anesthetized dogs," Jpn Circ J 65(12):1077-81 (2001)

Friedrichs G S, "Experimental models of atrial fibrillation/flutter," J Pharmacological and Toxicological Methods 43:117-123 (2000)

Hayashi H et al., "Different effects of class Ic and III antiarrhythmic drugs on vagotonic atrial fibrillation in the canine heart," Journal of Cardiovascular Pharmacology 31:101-107 (1998)

Morillo C A et al., "Chronic rapid atrial pacing. Structural, functional, and electrophysiological characteristics of a new model of sustained atrial fibrillation," Circulation 91:1588-1595 (1995)

Lew S J et al., "Stroke prevention in elderly patients with atrial fibrillation," Singapore Med J 43(4):198-201 (2002)

Higgins C B, "Parasympathetic control of the heart," Pharmacol. Rev. 25:120-155 (1973)

Hunt R, "Experiments on the relations of the inhibitory to the accelerator nerves of the heart," J. Exptl. Med. 2:151-179 (1897)

Billette J et al., "Roles of the AV junction in determining the ventricular response to atrial fibrillation," Can J Physiol Pharamacol 53(4)575-85 (1975)

Stramba-Badiale M et al., "Sympathetic-Parasympathetic Interaction and Accentuated Antagonism in Conscious Dogs," American Journal of Physiology 260 (2Pt 2):H335-340 (1991)

Garrigue S et al., "Post-ganglionic vagal stimulation of the atrioventricular node reduces ventricular rate during atrial fibrillation," PACE 21(4), 878 (Part II) (1998)

Kwan H et al., "Cardiovascular adverse drug reactions during initiation of antiarrhythmic therapy for atrial fibrillation," Can J Hosp Pharm 54:10-14 (2001)

Jidéus L, "Atrial fibrillation after coronary artery bypass surgery: A study of causes and risk factors," Acta Universitatis Upsaliensis, Uppsala, Sweden (2001)

Borovikova L V et al., "Vagus nerve stimulation attenuates the systemic inflammatory response to endotoxin," Nature 405(6785):458-62 (2000)

Wang H et al., "Nicotinic acetylcholine receptor alpha-7 subunit is an essential regulator of inflammation," Nature 421:384-388 (2003)

Vanoli E et al., "Vagal stimulation and prevention of sudden death in conscious dogs with a healed myocardial infarction," Circ Res 68(5):1471-81 (1991)

De Ferrari G M, "Vagal reflexes and survival during acute myocardial ischemia in conscious dogs with healed myocardial infarction," Am J Physiol 261(1 Pt 2):H63-9 (1991)

Li D et al., "Promotion of Atrial Fibrillation by Heart Failure in Dogs: Atrial Remodeling of a Different Sort," Circulation 100(1):87-95 (1999)

Feliciano L et al., "Vagal nerve stimulation during muscarinic and beta-adrenergic blockade causes significant coronary artery dilation," Cardiovasc Res 40(1):45-55 (1998)

Carlson M D et al., "Selective stimulation of parasympathetic nerve fibers to the human sinoatrial node," Circulation 85:1311-1317 (1992)

Pagé P L et al., "Regional distribution of atrial electrical changes induced by stimulation of extracardiac and intracardiac neural elements," J Thorac Cardiovasc Surg 109(2):377-88 (1995)

Masato Tsuboi et al., "Inotropic, chronotropic, and dromotropic effects mediated via parasympathetic ganglia in the dog heart," Am J Physiol Heart Circ Physiol 279: H1201-H1207 (2000)

Furukawa Y et al., "Differential blocking effects of atropine and gallamine on negative chronotropic and dromotropic responses to vagus stimulation in anesthetized dogs," J Pharmacol Exp Ther 251(3):797-802 (1989)

Bluemel K M, "Parasympathetic postganglionic pathways to the sinoatrial node," J Physiol 259(5 Pt 2):H1504-10 (1990)

Mazgalev T N, "AV Nodal Physiology," Heart Rhythm Society (www.hrsonline.org) (no date)

Bibevski S et al., "Ganglionic Mechanisms Contribute to Diminished Vagal Control in Heart Failure," Circulation 99:2958-2963 (1999)

Hirose M et al., "Pituitary Adenylate Cyclase-Activating Polypeptide-27 Causes a Biphasic Chronotropic Effect and Atrial Fibrillation in Autonomically Decentralized, Anesthetized Dogs," J Pharmacol Exp Ther 283(2):478-87 (1997)

Chen S A et al., "Intracardiac stimulation of human parasympathetic nerve fibers induces negative dromotropic effects: implication with the lesions of radiofrequency catheter ablation," J Cardiovasc Electrophysiol 9(3):245-52 (1998)

Cooper et al., "Neural effects on sinus rate and atrial ventricular conduction produced by electrical stimulation from a transvenous electrode catheter in the canine right pulmonary artery" Circ Res Vol. 46(1):48-57 (1980)

Heart rate variability is considered an important determinant of cardiac function. Heart rate normally fluctuates within a normal range in order to accommodate constantly changing physiological needs. For example, heart rate increases during waking hours, exertion, and inspiration, and decreases during sleeping, relaxation, and expiration. Two representations of heart rate variability are commonly used: (a) the standard deviation of beat-to-beat R-R interval differences within a certain time window (i.e., variability in the time domain), and (b) the magnitude of variability as a function of frequency (i.e., variability in the frequency domain).

Short-term (beat-to-beat) variability in heart rate represents fast, high-frequency (HF) changes in heart rate. For example, the changes in heart rate associated with breathing are characterized by a frequency of between about 0.15 and about 0.4 Hz (corresponding to a time constant between about 2.5 and 7 seconds). Low-frequency (LF) changes in heart rate (for example, blood pressure variations) are characterized by a frequency of between about 0.04 and about 0.15 Hz (corresponding to a time constant between about 7 and 25 seconds). Very-low-frequency (VLF) changes in heart rate are characterized by a frequency of between about 0.003 and about 0.04 Hz (0.5 to 5 minutes). Ultra-low-frequency (ULF) changes in heart rate are characterized by a frequency of between about 0.0001 and about 0.003 Hz (5 minutes to 2.75 hours). A commonly used indicator of heart rate variability is the ratio of HF power to LF power.

High heart rate variability (especially in the high frequency range, as described hereinabove) is generally correlated with a good prognosis in conditions such as ischemic heart disease and heart failure. In other conditions, such as atrial fibrillation, increased heart rate variability in an even higher frequency range can cause a reduction in cardiac efficiency by producing beats that arrive too quickly (when the ventricle is not optimally filled) and beats that arrive too late (when the ventricle is fully filled and the pressure is too high).

Kamath et al., in "Effect of vagal nerve electrostimulation on the power spectrum of heart rate variability in man," Pacing Clin Electrophysiol 15:235-43 (1992), describe an increase in the ratio of low frequency to high frequency components of the peak power spectrum of heart rate variability during a period without vagal stimulation, compared to periods with vagal stimulation. Iwao et al., in "Effect of constant and intermittent vagal stimulation on the heart rate and heart rate variability in rabbits," Jpn J Physiol 50:33-9 (2000), describe no change in heart rate variability caused by respiration in all modes of stimulation with respect to baseline data. Each of these articles is incorporated herein by reference.

The following articles, which are incorporated herein by reference, may be of interest:

Kleiger R E et al., "Decreased heart rate variability and its association with increased mortality after myocardial infarction," Am J Cardiol 59: 256-262 (1987)

Akselrod S et al., "Power spectrum analysis of heart rate fluctuation: a quantitative probe of beat-to-beat cardiovascular control," Science 213: 220-222 (1981)

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia. U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken.

U.S. Pat. No. 5,330,507 to Schwartz, which is incorporated herein by reference, describes a cardiac pacemaker for preventing or interrupting tachyarrhythmias and for applying pacing therapies to maintain the heart rhythm of a patient within acceptable limits. The device automatically stimulates the right or left vagus nerves as well as the cardiac tissue in a concerted fashion dependent upon need. Continuous and/or phasic electrical pulses are applied. Phasic pulses are applied in a specific relationship with the R-wave of the ECG of the patient.

European Patent Application EP 0 688 577 to Holmström et al., which is incorporated herein by reference, describes a device to treat atrial tachyarrhythmia by detecting arrhythmia and stimulating a parasympathetic nerve that innervates the heart, such as the vagus nerve.

U.S. Pat. Nos. 5,690,681 and 5,916,239 to Geddes et al., which are incorporated herein by reference, describe closed-loop, variable-frequency, vagal-stimulation apparatus for control of ventricular rate during atrial fibrillation. The apparatus stimulates the left vagus nerve, and automatically and continuously adjusts the vagal stimulation frequency as a function of the difference between actual and desired ventricular excitation rates. In an alternative embodiment, the apparatus automatically adjusts the vagal stimulation frequency as a function of the difference between ventricular excitation rate and arterial pulse rate in order to eliminate or minimize pulse deficit.

US Patent Publication 2003/0229380 to Adams et al., which is incorporated herein by reference, describes techniques for electrically stimulating the right vagus nerve in order to reduce the heart rate of a patient suffering from conditions such as chronic heart failure, ischemia, or acute myocardial infarction. The amount of energy of the stimulation may be determined in accordance with a difference between the patient's actual heart rate and a maximum target heart rate for the patient. Delivery of energy is preferably synchronized with the detection of a P-wave. Automatic adjustment of the target heart rate may be based on current day and/or time of day information, and patient physical activity. The voltage, pulse width, or number of pulses in the stimulation may be controlled.

U.S. Pat. No. 5,203,326 to Collins, which is incorporated herein by reference, describes an antiarrhythmia pacemaker which detects a cardiac abnormality and responds with electrical stimulation of the heart combined with vagus nerve stimulation. The pacemaker controls electrical stimulation of the heart in terms of timing, frequency, amplitude, duration and other operational parameters, to provide such pacing therapies as antitachycardia pacing, cardioversion, and defibrillation. The vagal stimulation frequency is progressively increased in one-minute intervals, and, for the pulse delivery rate selected, the heart rate is described as being slowed to a desired, stable level by increasing the pulse current.

U.S. Pat. No. 6,511,500 to Rahme, which is incorporated herein by reference, describes various aspects of the effects of autonomic nervous system tone on atrial arrhythmias, and its interaction with class III antiarrhythmic drug effects. The significance of sympathetic and parasympathetic activation are described as being evaluated by determining the effects of autonomic nervous system using vagal and stellar ganglions stimulation, and by using autonomic nervous system neurotransmitters infusion (norepinephrine, acetylcholine).

U.S. Pat. No. 5,199,428 to Obel et al., which is incorporated herein by reference, describes a cardiac pacemaker for detecting and treating myocardial ischemia. The device automatically stimulates the vagal nervous system as well as the cardiac tissue in a concerted fashion in order to decrease cardiac workload and thereby protect the myocardium.

U.S. Pat. Nos. 5,334,221 to Bardy and 5,356,425 to Bardy et al., which are incorporated herein by reference, describe a stimulator for applying stimulus pulses to the AV nodal fat pad in response to the heart rate exceeding a predetermined rate, in order to reduce the ventricular rate. The device also includes a cardiac pacemaker which serves to pace the ventricle in the event that the ventricular rate is lowered below a pacing rate, and provides for feedback control of the stimulus parameters applied to the AV nodal fat pad, as a function of the determined effect of the stimulus pulses on the heart rate.

U.S. Pat. No. 5,522,854 to Ideker et al., which is incorporated herein by reference, describes techniques for preventing arrhythmia by detecting a high risk of arrhythmia and then stimulating afferent nerves to prevent the arrhythmia.

U.S. Pat. No. 6,434,424 to Igel et al., which is incorporated herein by reference, describes a pacing system with a mode switching feature and ventricular rate regularization function adapted to stabilize or regularize ventricular heart rate during chronic or paroxysmal atrial tachyarrhythmia.

US Patent Application Publication 2002/0120304 to Mest, which is incorporated herein by reference, describes a method for regulating the heart rate of a patient by inserting into a blood vessel of the patient a catheter having an electrode at its distal end, and directing the catheter to an intravascular location so that the electrode is adjacent to a selected cardiac sympathetic or parasympathetic nerve.

U.S. Pat. Nos. 6,006,134 and 6,266,564 to Hill et al., which are incorporated herein by reference, describe an electrostimulation device including a pair of electrodes for connection to at least one location in the body that affects or regulates the heartbeat.

PCT Publication WO 02/085448 to Foreman et al., which is incorporated herein by reference, describes a method for protecting cardiac function and reducing the impact of ischemia on the heart, by electrically stimulating a neural structure capable of carrying the predetermined electrical signal from the neural structure to the "intrinsic cardiac nervous system," which is defined and described therein.

U.S. Pat. No. 5,243,980 to Mehra, which is incorporated herein by reference, describes techniques for discrimination between ventricular and supraventricular tachycardia. In response to the detection of the occurrence of a tachycardia, stimulus pulses are delivered to one or both of the SA and AV nodal fat pads. The response of the heart rhythm to these stimulus pulses is monitored. Depending upon the change or lack of change in the heart rhythm, a diagnosis is made as to the origin of the tachycardia.

U.S. Pat. No. 5,658,318 to Stroetmann et al., which is incorporated herein by reference, describes a device for detecting a state of imminent cardiac arrhythmia in response to activity in nerve signals conveying information from the autonomic nerve system to the heart. The device comprises a sensor adapted to be placed in an extracardiac position and to detect activity in at least one of the sympathetic and vagus nerves.

U.S. Pat. No. 6,292,695 to Webster, Jr. et al., which is incorporated herein by reference, describes a method for controlling cardiac fibrillation, tachycardia, or cardiac arrhythmia by the use of a catheter comprising a stimulating electrode, which is placed at an intravascular location. The electrode is connected to a stimulating means, and stimulation is applied across the wall of the vessel, transvascularly, to a sympathetic or parasympathetic nerve that innervates the heart at a strength sufficient to depolarize the nerve and effect the control of the heart.

U.S. Pat. No. 6,134,470 to Hartlaub, which is incorporated herein by reference, describes an implantable anti-arrhythmia system which includes a spinal cord stimulator coupled to an implantable heart rhythm monitor. The monitor is adapted to detect the occurrence of tachyarrhythmias or of precursors thereto and, in response, trigger the operation of the spinal cord stimulator in order to prevent occurrences of tachyarrhythmias and/or as a stand-alone therapy for termination of tachyarrhythmias and/or to reduce the level of aggressiveness required of an additional therapy such as antitachycardia pacing, cardioversion or defibrillation.

A number of patents and articles describe other methods and devices for stimulating nerves to achieve a desired effect. Often these techniques include a design for an electrode or electrode cuff.

US Patent Publication 2003/0050677 to Gross et al., which is assigned to the assignee of the present patent application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

U.S. Pat. Nos. 4,608,985 to Crish et al. and 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode. The current applied to the electrodes blocks nerve transmission, but, as described, does not activate the nerve fibers in either direction.

U.S. Pat. No. 6,600,956 to Maschino et al., which is incorporated herein by reference, describes an electrode assembly to be installed on a patient's nerve. The electrode assembly has a thin, flexible, electrically insulating circumneural carrier with a split circumferential configuration longitudinally attached to a lead at the distal end thereof. The carrier possesses circumferential resiliency and has at least one flexible, elastic electrode secured to the underside thereof and electrically connected to an electrical conductor in said lead. A fastener serves to close the split configuration of the carrier to prevent separation from the nerve after installation of the electrode assembly onto the nerve. Tear away webbing secured to adjacent serpentine segments of the lead near the carrier enables the lead to lengthen with patient movements.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33 (6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Manfredi M, "Differential block of conduction of larger fibers in peripheral nerve by direct current," Arch. Ital. Biol., 108:52-71 (1970)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

Levy M N, Blattberg B., "Effect of vagal stimulation on the overflow of norepinephrine into the coronary sinus during sympathetic nerve stimulation in the dog," Circ Res 1976 February; 38(2):81-4

Lavallee et al. "Muscarinic inhibition of endogenous myocardial catecholamine liberation in the dog," Can J Physiol Pharmacol 1978 August; 56(4):642-9

Mann D L, Kent R L, Parsons B, Cooper G, "Adrenergic effects on the biology of the adult mammalian cardiocyte," Circulation 1992 February; 85(2):790-804

Mann D L, "Basic mechanisms of disease progression in the failing heart: role of excessive adrenergic drive," Prog Cardiovasc Dis 1998 July-August; 41(1suppl 1):1-8

Barzilai A, Daily D, Zilkha-Falb R, Ziv I, Offen D, Melamed E, Sirv A, "The molecular mechanisms of dopamine toxicity," Adv Neurol 2003; 91:73-82*l*

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

U.S. Pat. No. 6,620,186 to Saphon et al., which is incorporated herein by reference, describes apparatus for testing the impedance of a medical lead connecting an implantable stimulation device to a nerve or a muscle.

U.S. Pat. No. 6,393,323 to Sawan et al., which is incorporated herein by reference, describes an electronic stimulator implant for modulating and synchronizing bladder and sphincter function. The implant is connected to an end of an electrode, and the second end thereof is connected to a sacral nerve. In order to confirm that the implant is operating properly, the implant measures an electrode-tissue contact impedance value.

U.S. Pat. No. 5,891,179 to Er et al., which is incorporated herein by reference, describes techniques for monitoring and displaying lead impedance in real-time for an implantable medical device having an implantable electrical lead. In one example, the implantable medical device is a pacemaker and the impedance monitoring system is within an external programmer device separate from the pacemaker. The '179 patent describes other examples of implantable medical devices, including devices for stimulating or sensing nerves.

U.S. Pat. No. 6,366,813 to DiLorenzo, which is incorporated herein by reference, describes a neurological control system for modulating activity of a component of the nervous system, or any structure interfaced thereto. The system generates neural modulation signals delivered to the nervous system component through one or more intracranial (IC) stimulating electrodes in accordance with treatment parameters. Such treatment parameters may be derived from a neural response to previously delivered neural modulation signals sensed by one or more sensors, each configured to sense a particular characteristic indicative of a neurological or psychiatric condition. Neural modulation signals include any control signal which enhances or inhibits cell activity. The neurological control system considers neural response, in the form of the sensory feedback, as an indication of neurological disease state and/or responsiveness to therapy, in the determination of treatment parameters.

US Patent Application Publication 2004/0172075 to Shafer et al., which is incorporated herein by reference, describes techniques including stimulating a patient's heart while stimulating a nerve of the patient in order to modulate the patient's inflammatory process. More particularly, the techniques include pacing the ventricles of the patient's heart while stimulating the vagal nerve of the patient.

U.S. Pat. No. 6,341,236 to Osorio et al., which is incorporated herein by reference, describes techniques for electrically stimulating the vagus nerve to treat epilepsy with minimized or no effect on the heart. Treatment is carried out by an implantable signal generator, one or more implantable electrodes for electrically stimulating a predetermined stimulation site of the vagus nerve, and a sensor for sensing characteristics of the heart such as a heart rate. The heart rate information from the sensor can be used to determine whether the vagus nerve stimulation is adversely affecting the heart. Once threshold parameters are met, the vagus nerve stimulation may be stopped or adjusted. In an alternative embodiment, a modified pacemaker is used to maintain the heart in desired conditions during the vagus nerve stimulation. In yet another embodiment, a modified pacemaker having circuitry that determines whether a vagus nerve is being stimulated is used. In the event that the vagus nerve is being stimulated, the modified pacemaker may control the heart to maintain it within desired conditions during the vagus nerve stimulation.

SUMMARY OF THE INVENTION

In embodiments of the present invention, a vagal stimulation system for treating a heart condition comprises a multipolar electrode device that is applied to a portion of a vagus nerve that innervates the heart of a subject. The vagal stimulation system further comprises an implanted or external control unit. Typically, the system is configured to treat heart failure and/or heart arrhythmia, such as atrial fibrillation or tachycardia.

In some embodiments of the present invention, the vagal stimulation system is configured to apply vagal stimulation in a series of bursts, each burst including at least one pulse. The application of each of the bursts in each cardiac cycle typically commences after a variable delay after a detected R-wave, P-wave, or other feature of an ECG. The delay is typically calculated in real time using a function, the inputs of which include one or more pre-programmed but updateable constants and one or more sensed parameters, such as the R-R interval between cardiac cycles and/or the P-R interval. Alternatively or additionally, a lookup table of delays is used to determine in real time the appropriate delay for the application of each of the bursts, based on the one or more sensed parameters.

In some embodiments of the present invention, the control unit is configured to drive the electrode device to stimulate the vagus nerve so as to reduce the heart rate of the subject towards a target heart rate. Parameters of stimulation are varied in real time in order to vary the heart-rate-lowering effects of the stimulation. In embodiments of the present invention in which the stimulation is applied in a series of bursts that are synchronized with the cardiac cycle of the subject, such as described hereinabove, parameters of such bursts typically include, but are not limited to: (a) timing of the stimulation within the cardiac cycle, (b) pulse duration (width), (c) pulse repetition interval within each burst, (d) number of pulses per burst, also referred to herein as "pulses per trigger" (PPT), (e) amplitude, (f) duty cycle, (g) choice of vagus nerve, and (h) "on"/"off" ratio and timing (i.e., during intermittent operation). For some applications, the pulse repetition interval is maintained generally constant, while the PPT is varied to regulate the amount of stimulation applied to the vagus nerve.

In some embodiments of the present invention, in which the parameters of the applied bursts include an "on"/"off" ratio, as described herein, the control unit is configured to apply the bursts during short "on" periods and, optionally, to withhold the bursts during short "off" periods. Each of the short "on" periods typically has a duration of less than about 10 seconds, e.g., less than about 5 seconds. When short "off" periods are used, each of the "off" periods typically has a duration of between several seconds and several minutes. The use of such short "on" and/or "off" periods generally allows stimulation of any given strength to be applied as effectively as when using longer "on"/"off" periods, but with fewer potential side effects. For some applications, a desired number of pulses per time period or per heart beat is delivered more effectively and/or with a reduced risk of side effects, by using short "on" periods.

In some embodiments of the present invention, the control unit is configured to apply vagal stimulation in alternating short "high" stimulation and short "low" stimulation periods. For some applications, the "high" stimulation periods have a greater PPT than the "low" stimulation periods. Alternatively or additionally, the "high" stimulation periods have a greater amplitude than the "low" stimulation periods. Further alternatively or additionally, the control unit adjusts one or more of the other parameters described herein in order to apply the "high" stimulation periods with a greater strength than the "low" stimulation periods. Typically, each of the "high" stimulation periods has a duration of less than about 30 seconds (e.g., less than about 5 seconds), and each of the "low" stimulation periods has a duration less than about 30 seconds (e.g., less than about 5 seconds).

In some embodiments of the present invention, the control unit is configured to apply vagal stimulation using feedback, wherein a parameter of the feedback is a target heart rate that is a function of an average heart rate of the subject. The average heart rate is typically calculated over a period of between about 12 hours and about 2 weeks. For some applications, the target heart rate is set equal or approximately equal to the average heart rate of the subject. Alternatively, the target heart rate is set at a rate greater than the average heart rate of the subject, such as a percentage greater than the average heart rate, e.g., about 15% greater. For some applications, the control unit determines the target heart rate in real time, periodically or substantially continuously, by sensing the heart rate of the subject and calculating the average heart rate of the subject. For some applications, the average heart rate is calculated over a most recent time period, e.g., the heart rate over the last half hour. Alternatively, the average heart rate is based on a sensed average heart rate of the subject at rest, and is updated periodically, e.g., several times per day.

In some embodiments of the present application, the control unit is configured to apply vagal stimulation when the heart rate of the subject is below a threshold value, in order to increase the heart rate. The threshold value is typically determined for each subject, e.g., based on the subject's hemodynamic needs and/or individual response to vagal stimulation. For some applications, the control unit is configured to apply fast intermittent stimulation, as defined hereinabove. In some embodiments, the control unit is configured to apply vagal stimulation (a) when the heart rate of the subject is above a first threshold value, in order to reduce the heart rate, and (b) when the heart rate is below a second threshold value, which is lower than the first threshold value, in order to increase the heart rate. The inventors have found that vagal stimulation using the same signal parameters lowers heart rate when the heart rate is above certain threshold values, and raises heart rate when the heart rate is below certain threshold values. The inventors theorize that stimulation at lower heart rates has a greater effect on sympathetic axons of the vagus nerve, while stimulation at higher heart rates has a greater effect on parasympathetic axons. It is to be emphasized that the practice of these embodiments is in no way dependent upon the correctness of this theory.

In some embodiments of the present invention, the control unit is configured to apply vagal stimulation having a strength that is inversely related, e.g., inversely proportional, to a heart rate of the subject, i.e., as the heart rate increases, the strength of the stimulation is decreased. For some applications, the control unit withholds applying the vagal stimulation when the heart rate exceeds a threshold value. Such a configuration generally results in the beneficial effects of vagal stimulation that are not necessarily dependent on the heart-rate reduction effects of such stimulation. Such a configuration generally also results in an improved quality of life for the subject, because the heart rate is allowed to meet the subject's physiological demands.

In some embodiments of the present invention, the control unit comprises or is coupled to an implanted device for monitoring and correcting the heart rate, such as an implantable cardioverter defibrillator (ICD) or a pacemaker (e.g., a biventricular or standard pacemaker). For some applications, the control unit is configured to apply vagal stimulation with stimulation and/or feedback parameters that reduce the likelihood of the vagal stimulation causing the ICD or pacemaker to falsely detect arrhythmia. Alternatively or additionally, the control unit is configured to apply vagal stimulation with stimulation and/or feedback parameters that reduce the likelihood of the occurrence of a "tug-of-war" between the vagal stimulation system and the ICD or pacemaker.

In some embodiments of the present invention, the control unit implements one or more counters, either in hardware or in software running the control unit. Such counters include, but are not limited to, a counter that counts the number of stimulations (i.e., cardiac cycles in which stimulation is applied), a counter that counts the total number of pulses applied to the vagus nerve during a certain period of time, and a counter that counts the number of detected heart beats during a certain period of time.

For some applications, such as when the control unit operates using feedback, an average PPT during stimulations is calculated by dividing the total number of pulses applied in a given period by the number of stimulations, i.e., bursts, applied in the period. The average PPT during stimulations is one indication of the strength of stimulation the control unit needed to apply, based on feedback, in order to maintain the heart rate at the desired target rate.

For some applications, the control unit operates using feedback, and is configured to control a number of pulses applied during each burst of stimulation, responsive to the feedback. Such feedback sometimes results in variations in the average number of pulses per burst. The control unit is configured to monitor the average number of pulses per burst in a given time period. If the average number of pulses per burst exceeds a maximum threshold value over the given period of time, the control unit modifies the parameters of stimulation so as to reduce the average number of pulses per burst. For example, the maximum threshold value may be about 3 pulses per burst. Typically, the parameters adjusted by the control unit include: (a) one or more of the feedback parameters, such as target heart rate and/or a reaction speed parameter governing the feedback, and/or (b) one or more stimulation parameters, such as stimulation amplitude, pulse duration, and/or maximum number of pulses within a burst.

For some applications, the control unit operates using feedback, which results in a variable number of bursts per heart beat and/or per unit time. (For example, a burst may be applied every 1-60 heart beats, or every 0.3-60 seconds, as dictated by a feedback algorithm.) Such feedback sometimes results in high- and/or low-frequency variations in the duty cycle. (Duty cycle is the number of bursts applied during a time period divided by the total number of heart beats during that period.) The control unit is configured to monitor the average duty cycle in a given time period. If the average exceeds a maximum threshold value, the control unit adjusts one or more parameters, typically including: (a) one or more of the feedback parameters, such as target heart rate and/or a reaction speed parameter governing the feedback, and/or (b) one or more stimulation parameters, such as amplitude, pulse duration, and/or maximum number of pulses within a burst.

For some applications, in which the control unit is configured to operate in intermittent "on"/"off" periods, as described hereinabove, the monitored average duty cycle is used in combination with the ratio of the "on" duration to "off" duration in order to determine the magnitude of the heart-rate-lowering effect of the vagal stimulation. A duty cycle less than the "on"/"off" ratio indicates that the stimulation is causing lowering of the heart rate, while a duty cycle equal to the "on"/"off" ratio indicates that no such lowering of the heart rate is occurring. Typically, the control unit monitors the average duty cycle over a time period that includes at least one full "on" period and one full "off" period, such as several "on" and "off" periods.

In some embodiments of the present invention, the control unit operates using feedback, and is configured to set a maximum allowable level of stimulation. The control unit does not apply stimulation beyond this maximum level even if the feedback algorithm calls for increased stimulation. A physician typically sets the maximum level based on considerations such as possible side effects of stimulation, safety, and physiological tolerance. Exemplary maximum levels include, but are not limited to:

pulses per burst of between about 2 and about 20 pulses, e.g., about 8 pulses;

peak power consumption of less than 1 watt;

maximum continuous stimulation period, expressed in either heart beats or units of time; and a duty cycle of between about 5% and about 100%, e.g., 20%, in a time frame of between about 5 seconds and several weeks, e.g., one day.

In some embodiments of the present invention, the control unit is configured to gradually ramp the commencement and/or termination of stimulation. In order to achieve the gradual ramp, the control unit is typically configured to gradually modify one or more stimulation parameters, such as those described hereinabove, e.g., pulse amplitude, PPT, pulse frequency, pulse width, "on" time, and/or "off" time. As appropriate, one or more of these parameters are varied by less than 50% of a pre-termination value per heart beat, in order to achieve the gradual ramp. For example, stimulation at 5 PPT may be gradually terminated by reducing the PPT by 1 pulse per hour. Alternatively, one or more of the parameters are varied by less than 5% per heart beat, in order to achieve the gradual ramp. Terminating stimulation gradually, rather than suddenly, may reduce the likelihood of a rebound acceleration of heart rate that sometimes occurs upon termination of vagal stimulation. For some applications, the control unit is configured to gradually increase the strength of stimulation according to a predetermined schedule. Such a gradual increase is typically appropriate during the first several days of use of the stimulation system by a new subject, and/or when changing from one mode of operation to a different mode of operation. For example, the strength of stimulation may be increased less than 50% per hour, or less than 10% per day.

In some embodiments of the present invention, the control unit is configured to store a series of one or more physiological parameters measured by the stimulation system, in response to receiving an external command to store the parameters. This allows a physician to specify precisely when to begin recording the series, which enables the physician to monitor acute changes in the subject. For example, in order to test external and/or stimulation effects on heart rate, the physician may begin recording the series prior to: (a) instructing the subject to change his position, (b) applying carotid massage to the subject, (c) adjusting stimulation and/or feedback parameters, and/or (d) applying stimulation to the subject using stimulation parameters the physician would like to evaluate.

In some embodiments of the present invention, a subject's reaction to stimulation using the stimulation system is evaluated while the subject exercises. For some applications, a physician initially sets stimulation parameters of the system while the subject is at rest with a relatively low heart rate. The subject then performs the exercise, which increases the heart rate to a level the physician considers to be at least the maximum level the subject is likely to experience during normal daily activity. Using feedback, the control unit reacts to the increased heart rate by modifying one or more stimulation parameters to increase the level of stimulation. This increased level of stimulation represents the maximum stimulation likely to be applied to the subject during use of the system. Therefore, such stimulation is likely to produce the maximum potential side effects of stimulation that the subject may experience. The physician evaluates the subject at this increased level of stimulation in order to assess these side effects and the tolerance of the subject to stimulation by the system. Based on this evaluation, the physician may modify the stimulation parameters, or make other decisions regarding the subject's treatment.

In some embodiments of the present invention, for applications in which the control unit is configured to apply vagal stimulation intermittently, as described hereinabove, the control unit begins the stimulation with an "off" period, rather than with an "on" period. As a result, a delay having the duration of an "off" period occurs prior to beginning stimulation. Alternatively or additionally, whether or not configured to apply stimulation intermittently, the control unit is configured to delay beginning the application of stimulation for a certain time period after receiving an external command to apply the stimulation. For some applications, the length of the time period is determined responsive to the output of a pseudo-random number generator. The use of these delaying techniques generally reduces a subject's anticipation of any discomfort that he may associate with stimulation, and disassociates the sensations of stimulation from the physician and/or an external control device such as a wand.

In some embodiments of the present invention, a method for facilitating the determination of vagal stimulation parameters comprises: (a) applying intermittent vagal stimulation, as described hereinabove, during a calibration period of time that includes a plurality of different naturally-occurring heart rates; (b) for each "on" period and each "off" period, calculating an average heart rate during the period; and (c) segmenting the average heart rates during the "off" periods into a plurality of heart rate ranges; and (d) separately evaluating the effect of vagal stimulation on heart rates within each heart rate range, by calculating an average difference in average heart rate between "on" and "off" periods within the given heart rate range. This analysis is used to determine separate stimulation and feedback parameters for each range of heart rates.

In some embodiments of the present invention, a method for surgically implanting an electrode device comprises placing the electrode device around a vagus nerve, introducing conductive solution (e.g., saline solution) into the electrode device such that the solution is in contact with both the electrodes and the nerve, and measuring an impedance of the electrodes during the implantation procedure. Such impedance measurement enables the surgeon to determine during the procedure (a) whether the electrodes are positioned appropriately, (b) whether sufficient conductive solution has been introduced into and remained in the electrode device, (c) whether the electrodes are the correct size for the nerve, and (d) whether the electrodes are in good contact with the nerve.

For some applications, parasympathetic stimulation of the vagus nerve is applied responsive to one or more sensed physiological parameters or other parameters, such as heart rate, electrocardiogram (ECG), blood pressure, indicators of cardiac contractility, cardiac output, norepinephrine concentration, baroreflex sensitivity, or motion of the subject. For some applications, stimulation is applied in a closed-loop system in order to achieve and maintain a desired heart rate responsive to one or more such sensed parameters.

"Vagus nerve," and derivatives thereof, as used in the specification and the claims, is to be understood to include portions of the left vagus nerve, the right vagus nerve, and branches of the vagus nerve such as the superior cardiac nerve, superior cardiac branch, and inferior cardiac branch. Similarly, stimulation of the vagus nerve is described herein by way of illustration and not limitation, and it is to be understood that stimulation of other autonomic nerves, including nerves in the epicardial fat pads, for treatment of heart conditions or other conditions, is also included within the scope of the present invention.

"Heart failure," as used in the specification and the claims, is to be understood to include all forms of heart failure, including ischemic heart failure, non-ischemic heart failure, and diastolic heart failure.

There is therefore provided, in accordance with an embodiment of the present invention, apparatus including:

an electrode device, adapted to be coupled to a site of a subject; and a control unit, adapted to drive the electrode device to apply a current to the site intermittently during alternating "on" and "off" periods, each of the "on" periods having an "on" duration equal to between 1 and 10 seconds, and each of the "off" periods having an "off" duration equal to at least 50% of the "on" duration.

In an embodiment, the site is selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject, and the electrode device is adapted to be coupled to the selected site.

For some applications, the control unit is adapted to configure the "on" duration to be equal to between 1 and 5 seconds. For some applications, the control unit is adapted to configure the "off" duration to be equal to at least 100% of the "on" duration.

For some applications, the control unit is adapted to drive the electrode device to apply the current using a set of one or more parameters, and set at least one duration selected from the list consisting of: the "on" duration and the "off" duration, so as to reduce a heart rate of the subject by at least 10% of a heart rate reduction achievable when current is applied continuously using the set of parameters.

For some applications, the control unit is adapted to reduce a heart rate of the subject by at least 5%.

For some applications, the control unit is adapted to drive the electrode device to apply the current using a set of one or more parameters, and set at least one duration selected from the list consisting of: the "on" duration and the "off" duration, so as to reduce side effects of the current application compared to side effects when current is applied continuously using the set of parameters.

For some applications, the control unit is adapted to begin the intermittent driving of the electrode device during one of the "off" periods.

For some applications, the control unit is adapted to configure the current to reduce a heart rate of the subject. Alternatively, the control unit is adapted to configure the current to increase a heart rate of the subject. Further alternatively, the control unit is adapted to configure the current to minimize an effect of the applying of the current on a heart rate of the subject.

In an embodiment, the control unit is adapted to drive the electrode device to apply the current in respective bursts of pulses in each of a plurality of cardiac cycles of the subject. For some applications, the control unit is configured to drive the electrode device to apply a desired number of pulses per time period by setting at least one duration selected from the list consisting of: the "on" duration and the "off" duration. For some applications, the control unit is configured to drive the electrode device to apply a desired number of pulses per cardiac cycle by setting at least one duration selected from the list consisting of: the "on" duration and the "off" duration. For some applications, the control unit is adapted to apply a desired overall number of pulses per cardiac cycle over a time period including "on" and "off" periods, by applying a calculated number of pulses per cardiac cycle only during the "on" periods, the calculated number equal to the product of (a) the desired overall number and (b) the quotient of (i) the "on" duration plus the "off" duration and (ii) the "on" duration.

For some applications, the control unit is adapted to:
configure each of the pulses to have a duration of between 100 microseconds and 1 millisecond, and to have an amplitude of between 0.1 and 4 milliamps,
configure each of the bursts to have a duration of between 1 and 60 milliseconds, and to contain between 1 and 5 pulses,
configure the pulses within each of the bursts to have a pulse repetition interval of between 1 and 10 milliseconds, and
drive the electrode device to apply each of the bursts after a delay following an R-wave of the subject, the delay having a duration of between 100 and 700 milliseconds.

For some applications, the control unit is adapted to:
configure each of the pulses to have a duration of between 200 microseconds and 5 milliseconds, and to have an amplitude of between 0.5 and 5 milliamps,
configure each of the bursts to have a duration of between 0.2 and 40 milliseconds, and to contain between 1 and 10 pulses,
configure the pulses within each of the bursts to have a pulse repetition interval of between 2 and 10 milliseconds, and
drive the electrode device to apply each of the bursts after a variable delay following a P-wave of the subject, the delay having a duration equal to between two-thirds and 90% of a duration of a cardiac cycle of the subject.

In an embodiment, the site includes the vagus nerve, and the electrode device is adapted to be coupled to the vagus nerve. For some applications, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the control unit is adapted to configure the current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

There is also provided, in accordance with an embodiment of the present invention, apparatus including:
an electrode device, adapted to be coupled to a site of a subject; and
a control unit, adapted to drive the electrode device to apply a current to the site intermittently during alternating "high" and "low" strength periods, the "high" strength greater than the "low" strength, a duration of each of the "high" and "low" strength periods being greater than 1 second.

In an embodiment, the site is selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject, and the electrode device is adapted to be coupled to the selected site.

For some applications, the control unit is adapted to configure the current such that the "high" strength has a greater amplitude than the "low" strength. For some applications, the control unit is adapted to configure the current to reduce a heart rate of the subject. Alternatively, the control unit is adapted to configure the current to increase a heart rate of the subject. Further alternatively, the control unit is adapted to configure the current to minimize an effect of the applying of the current on a heart rate of the subject.

For some applications, the control unit is adapted to:
during the "high" and "low" strength periods, drive the electrode device to apply the current in respective bursts of pulses in each of a plurality of cardiac cycles of the subject,
configure each of the pulses to have a duration of between 100 microseconds and 1 millisecond, and to have an amplitude of between 0.1 and 4 milliamps,
configure each of the bursts to have a duration of between 1 and 60 milliseconds, and to contain between 1 and 5 pulses,
configure the pulses within each of the bursts to have a pulse repetition interval of between 1 and 10 milliseconds, and _p drive the electrode device to apply each of the bursts after a delay following an R-wave of the subject, the delay having a duration of between 100 and 700 milliseconds.

For some applications, the control unit is adapted to set a duration of each of the "high" strength periods to be less than 30 seconds, such as less than 5 seconds. For some applications, the control unit is adapted to set a duration of each of the "low" strength periods to be less than 30 seconds, such as less than 5 seconds.

In an embodiment, the site includes the vagus nerve, and the electrode device is adapted to be coupled to the vagus nerve. For some applications, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the control unit is adapted to configure the current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

In an embodiment, the control unit is adapted to drive the electrode device to apply the current in respective bursts of pulses in each of a plurality of cardiac cycles of the subject. For some applications, the control unit is adapted to drive the electrode device to apply a greater number of pulses per burst during the "high" strength periods than during the "low" strength periods.

For some applications, the control unit is adapted to:

configure each of the pulses to have a duration of between 200 microseconds and 5 milliseconds, and to have an amplitude of between 0.5 and 5 milliamps, configure each of the bursts to have a duration of between 0.2 and 40 milliseconds, and to contain between 1 and 10 pulses, configure the pulses within each of the bursts to have a pulse repetition interval of between 2 and 10 milliseconds, and drive the electrode device to apply each of the bursts after a variable delay following a P-wave of the subject, the delay having a duration equal to between two-thirds and 90% of a duration of a cardiac cycle of the subject.

There is further provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and a control unit, adapted to drive the electrode device to apply a current to the site capable of reducing a heart rate of the subject by at least 5%, the control unit having a peak power consumption of less than 1 watt.

There is still further provided, in accordance with an embodiment of the present invention, apparatus including:

an electrode device, adapted to be coupled to a site of a subject;

a sensing element, adapted to sense heart beats of the subject; and a control unit, adapted to drive the electrode device to apply a current to the site intermittently during alternating "on" and "off" periods, durations of which "on" and "off" periods are expressed in units of sensed heart beats, each of the "on" periods having an "on" duration equal to a first number of sensed heart beats, and each of the "off" periods having an "off" duration equal to a second number of sensed heart beats.

In an embodiment, the site is selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject, and the electrode device is adapted to be coupled to the selected site.

For some applications, the electrode device includes one or more electrodes, and the sensing element includes at least one of the electrodes.

For some applications, each "on" period includes between 1 and 30 sensed heart beats. For some applications, each "off" period includes between 5 and 40 sensed heart beats, or between 40 and 300 sensed heart beats. For some applications, each "on" period includes exactly one sensed heart beat, and each "off" period includes exactly one sensed heart beat.

For some applications, the control unit is adapted to drive the electrode device to apply the current using a set of one or more parameters, and set at least one duration selected from the list consisting of: the "on" duration and the "off" duration, so as to reduce a heart rate of the subject by at least 10% of a heart rate reduction achievable when current is applied continuously using the set of parameters.

For some applications, the control unit is adapted to begin the intermittent driving of the electrode device during one of the "off" periods. For some applications, the control unit is adapted to configure the current to reduce a heart rate of the subject. Alternatively, the control unit is adapted to configure the current to increase a heart rate of the subject. Further alternatively, the control unit is adapted to configure the current to minimize an effect of the applying of the current on a heart rate of the subject.

In an embodiment, the control unit is adapted to drive the electrode device to apply the current in respective bursts of pulses in each of a plurality of cardiac cycles of the subject. For some applications, the control unit is configured to drive the electrode device to apply a desired number of pulses per cardiac cycle by setting at least one duration selected from the list consisting of: the "on" duration and the "off" duration.

For some applications, the control unit is adapted to:

configure each of the pulses to have a duration of between 100 microseconds and 1 millisecond, and to have an amplitude of between 0.1 and 4 milliamps, configure each of the bursts to have a duration of between 1 and 60 milliseconds, and to contain between 1 and 5 pulses, configure the pulses within each of the bursts to have a pulse repetition interval of between 1 and 10 milliseconds, and drive the electrode device to apply each of the bursts after a delay following an R-wave of the subject, the delay having a duration of between 100 and 700 milliseconds.

For some applications, the control unit is adapted to:

configure each of the pulses to have a duration of between 200 microseconds and 5 milliseconds, and to have an amplitude of between 0.5 and 5 milliamps, configure each of the bursts to have a duration of between 0.2 and 40 milliseconds, and to contain between 1 and 10 pulses, configure the pulses within each of the bursts to have a pulse repetition interval of between 2 and 10 milliseconds, and drive the electrode device to apply each of the bursts after a variable delay following a P-wave of the subject, the delay having a duration equal to between two-thirds and 90% of a duration of a cardiac cycle of the subject.

There is yet further provided, in accordance with an embodiment of the present invention, apparatus including:

an electrode device, adapted to be coupled to a site of a subject;

a sensing element, adapted to sense heart beats of the subject; and a control unit, adapted to drive the electrode device to apply a current to the site intermittently during alternating "on" and "off" periods, durations of one of which type of periods is expressed in units of sensed heart beats, and durations of another of which type of periods is expressed in units of time.

In an embodiment, the site is selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject, and the electrode device is adapted to be coupled to the selected site.

For some applications, the electrode device includes one or more electrodes, and the sensing element includes at least one of the electrodes.

In an embodiment, the control unit is adapted to express the durations of the "off" periods in units of sensed heart beats, and the durations of the "on" periods in units of time. Alternatively, the control unit is adapted to express the durations of the "on" periods in units of sensed heart beats, and the durations of the "off" periods in units of time.

For some applications, each "on" period includes between 1 and 30 sensed heart beats. For some applications, each "off" period has a duration of between 2 and 60 seconds.

There is also provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and a control unit, adapted to drive the electrode device to apply to the site a current that increases a heart rate of the subject.

For some applications, the control unit is adapted to drive the electrode device to apply the current in respective bursts of pulses in each of a plurality of cardiac cycles of the subject.

For some applications, the control unit is adapted to drive the electrode device to apply the current intermittently during alternating "on" and "off" periods, each of the "on" periods having an "on" duration between 1 and 10 seconds, and each of the "off" periods having an "off" duration equal to at least 50% of the "on" duration. For some applications, the control unit is adapted to drive the electrode device to apply the current intermittently during alternating "high" and "low" strength periods, the "high" strength greater than the "low" strength, a duration of each of the "high" and "low" strength periods being greater than 1 second.

In an embodiment, the apparatus includes a sensing element, adapted to sense a heart rate of the subject, and the control unit is adapted to drive the electrode device to apply the current when the heart rate is less than a threshold value. For some applications, the threshold value is less than 80 beats per minute.

In an embodiment, the site includes the vagus nerve, and the electrode device is adapted to be coupled to the vagus nerve. For some applications, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the control unit is adapted to configure the current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

There is yet additionally provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and a control unit, adapted to drive the electrode device to apply to the site a current that both increases a heart rate of the subject when the heart rate is below a first value, and decreases the heart rate when the heart rate is above a second value.

For some applications, the first value is no more than 80 beats per minute. For some applications, the second value is at least 80 beats per minute.

For some applications, the control unit is adapted to drive the electrode device to apply the current in respective bursts of pulses in each of a plurality of cardiac cycles of the subject.

For some applications, the control unit is adapted to drive the electrode device to apply the current intermittently during alternating "on" and "off" periods, each of the "on" periods having an "on" duration equal to between 1 and 10 seconds, and each of the "off" periods having an "off" duration equal to at least 50% of the "on" duration. For some applications, the control unit is adapted to drive the electrode device to apply the current intermittently during alternating "high" and "low" strength periods, the "high" strength greater than the "low" strength, a duration of each of the "high" and "low" strength periods being greater than 1 second.

In an embodiment, the site includes the vagus nerve, and the electrode device is adapted to be coupled to the vagus nerve. For some applications, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the control unit is adapted to configure the current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

There is still additionally provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

a heart rate sensor, adapted to sense a heart rate of the subject; and a control unit, adapted to drive the electrode device to:
responsively to a determination that the heart rate is above a first threshold value, apply to the site a reducing current that reduces the heart rate, and
responsively to a determination that the heart rate is below a second threshold value, apply to the site an increasing current that increases the heart rate.

For some applications, the first threshold value is at least 80 beats per minute. For some applications, the second threshold value is no more than 80 beats per minute.

For some applications, the control unit is adapted to drive the electrode device to apply (a) the reducing current in respective bursts of pulses in each of a plurality of cardiac cycles of the subject, and (b) the increasing current in respective bursts of pulses in each of a plurality of cardiac cycles of the subject.

For some applications, the control unit is adapted to drive the electrode device to apply (a) the reducing current intermittently during alternating "on" and "off" periods, each of the "on" periods having an "on" duration equal to between 1 and 10 seconds, and each of the "off" periods having an "off" duration equal to at least 50% of the "on" duration, and (b) the increasing current intermittently during alternating "on" and "off" periods, each of the "on" periods having an "on" duration equal to between 1 and 10 seconds, and each of the "off" periods having an "off" duration equal to at least 50% of the "on" duration.

For some applications, the control unit is adapted to drive the electrode device to apply (a) the reducing current intermittently during alternating "high" and "low" strength periods, the "high" strength greater than the "low" strength, a duration of each of the "high" and "low" strength periods being greater than 1 second, and (b) the increasing current intermittently during alternating "high" and "low" strength periods, the "high" strength greater than the "low" strength, a duration of each of the "high" and "low" strength periods being greater than 1 second.

In an embodiment, the site includes the vagus nerve, and the electrode device is adapted to be coupled to the vagus nerve. For some applications, the control unit is adapted to configure the reducing current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the control unit is adapted to configure the increasing current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set.

For some applications, the control unit is adapted to configure the reducing current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject. For some applications, the control unit is adapted to configure the increasing current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

There is yet additionally provided, in accordance with an embodiment of the present invention, a method including intermittently applying a current to a site of a subject during alternating "on" and "off" periods, each of the "on" periods having an "on" duration between 1 and 10 seconds, and each of the "off" periods having an "off" duration equal to at least 50% of the "on" duration.

There is still additionally provided, in accordance with an embodiment of the present invention, a method including intermittently applying a current to a site of a subject during alternating "high" and "low" strength periods, the "high" strength greater than the "low" strength, a duration of each of the "high" and "low" strength periods being greater than 1 second.

There is yet additionally provided, in accordance with an embodiment of the present invention, a method including:

applying to a site of a subject a current capable of reducing a heart rate of the subject by at least 5%; and consuming, while at peak power consumption, less than 1 watt while applying the current, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject.

There is also provided, in accordance with an embodiment of the present invention, a method including:

sensing heart beats of a subject; and intermittently applying a current to a site of the subject during alternating "on" and "off" periods, durations of which "on" and "off" periods are expressed in units of sensed heart beats, each of the "on" periods having an "on" duration equal to a first number of sensed heart beats, and each of the "off" periods having an "off" duration equal to a second number of sensed heart beats.

There is further provided, in accordance with an embodiment of the present invention, a method including:

sensing heart beats of a subject; and intermittently applying a current to a site of the subject during alternating "on" and "off" periods, durations of one of which type of periods is expressed in units of sensed heart beats, and durations of another of which type of periods is expressed in units of time.

There is still further provided, in accordance with an embodiment of the present invention, a method including applying to a site of a subject a current that increases a heart rate of the subject, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject.

There is additionally provided, in accordance with an embodiment of the present invention, a method including applying to a site of a subject a current that both increases a heart rate of the subject when the heart rate is below a first value, and decreases the heart rate when the heart rate is above a second value, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject.

There is yet additionally provided, in accordance with an embodiment of the present invention, a method including:

sensing a heart rate of a subject;

responsively to a determination that the heart rate is above a first threshold value, applying to a site of the subject a reducing current that reduces the heart rate, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and responsively to a determination that the heart rate is below a second threshold value, applying to the site an increasing current that increases the heart rate.

There is still additionally provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

a control unit, adapted to be implanted in the subject, and to drive the electrode device to apply an electrical current to the site; and an external monitoring unit, adapted to be positioned external to a body of the subject, and to record timing of the application of the current.

For some applications, the control unit is adapted to drive the electrode device to apply the current to the site intermittently during alternating "on" and "off" periods, each of the "on" periods having an "on" duration equal to at least 1 second, and each of the "off" periods having an "off" duration equal to at least 50% of the "on" duration, and the monitoring unit is adapted to record the timing of at least one type of period selected from the list consisting of "on" and "off" periods.

For some applications, the monitoring unit is adapted to record the timing in real time. For some applications, the control unit is adapted to transmit a communication signal to the external monitoring unit each time the control unit drives the electrode device to apply the current to the site.

In an embodiment, the apparatus includes an electrocardiogram (ECG) monitor, and the monitoring unit is adapted to record the timing by detecting an artifact in the ECG that is indicative of the application of the current. For some applications, the control unit is adapted to drive the electrode device to apply the current synchronized with a feature of the ECG, and the monitoring unit is adapted to detect the artifact only at a known time of current application with respect to the feature of the ECG. For some applications, the ECG monitor is configured to assign a dedicated recording channel thereof to record electrical potential differences between two sides of a neck of the subject, and the monitoring unit is adapted to detect the current application by analyzing the dedicated recording channel.

There is yet additionally provided, in accordance with an embodiment of the present invention, a method including:

applying an electrical current to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and recording, from a location external to the subject, timing of the application of the current.

There is also provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and a control unit, adapted to:
drive the electrode device to apply to the site a current in respective bursts of pulses in each of a plurality of cardiac cycles of the subject, and
count a number of pulses applied to the site.

For some applications, the control unit is adapted to drive the electrode device to apply the current intermittently during alternating "on" and "off" periods, each of the "on" periods having an "on" duration equal to between 1 and 10 seconds, and each of the "off" periods having an "off" duration equal to at least 50% of the "on" duration.

For some applications, the control unit is adapted to configure the current so as to reduce a heart rate of the subject. Alternatively, the control unit is adapted to configure the current so as to increase a heart rate of the subject. Further alternatively, the control unit is adapted to configure the current so as to minimize an effect of the applying of the current on a heart rate of the subject.

For some applications, the control unit is adapted to:
configure each of the pulses to have a duration of between 100 microseconds and 1 millisecond, and to have an amplitude of between 0.1 and 4 milliamps,
configure each of the bursts to have a duration of between 1 and 60 milliseconds, and to contain between 1 and 5 pulses,
configure the pulses within each of the bursts to have a pulse repetition interval of between 1 and 10 milliseconds, and
drive the electrode device to apply each of the bursts after a delay following an R-wave of the subject, the delay having a duration of between 100 and 700 milliseconds.

For some applications, the control unit is adapted to:
configure each of the pulses to have a duration of between 200 microseconds and 5 milliseconds, and to have an amplitude of between 0.5 and 5 milliamps,
configure each of the bursts to have a duration of between 0.2 and 40 milliseconds, and to contain between 1 and 10 pulses,
configure the pulses within each of the bursts to have a pulse repetition interval of between 2 and 10 milliseconds, and
drive the electrode device to apply each of the bursts after a variable delay following a P-wave of the subject, the delay having a duration equal to between two-thirds and 90% of a duration of a cardiac cycle of the subject.

In an embodiment, the control unit is adapted to count the number of pulses applied to the site during a period of time, count a number of bursts applied to the site during the period, and calculate an average number of pulses per burst by dividing the number of pulses counted during the period by the number of bursts counted during the period. For some applications, the control unit is adapted to modify a parameter responsively to the average number of pulses per burst, the parameter selected from the list consisting of: a parameter of the current, and a parameter of a feedback algorithm used by the control unit.

For some applications, the control unit is adapted to determine whether the average number of pulses per burst crosses a threshold value, and, responsively to such a determination, to modify at least one parameter to an extent necessary to cause the average number of pulses per burst to no longer cross the threshold value, the parameter selected from the list consisting of: a parameter of the current, and a parameter of a feedback algorithm used by the control unit. For some applications, the threshold value is between 2 and 4 pulses per burst, and the control unit is adapted to determine whether the average number of pulses per burst exceeds the threshold value.

In an embodiment, the apparatus includes a sensing element, adapted to sense heart beats of the subject, and the control unit is adapted to count a number of bursts applied to the site during a period of time, and count a number of heart beats sensed during the period. For some applications, the control unit is adapted to calculate an average number of bursts per heart beat by dividing the number of bursts counted during the period by the number of heart beats counted during the period. For some applications, the control unit is adapted to modify a parameter responsively to the average number of bursts per heart beat, the parameter selected from the list consisting of: a parameter of the current, and a parameter of a feedback algorithm used by the control unit. For some applications, the control unit is adapted to determine whether the average number of bursts per heart beat crosses a threshold value, and, responsively to such a determination, to modify at least one parameter to an extent necessary to cause the average number of bursts per heart beat to no longer cross the threshold value, the parameter selected from the list consisting of: a parameter of the current, and a parameter of a feedback algorithm used by the control unit.

For some applications, the control unit is adapted to count the number of pulses applied to the site during the period, and calculate an average number of pulses per burst by dividing the number of pulses counted during the period by the number of bursts counted during the period.

In an embodiment, the apparatus includes a sensing element, adapted to sense heart beats of the subject, and the control unit is adapted to count a number of pulses applied to the site during a period of time, and count a number of heart beats sensed during the period. For some applications, the control unit is adapted to count a number of bursts applied to the site during the period, and calculate an average number of pulses per burst by dividing the number of pulses counted during the period by the number of bursts counted during the period. For some applications, the control unit is adapted to calculate an average number of pulses per heart beat by dividing the number of pulses counted during the period by the number of heart beats counted during the period. For some applications, the control unit is adapted to modify a parameter of the current responsively to the average number of pulses per heart beat.

In an embodiment, the site includes the vagus nerve, and the electrode device is adapted to be coupled to the vagus nerve. For some applications, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the control unit is adapted to configure the current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

There is further provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

a sensing element, adapted to sense a physiological parameter of the subject; and a control unit, adapted to:

drive the electrode device to apply a current to the site, configure a parameter of the current responsively to the sensed physiological parameter, calculate an average of the current parameter, over a period of time having a duration of at least 1 minute, and regulate the current parameter such that the average of the current parameter does not exceed a maximum current parameter level regardless of the sensed physiological parameter.

For some applications, the control unit is adapted to regulate the current parameter by modifying a parameter of a feedback algorithm used by the control unit.

For some applications, the control unit is adapted to regulate the current parameter by driving the electrode device to apply the current intermittently during alternating "on" and "off" periods, each of the "on" periods having an "on" duration equal to at least 1 second, and each of the "off" periods having an "off" duration equal to at least 50% of the "on" duration.

For some applications, the control unit is adapted to generate an external notification signal if the average of the current parameter would exceed the maximum current parameter in the absence of the regulating of the current parameter.

For some applications, the control unit is adapted to express the maximum current parameter as a number of contiguous heart beats during which the current is applied. Alternatively, the control unit is adapted to express the maximum current parameter as a time period of continuous current application. Further alternatively, the control unit is adapted to express the maximum current parameter as an average amount of energy applied over a time period.

In an embodiment, the control unit is adapted to drive the electrode device to apply the current in respective bursts of pulses in each of a plurality of cardiac cycles of the subject. For some applications, the control unit is adapted to express the maximum current parameter as the product of (a) pulses per burst and (b) amplitude of the current over a time period. For some applications, the control unit is adapted to express the maximum current parameter level in pulses per burst. For some applications, the maximum current parameter is between 2 and 20 pulses per burst.

For some applications, the control unit is adapted to express the maximum current parameter as a duty cycle over a time period of between 5 seconds and 3 weeks. For some applications, the duty cycle is between 5% and 100%.

For some applications, the control unit is adapted to express the maximum current parameter as power over a time period of between 5 seconds and 3 weeks. For some applications, the maximum current parameter is less than 1 watt.

There is still further provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

a sensing element, adapted to sense a physiological parameter of the subject;

an input element, adapted to receive a command generated external to the apparatus; and a control unit, which includes a memory, the control unit adapted to:
  drive the electrode device to apply a current to the site, and
  in response to receiving the command, store in the memory the physiological parameter sensed at a plurality of points in time.

For some applications, the control unit is adapted to begin storing the physiological parameter sensed at the plurality of points in time, after a delay from a time of receiving the command.

For some applications, the plurality of points in time includes a predetermined number of points in time, and the control unit is adapted to store the physiological parameter sensed at the points in time.

For some applications, the physiological parameter includes an R-R interval of the subject, and the sensing element is adapted to sense the R-R interval. Alternatively or additionally, the physiological parameter includes systolic and diastolic blood pressures of the subject, and the sensing element is adapted to sense the blood pressures. Further alternatively or additionally, the physiological parameter includes at least one feature of an electrocardiogram (ECG) of the subject, and the sensing element includes an ECG monitor.

There is yet further provided, in accordance with an embodiment of the present invention, apparatus including:
  an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;
  an input element, adapted to receive an apparatus activation command generated external to the apparatus; and
  a control unit, adapted to begin driving the electrode device to apply a current to the site, responsively to receiving the activation command, after a delay of at least 5 seconds from a time of receiving the activation command.

For some applications, the control unit is adapted to apply the current intermittently during alternating "on" and "off" periods, each of the "on" periods having an "on" duration equal to at least 1 second, and each of the "off" periods having an "off" duration equal to at least 50% of the "on" duration, a duration of the delay is equal to a duration of a single one of the "off" periods, and the control unit is adapted to begin driving the current after the delay by beginning the intermittent application of the current during one of the "off" periods.

For some applications, the control unit includes a pseudo-random number generator, and the control unit is adapted to set a length of the delay at least in part responsively to an output of the pseudo-random number generator.

There is also provided, in accordance with an embodiment of the present invention, apparatus including:
  an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;
  a heart rate sensor, adapted to sense a heart rate of the subject; and
  a control unit, adapted to:
    drive the electrode device to apply to the site a current, and
    configure the current responsively to a comparison of (a) the sensed heart rate and (b) a target heart rate that is a function of an average heart rate of the subject.

For some applications, the control unit is adapted to determine the target heart rate in real time. For some applications, the control unit is configured to determine the average heart rate of the subject responsively to the sensed heart rate of the subject. For some applications, the control unit is adapted to calculate the average heart rate over a period of between 12 hours and 2 weeks. For some applications, the control unit is adapted to calculate the average heart rate over a period of between 10 minutes and 24 hours.

For some applications, the control unit is adapted to set the target heart rate equal to the average heart rate. For some applications, the control unit is adapted to set the target heart rate to a value within 5% of the average heart rate.

For some applications, the control unit is adapted to determine the average heart rate and the target heart rate in real time. For some applications, the control unit is adapted to determine the average heart rate over a recent time period that ends less than 1 hour prior to the determination. For some applications, the control unit is adapted to determine the average heart rate when the subject is at rest.

For some applications, the control unit is adapted to configure the current so as to reduce the sensed heart rate towards the target heart rate. Alternatively, the control unit is adapted to configure the current so as to increase the sensed heart rate towards the target heart rate.

For some applications, the control unit is adapted to:
  drive the electrode device to apply the current in respective bursts of pulses in each of a plurality of cardiac cycles of the subject,
  configure each of the pulses to have a duration of between 100 microseconds and 1 millisecond, and to have an amplitude of between 0.1 and 4 milliamps,
  configure each of the bursts to have a duration of between 1 and 60 milliseconds, and to contain between 1 and 5 pulses,
  configure the pulses within each of the bursts to have a pulse repetition interval of between 1 and 10 milliseconds, and
  drive the electrode device to apply each of the bursts after a delay following an R-wave of the subject, the delay having a duration of between 100 and 700 milliseconds.

For some applications, the control unit is adapted to set the target heart rate greater than the average heart rate, such as equal to 15% greater than the average heart rate.

In an embodiment, the site includes the vagus nerve, and the electrode device is adapted to be coupled to the vagus nerve. For some applications, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the control unit is adapted to configure the current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

There is yet additionally provided, in accordance with an embodiment of the present invention, apparatus including:
  an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and a control unit, adapted to:

drive the electrode device to apply to the site a current that changes a heart rate of the subject, and gradually modify at least one parameter of the current by less than a percentage selected from the list consisting of: 50% of a pre-termination value per heart beat of the subject, and 5% per heart beat of the subject, until the parameter reaches a desired value, during a transitional period selected from the list consisting of: a commencement of stimulation period, and a termination of stimulation period.

For some applications, the control unit is adapted to gradually modify the parameter during the transitional period, which transitional period includes the commencement of stimulation period and has a duration of at least 24 hours, such that a level of vagal stimulation caused by the current gradually increases.

For some applications, the control unit is adapted to gradually modify the parameter according to a predetermined schedule.

For some applications, the control unit is adapted to gradually modify the parameter by less than 50% per hour. For some applications, the control unit is adapted to gradually modify the parameter by less than 10% per 24-hour period.

For some applications, the percentage is 50% of the pre-termination value per heart beat. For some applications, the percentage is 5% per heart beat.

For some applications, the parameter includes an amplitude of the current, and the control unit is adapted to gradually modify the amplitude.

For some applications, the control unit is adapted to drive the electrode device to apply the current intermittently during alternating "on" and "off" periods, each of the "on" periods having an "on" duration equal to at least 1 second, and each of the "off" periods having an "off" duration equal to at least 50% of the "on" duration, the parameter is selected from the list consisting of: a duration of each of the "on" periods, and a duration of each of the "off" periods, and the control unit is adapted to gradually modify the selected parameter.

For some applications, the control unit is adapted to drive the electrode device to apply the current in respective bursts of pulses in each of a plurality of cardiac cycles of the subject. For some applications, the parameter is selected from the list consisting of: pulses per burst, pulse frequency, and pulse width, and the control unit is adapted to gradually modify the selected parameter.

In an embodiment, the apparatus includes an input element, adapted to receive one or more commands generated external to the apparatus, and the control unit is adapted to gradually modify the parameter at least in part responsively to the commands. For some applications, the commands include a request to return to a previous level of current application, and the control unit is adapted to set the parameter at a previous value of the parameter responsively to the commands.

There is still additionally provided, in accordance with an embodiment of the present invention, apparatus including:

an electrode device, adapted to be coupled to a site of a subject;

a heart rate sensor, adapted to sense a heart rate of the subject; and a control unit, adapted to:

drive the electrode device to apply to the site a current in respective bursts of pulses in each of a plurality of cardiac cycles of the subject, set a number of pulses in each of the bursts, using a feedback algorithm that includes as an input thereto the sensed heart rate, and modify at least one parameter if an average number of pulses per burst crosses a threshold value, the parameter selected from the list consisting of: a parameter of the current, and a parameter of the feedback algorithm.

In an embodiment, the site is selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject, and the electrode device is adapted to be coupled to the selected site.

For some applications, the parameter of the feedback algorithm includes a target heart rate, and the control unit is adapted to modify the target heart rate if the average number of pulses per burst crosses the threshold value. For some applications, the parameter of the feedback algorithm includes an integral slope of the feedback algorithm, and the control unit is adapted to modify the integral slope if the average number of pulses per burst crosses the threshold value.

For some applications, the parameter of the current includes an amplitude of the current, and the control unit is adapted to modify the amplitude if the average number of pulses per burst crosses the threshold value. For some applications, the parameter of the current includes a duration of each of the pulses, and the control unit is adapted to modify the pulse duration if the average number of pulses per burst crosses the threshold value. For some applications, the parameter of the current includes a maximum number of pulses per burst, and the control unit is adapted to modify the maximum number of pulses per burst if the average number of pulses per burst crosses the threshold value.

For some applications, the threshold value is between 2 and 4 pulses per burst, such as 3 pulses per burst.

In an embodiment, the site includes the vagus nerve, and the electrode device is adapted to be coupled to the vagus nerve. For some applications, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the control unit is adapted to configure the current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

There is yet additionally provided, in accordance with an embodiment of the present invention, apparatus including:

an electrode device, adapted to be coupled to a site of a subject;

a heart rate sensor, adapted to sense a heart rate of the subject; and a control unit, adapted to:

drive the electrode device to apply to the site electrical stimulation in respective bursts in each of a plurality of cardiac cycles of the subject, each of the bursts including one or more pulses, set at least one primary parameter of the stimulation, using a feedback algorithm that includes as an input thereto the sensed heart rate, and modify at least one secondary parameter if an average duty cycle of the stimulation crosses a threshold value, the secondary parameter selected from the list consisting of: a parameter of the stimulation, and a parameter of the feedback algorithm.

In an embodiment, the site is selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject, and the electrode device is adapted to be coupled to the selected site.

In an embodiment, the secondary parameter includes the primary parameter, and the control unit is adapted to modify the at least one primary parameter if the average duty cycle crosses the threshold value.

For some applications, the secondary parameter includes a target heart rate, and the control unit is adapted to modify the target heart rate if the average duty cycle of the stimulation crosses the threshold value. For some applications, the secondary parameter includes an integral slope of the feedback algorithm, and the control unit is adapted to modify the integral slope if the average duty cycle of the stimulation crosses the threshold value.

For some applications, the secondary parameter includes an amplitude of the current, and the control unit is adapted to modify the amplitude if the average duty cycle of the stimulation crosses the threshold value. For some applications, the secondary parameter includes a duration of each of the pulses, and the control unit is adapted to modify the pulse duration if the average duty cycle of the stimulation crosses the threshold value. For some applications, the secondary parameter includes a maximum number of pulses per burst, and the control unit is adapted to modify the maximum number if the average duty cycle of the stimulation crosses the threshold value.

In an embodiment, the site includes the vagus nerve, and the electrode device is adapted to be coupled to the vagus nerve. For some applications, the control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the control unit is adapted to configure the current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

There is still additionally provided, in accordance with an embodiment of the present invention, apparatus including:

an electrode device, adapted to be coupled to a site of a subject;

a heart rate sensor, adapted to sense a heart rate of the subject; and a control unit, adapted to:

drive the electrode device to apply to the site, intermittently during alternating "on" and "off" periods, electrical stimulation capable of lowering the heart rate, the stimulation having a duty cycle expressed as a number of stimulations per heart beat, and each of the "on" periods having an "on" duration equal to at least 1 second, and each of the "off" periods having an "off" duration equal to at least 50% of the "on" duration, responsively to the sensed heart rate, set at least one parameter of the stimulation, and determine a magnitude of a heart-rate-lowering effect of the stimulation by comparing an aspect of each "on" period to an aspect of each "off" period.

In an embodiment, the site is selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject, and the electrode device is adapted to be coupled to the selected site.

For some applications, the control unit is adapted to determine a presence of the heart-rate-lowering effect.

For some applications, the aspect of each "on" period includes a duration of each "on" period, and the aspect of each "off" period includes a duration of each "off" period, and the control unit is adapted to determine the magnitude by comparing (a) a ratio of the duration of each "on" period to the duration of each "off" period, to (b) the duty cycle of the stimulation. For some applications, the control unit is adapted to interpret the duty cycle being less than the ratio as indicative of a presence of the heart-rate-lowering effect. For some applications, the control unit is adapted to make the determination based on the duty cycle over a time period that includes at least one full "on" period and one full "off" period.

There is yet additionally provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

a heart rate sensor, adapted to sense a heart rate of the subject; and a control unit, adapted to:

drive the electrode device to apply electrical stimulation to the site, and configure the stimulation to have a strength that is inversely related to the sensed heart rate.

In an embodiment, the control unit is adapted to configure the stimulation to have a strength that is inversely proportional to the sensed heart rate.

For some applications, the control unit is adapted to drive the electrode device to apply the stimulation when the subject is sleeping.

For some applications, the control unit is adapted to drive the electrode device to apply the stimulation intermittently during alternating "on" and "off" periods, each of the "on" periods having an "on" duration equal to between 1 and 10 seconds, and each of the "off" periods having an "off" duration equal to at least 50% of the "on" duration.

In an embodiment, the control unit is adapted to withhold driving the electrode device to apply the stimulation when the sensed heart rate exceeds a threshold value. For some applications, the threshold value is greater than 50 beats per minute. For some applications, the threshold value is less than an average heart rate of the subject. For some applications, the threshold value equals the average heart rate minus a certain number of beats per minute. For some applications, the threshold value equals the average heart rate minus a certain number of standard deviations, such as at least one standard deviation. For some applications, the threshold value equals the average heart rate minus a certain percentage of the heart rate, such as between 1% and 40%.

In an embodiment, the control unit is adapted to drive the electrode device to apply the stimulation in respective bursts of pulses in each of a plurality of cardiac cycles of the subject. In an embodiment, the electrode device is adapted to be coupled to a left vagus nerve of the subject. For some applications, the control unit is adapted to configure each of the pulses to have a duration of between 200 microseconds and 2.5 milliseconds. For some applications, the control unit is adapted to configure each of the pulses to have a duration of between 2.5 and 5 milliseconds. For some applications, the control unit is adapted to configure each of the bursts to have a duration of between 0.2 and 40 milliseconds. For some applications, the control unit is adapted to configure each of the bursts to contain between 1 and 10 pulses. For some applications, the control unit is adapted to configure the pulses within each of the bursts to have a pulse repetition interval of between 2 and 10 milliseconds. For some applications, the control unit is adapted to configure the pulses to have an amplitude of between 0.5 and 5 milliamps.

For some applications, the control unit is adapted to drive the electrode device to apply the bursts less than every heartbeat of the subject. Alternatively, the control unit is adapted to drive the electrode device to apply the bursts once per heartbeat of the subject.

For some applications, the control unit is adapted to drive the electrode device to apply the stimulation to the site intermittently during alternating "on" and "off" periods, each of the "on" periods having a duration of at least 1 second.

For some applications, the control unit is adapted to drive the electrode device to apply each of the bursts after a variable delay following a P-wave of the subject, the delay having a duration equal to between two-thirds and 90% of a duration of a cardiac cycle of the subject.

There is also provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

a sleep detector, adapted to generate a signal indicative of sleeping by the subject; and a control unit, adapted to drive the electrode device to apply a current to the site, responsively to receiving the signal.

For some applications, the sleep detector includes an accelerometer, an electroencephalogram (EEG) device, and/or a clock.

For some applications, the control unit is adapted to configure the current so as to reduce a heart rate of the subject. Alternatively, the control unit is adapted to configure the current so as to minimize an effect of the applying of the current on a heart rate of the subject.

There is further provided, in accordance with an embodiment of the present invention, a method including:

applying to a site of a subject a current in respective bursts in each of a plurality of cardiac cycles of the subject, each of the bursts including two or more pulses, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and counting a number of pulses applied to the site.

There is still further provided, in accordance with an embodiment of the present invention, a method including:

sensing a physiological parameter of a subject;

applying a current to a site of the subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

configuring a parameter of the current responsively to the sensed physiological parameter;

calculating an average of the current parameter, over a period of time having a duration of at least 1 minute; and regulating the current parameter such that the average of the current parameter does not exceed a maximum current parameter level regardless of the sensed physiological parameter.

There is additionally provided, in accordance with an embodiment of the present invention, a method including:

sensing a physiological parameter of a subject;

applying a current to a site of the subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

receiving a command from a location outside of a body of the subject; and in response to receiving the command, storing the physiological parameter sensed at a plurality of points in time.

For some applications, the method includes generating the command, and subsequently instructing the subject to change a position of the subject. For some applications, the method includes generating the command, and subsequently applying carotid massage to the subject.

There is yet additionally provided, in accordance with an embodiment of the present invention, a method including:

receiving an activation command from a location outside of a body of a subject; and beginning to apply a current to a site of the subject, responsively to receiving the activation command, after a delay of at least 5 seconds from a time of receiving the activation command, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject.

There is still additionally provided, in accordance with an embodiment of the present invention, a method including:

sensing a heart rate of a subject;

applying a current to a site of the subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and configuring the current responsively to a comparison of (a) the sensed heart rate and (b) a target heart rate that is a function of an average heart rate of the subject.

There is yet additionally provided, in accordance with an embodiment of the present invention, a method including:

applying to a site of a subject a current that changes a heart rate of the subject, the site selected from the list consisting of: a vagus nerve of the subject, an epicardial fat pad of the subject, a pulmonary vein of the subject, a carotid artery of the subject, a carotid sinus of the subject, coronary sinus of the subject, a vena cava vein of the subject, a right ventricle of the subject, and a jugular vein of the subject; and gradually modifying at least one parameter of the current by less than a percentage selected from the list consisting of: 50% of a pre-termination value per heart beat of the subject, and 5% per heart beat of the subject, until the parameter reaches a desired value, during a transitional period selected from the list consisting of: a commencement of stimulation period, and a termination of stimulation period.

There is still additionally provided, in accordance with an embodiment of the present invention, a method including:

sensing a heart rate of a subject;

applying to a site of the subject a current in respective bursts in each of a plurality of cardiac cycles of the subject, each of the bursts including one or more pulses;

setting a number of pulses in each of the bursts, using a feedback algorithm that includes as an input thereto the sensed heart rate; and modifying at least one parameter if an average number of pulses per burst crosses a threshold value, the parameter selected from the list consisting of: a parameter of the current, and a parameter of the feedback algorithm.

There is yet additionally provided, in accordance with an embodiment of the present invention, a method including:

sensing a heart rate of a subject;

applying to a site of the subject electrical stimulation in respective bursts in each of a plurality of cardiac cycles of the subject, each of the bursts including one or more pulses;

setting at least one primary parameter of the stimulation, using a feedback algorithm that includes as an input thereto the sensed heart rate; and modifying at least one secondary parameter if an average duty cycle of the stimulation crosses a threshold value, the secondary parameter selected from the list consisting of: a parameter of the stimulation, and a parameter of the feedback algorithm.

There is still additionally provided, in accordance with an embodiment of the present invention, a method including:

sensing a heart rate of a subject;

applying to a site of the subject intermittently during alternating "on" and "off" periods, electrical stimulation capable of lowering the heart rate, the stimulation having a duty cycle expressed as a number of stimulations per heart beat, and each of the "on" periods having an "on" duration equal to at least 1 second, and each of the "off" periods having an "off" duration equal to at least 50% of the "on" duration;

responsively to the sensed heart rate, setting at least one parameter of the stimulation; and determining a magnitude of a heart-rate-lowering effect of the stimulation by comparing an aspect of each "on" period to an aspect of each "off" period.

There is yet additionally provided, in accordance with an embodiment of the present invention, a method including:

sensing a heart rate of a subject;

applying electrical stimulation to a site of the subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and configuring the stimulation to have a strength that is inversely related to the sensed heart rate.

There is also provided, in accordance with an embodiment of the present invention, a method including:

detecting sleeping by a subject; and responsively to detecting the sleeping, applying a current to a site of the subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject.

There is further provided, in accordance with an embodiment of the present invention, a method including:

applying a current to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

sensing a first physiological parameter of the subject;

configuring a parameter of the current responsively to the first physiological parameter;

while the subject is exercising, sensing a second physiological parameter of the subject at a plurality of different exercise levels of exertion of the subject; and determining a tolerance of the subject to the application of the current by analyzing the second physiological parameter at the plurality of different exercise levels.

For some applications, applying the current includes applying the current during a plurality of time periods, and configuring at least one parameter of the current to have a different value during each of the time periods, and sensing the second physiological parameter includes sensing the second physiological parameter during the plurality of time periods.

For some applications, the method includes configuring the current responsively to determining the tolerance.

For some applications, a first one of the different exercise levels of exertion includes a resting level of exertion, and sensing the second physiological parameter includes sensing the second physiological parameter at the first exercise level.

For some applications, a first one of the different exercise levels of exertion includes a recovery from exercise level of exertion, and sensing the second physiological parameter includes sensing the second physiological parameter at the first exercise level.

For some applications, the method includes adjusting the parameter of the current so as to achieve a heart rate of the subject at which the heart is maximally effective.

In an embodiment, the site includes the vagus nerve, and applying the current includes applying the current to the vagus nerve.

For some applications, the first physiological parameter includes a heart rate of the subject, and configuring the parameter of the current includes configuring the parameter of the current responsively to the heart rate of the subject. For some applications, configuring the parameter includes increasing a strength of the current responsively to an increase in the heart rate.

There is still further provided, in accordance with an embodiment of the present invention, a method including:

applying a current to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

while the subject is exercising, sensing, at a plurality of different exercise levels of exertion of the subject, a physiological parameter of the subject indicative of an effectiveness of a heart of the subject; and responsively to the physiological parameter, configuring a parameter of the current to change a heart rate of the subject to a rate at which the effectiveness increases.

For some applications, applying the current includes applying the current during a plurality of time periods, and configuring the parameter of the current to have a different value during each of the time periods.

In an embodiment, the site includes the vagus nerve, and applying the current includes applying the current to the vagus nerve.

There is additionally provided, in accordance with an embodiment of the present invention, a method including:

during a calibration period of time that includes a plurality of different naturally-occurring heart rates of a subject, intermittently applying a calibration current to a site of the subject during a plurality of alternating "on" and "off" periods, each of the "on" periods having an "on" duration equal to at least 1 second, and each of the "off" periods having an "off" duration equal to at least 50% of the "on" duration, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

sensing a heart rate of the subject during the calibration period; and for each of two or more of the "on" periods, plotting a point on a graph, a first coordinate of the point indicative of an "on" average heart rate of the subject during the "on" period, and a second coordinate of the point indicative of an "off" average heart rate during at least one of: the "off" period immediately preceding the "on" period, and the "off" period immediately following the "on" period.

For some applications, applying the calibration current includes subjecting the subject to an exercise test during at least a portion of the calibration period.

For some applications, plotting the point includes expressing the "on" and "off" average heart rates as R-R intervals.

For some applications, the first and second coordinates are y- and x-coordinates of the point, respectively, and the method includes interpreting that the point lies above a line defined by x=y as an indication that the "on" average heart rate is less than the "off" average heart rate for the point.

For some applications, applying the calibration current includes:

subjecting the subject to an exercise test during at least a first portion of the calibration period;

instructing the subject to relax during at least a second portion of the calibration period; and instructing the subject to rest during at least a third portion of the calibration period.

For some applications, each of the "on" periods has a duration of between 45 and 75 seconds, and each of the "off" periods has a duration of between 90 and 150 seconds. For some applications, the calibration period includes at least 200 "on" periods and at least 200 "off" periods. For some applications, the calibration period has a duration of at least 24 hours.

In an embodiment, the site includes the vagus nerve, and applying the calibration current includes applying the current to the vagus nerve.

There is also provided, in accordance with an embodiment of the present invention, apparatus including:

an implantable sensor, adapted to sense an electrical parameter of a heart of a subject;

a first control unit, adapted to apply pulses to the heart responsively to the sensed parameter, the pulses selected from the list consisting of: pacing pulses and anti-arrhythmic energy;

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and a second control unit, adapted to drive the electrode device to apply to the site a current that increases parasympathetic tone of the subject and affects a heart rate of the subject, wherein the first and second control units are not under common control, and wherein at least one of the control units is adapted to coordinate an aspect of its operation with an aspect of operation of the other control unit.

In an embodiment, the second control unit is adapted to generate a communication signal indicative of driving the electrode device to apply the current, and the first control unit is adapted to receive the communication signal, and to regulate an aspect of its own operation responsively to receiving the communication signal.

For some applications, the second control unit is adapted to configure the current to reduce the heart rate of the subject.

For some applications, the implantable sensor, the first control unit, the electrode device, and the second control unit are packaged in a single integrated unit. For some applications, the second control unit is adapted to drive the electrode device responsively to the sensed parameter.

In an embodiment, the aspect of the operation of the first control unit includes an aspect of timing of the operation of the first control unit, the aspect of the operation of the second control unit includes an aspect of timing of the operation of the second control unit, and the at least one of the control units is adapted to coordinate the aspect of the timing of the operation of the first control unit with the aspect of the timing of the operation of the second control unit.

In an embodiment, the implantable sensor and the first control unit together include an implantable cardioverter defibrillator (ICD). In an embodiment, the implantable sensor and the first control unit together include a pacemaker. In an embodiment, the implantable sensor and the first control unit together include a pulse generator.

In an embodiment, the second control unit is configured to reduce a likelihood that the current causes the first control unit to falsely detect arrhythmia of the subject.

In an embodiment, the at least one of the control units is configured to reduce a likelihood of an occurrence of a "tug-of-war" between the first and second control units.

In an embodiment, the first control unit is programmed with a flag indicative of the presence of the second control unit, and the first control unit is adapted to withhold coordinating the aspect of the operation responsively to a value of the flag that indicates that the second control unit is not present. Alternatively, in an embodiment, the second control unit is programmed with a flag indicative of the presence of the first control unit, and the at least one of the control units is adapted to withhold coordinating the aspect of the operation responsively to a value of the flag that indicates that the first control unit is not present.

In an embodiment, the first control unit is adapted to identify a stimulus artifact of the current application by the electrode device as being a stimulus artifact of the current application by the electrode device.

For some applications, the second control unit is adapted to generate a communication signal when driving the electrode device to apply the current, and the first control unit is adapted to receive the signal, and, responsively thereto, to withhold applying the pulses.

In an embodiment, the implantable device is adapted to detect an occurrence of arrhythmia only if the arrhythmia continues for a first number of consecutive heart beats, and the control unit is adapted to drive the electrode device to apply the current for a maximum of a second number of consecutive heart beats, the second number less than the first number.

For some applications, the second control unit is adapted to drive the electrode device to apply the current intermittently during alternating "on" and "off" periods, each of the "on" periods having an "on" duration equal to between 1 and 10 seconds, and each of the "off" periods having an "off" duration equal to at least 50% of the "on" duration. For some applications, the second control unit is adapted to drive the electrode device to apply the current in respective bursts of pulses in each of a plurality of cardiac cycles of the subject.

In an embodiment, the first control unit is adapted to withhold attempting to detect a next heart beat during an extended blanking period following detection of a previous heart beat. For some applications, the extended blanking period has a duration of between 20 and 200 ms, and the first control unit is adapted to withhold attempting to detect the next heart beat during the extended blanking period having the duration. For some applications, the second control unit is adapted to drive the electrode device to apply the current only during the extended blanking period.

In an embodiment, the site includes the vagus nerve, and the electrode device is adapted to be coupled to the vagus nerve. For some applications, the second control unit is adapted to configure the current to include a stimulating current, which is capable of inducing action potentials in a first set and a second set of nerve fibers of the vagus nerve, and an inhibiting current, which is capable of inhibiting the induced action potentials traveling in the second set of nerve fibers, the nerve fibers in the second set having generally larger diameters than the nerve fibers in the first set. For some applications, the second control unit is adapted to configure the current to include a stimulating current, which is capable of inducing action potentials in the vagus nerve, and an inhibiting current, which is capable of inhibiting action potentials induced by the stimulating current and traveling in the vagus nerve in an afferent direction toward a brain of the subject.

In an embodiment, the first control unit is adapted to generate a communication signal at each detection of a feature of a cardiac cycle of the subject, and the second control unit is adapted to receive the signal, and to time an aspect of the application of the current responsively to the signal. For some applications, the feature includes an R-wave of an electrocardiogram (ECG) of subject, and the first control unit is adapted to generate the signal at each detection of the R-wave.

In an embodiment, the second control unit is adapted to, upon detection of suspected arrhythmia, drive the electrode device to apply the current, and to configure the current to reduce a ventricular rate. For some applications, the implantable sensor and the first control unit together include an implantable cardioverter defibrillator (ICD), and the ICD is adapted to apply defibrillation to the heart if the applied current does not sufficiently reduce the ventricular rate.

In an embodiment, the first control unit is adapted to detect ventricular fibrillation (VF), to generate a communication signal responsive to the detection, and to withhold generating the signal after the detection ceases; and the second control unit is adapted to receive the signal, and, responsively thereto, to withhold driving the electrode device to apply the current until cessation of the signal. For some applications, in the absence of detection of VF by the implantable device, the second control unit is adapted to continue driving the electrode device to apply the current notwithstanding any detection of ventricular tachycardia by the first control unit. For some applications, in the absence of detection of VF by the first control unit, the second control unit is adapted to continue driving the electrode device to apply the current notwithstanding any detection of supraventricular tachycardia by the first control unit.

In an embodiment, the second control unit is adapted to detect ventricular fibrillation (VF), and, responsively thereto, to withhold driving the electrode device to apply the current until cessation of the VF. For some applications, in the absence of detection of VF by the second control unit, the second control unit is adapted to continue driving the electrode device to apply the current notwithstanding any detection of ventricular tachycardia by the second control unit. For some applications, in the absence of detection of VF by the second control unit, the second control unit is adapted to continue driving the electrode device to apply the current notwithstanding any detection of supraventricular tachycardia by the second control unit.

In an embodiment, the first control unit is adapted to detect ventricular tachycardia (VT), to generate a communication signal responsive to the detection, and to withhold generating the signal after the detection ceases; and the second control unit is adapted to receive the signal, and, responsively thereto, to withhold driving the electrode device to apply the current until cessation of the signal. For some applications, in the absence of detection of VT by the first control unit, the second control unit is adapted to continue driving the electrode device to apply the current, notwithstanding any detection of non-ventricular-origin tachycardia by the first control unit. For some applications, in the absence of detection of VT by the first control unit, the second control unit is adapted to continue driving the electrode device to apply the current, notwithstanding any detection of supraventricular tachycardia by the first control unit.

In an embodiment, the second control unit is adapted to detect ventricular tachycardia (VT), and, responsively thereto, to withhold driving the electrode device to apply the current until cessation of the VT. For some applications, in the absence of detection of VT by the second control unit, the second control unit is adapted to continue driving the electrode device to apply the current, notwithstanding any detection of a non-ventricular-origin tachycardia by the second control unit. For some applications, in the absence of detection of VT by the second control unit, the second control unit is adapted to continue driving the electrode device to apply the current, notwithstanding any detection of supraventricular tachycardia by the second control unit.

In an embodiment, the first control unit is adapted to detect ventricular fibrillation (VF), to generate a communication signal responsive to the detection, and to withhold generating the signal after the detection ceases; the first control unit is adapted to detect ventricular tachycardia (VT), and generate the signal responsively to the detection, and to withhold generating the signal after the detection ceases; and the second control unit is adapted to receive the signal, and, responsively thereto, to withhold driving the electrode device to apply the current until cessation of the signal. For some applications, in the absence of detection of VF by the first control unit, and in the absence of detection of VT by the first control unit, the second control unit is adapted to continue driving the electrode device to apply the current notwithstanding any detection of a non-ventricular-origin tachycardia by the first control unit. For some applications, in the absence of detection of VF by the first control unit, and in the absence of detection of VT by the first control unit, the second control unit is adapted to continue driving the electrode device to apply the current notwithstanding detection of supraventricular tachycardia by the first control unit.

In an embodiment, the second control unit is adapted to detect ventricular fibrillation (VF), and, responsively thereto, to withhold driving the electrode device to apply the current until cessation of the VF; and the second control unit is adapted to detect ventricular tachycardia (VT), and, responsively thereto, to withhold driving the electrode device to apply the current until cessation of the VT. For some applications, in the absence of detection of VF by the second control unit, and in the absence of detection of VT by the second control unit, the second control unit is adapted to continue driving the electrode device to apply the current notwithstanding any detection of a non-ventricular-origin tachycardia by the second control unit. For some applications, in the absence of detection of VF by the second control unit, and in the absence of detection of VT by the second control unit, the second control unit is adapted to continue driving the electrode device to apply the current notwithstanding detection of supraventricular tachycardia by the second control unit.

In an embodiment, the first control unit is adapted to generate a communication signal when applying pulses to the heart, and to withhold generating the signal when not applying the pulses; and the second control unit is adapted to receive the signal, and, responsively thereto, to withhold driving the electrode device to apply the current until a certain amount of time after cessation of the signal.

In an embodiment, the second control unit is adapted to drive the electrode device to apply the current during at least one period selected from the list consisting of: a refractory period of the heart, and a blanking period of the first control unit. For some applications, the second control unit is adapted to drive the electrode device to apply the current during at least a portion of a period beginning upon detection of a QRS complex and ending 100 milliseconds after the detection of the QRS complex.

In an embodiment, the first control unit is adapted to apply the pulses only when the heart rate is within a first set of values, and the second control unit is adapted to drive the electrode device to apply the current only when the heart rate is within a second set of values. For some applications, the first and second sets of values are non-overlapping. For some applications, the first set of values includes values greater than 190 beats per minute and less than 60 beats per minute, and the second set of values includes values between 70 and 180 beats per minute.

There is further provided, in accordance with an embodiment of the present invention, apparatus for classifying an arrhythmia including:

an implantable sensor adapted to sense an electrical parameter of a heart of a subject;

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and a control unit, adapted to:

detect an occurrence of arrhythmia responsively to the sensed electrical parameter, upon detecting the occurrence of the arrhythmia, drive the electrode device to apply a current to the site that increases parasympathetic tone of the subject, determine whether the applied current affects a physiological parameter selected from the list consisting of: heart rate and heart rate variability, and responsively to a determination that the applied current affects the physiological parameter, determine that the arrhythmia is not of ventricular origin.

For some applications, the control unit is adapted to determine that the arrhythmia is neither VT nor ventricular fibrillation (VF).

For some applications, the apparatus includes an implantable cardioverter defibrillator (ICD), of which the implantable sensor is a component.

For some applications, the physiological parameter includes the heart rate, and the control unit is adapted to determine whether the applied current affects the heart rate. For some applications, the control unit is adapted to configure the current to attempt to lower the heart rate.

For some applications, the physiological parameter includes the heart rate variability, and the control unit is adapted to determine whether the applied current affects the heart rate variability. For some applications, the control unit is adapted to configure the current to attempt to lower the heart rate variability.

There is additionally provided, in accordance with an embodiment of the present invention, apparatus including:

an implantable sensor, adapted to sense an electrical parameter of a heart of a subject;

a first control unit, adapted to apply cardiac resynchronization therapy (CRT) pulses to the heart responsively to the sensed parameter;

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and a second control unit, adapted to drive the electrode device to apply to the site a current that increases parasympathetic tone of the subject and increases an AV delay of the subject.

There is yet additionally provided, in accordance with an embodiment of the present invention, apparatus including:

an implantable cardioverter defibrillator (ICD), configured to apply therapeutic pulses to a heart of a subject upon detection of ventricular arrhythmia;

an electrode device, adapted to be coupled to a site of the subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and a control unit, adapted to drive the electrode device to apply to the site, upon the detection of the ventricular arrhythmia, a current that increases parasympathetic tone of the subject.

For some applications, the control unit is adapted to configure the current to reduce a heart rate of the subject. For some applications, the control unit is adapted to configure the current to prolong AV node delay. For some applications, the control unit is adapted to configure the current to increase heart rate variability.

There is still additionally provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

a sensing element, adapted to sense a physiological parameter of the subject; and a control unit, adapted to drive the electrode device to apply to the site a current that increases parasympathetic tone of the subject, and, responsively to the sensed physiological parameter, to configure the current to treat bundle branch block of the subject.

There is still further provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

a sensing element, adapted to sense a physiological parameter of a heart of the subject;

an implantable device adapted to apply pulses to the heart, the pulses selected from the list consisting of: pacing pulses and anti-arrhythmic energy; and a control unit, adapted to:
detect a life-threatening arrhythmia (LTA) responsively to the sensed physiological parameter,
responsively to the detection of the LTA, drive the electrode device to apply to the site a current that increases parasympathetic tone of the subject,
determine whether the LTA has been resolved,
responsively to a determination that the LTA has not been resolved, determine whether to drive the implantable device to apply the pulses to the heart,
responsively to an affirmative determination to drive the implantable device, drive the implantable device to apply the pulses to the heart, and
responsively to a determination not to drive the implantable device, drive the electrode device to apply the current to the site.

For some applications, the control unit is adapted to change a parameter of the current applied to the site, after the determination not to drive the implantable device.

For some applications, the implantable device includes an implantable cardioverter defibrillator (ICD). For some applications, the implantable device includes a pacemaker.

For some applications, the parameter includes a feature of an electrocardiogram (ECG) signal, and the sensing element is adapted to sense the feature.

For some applications, the control unit is adapted to determine to drive the implantable device to apply the pulses only if the control unit determines that only driving the electrode device to apply the current is unlikely to resolve the LTA.

There is also provided, in accordance with an embodiment of the present invention, apparatus including:

an electrode device, adapted to be coupled to a site of a subject selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

a sensing element, adapted to sense a physiological parameter of a heart of the subject;

an implantable device adapted to apply pulses to the heart, the pulses selected from the list consisting of: pacing pulses and anti-arrhythmic energy; and a control unit, adapted to:
drive the electrode device to apply to the site a current that increases parasympathetic tone of the subject,
detect a life-threatening arrhythmia (LTA) responsively to the sensed physiological parameter,
responsively to the detection of the LTA, modify at least one current parameter of the applied current,
determine whether the LTA has been resolved,
responsively to a determination that the LTA has not been resolved, determine whether to drive the implantable device to apply the pulses to the heart,
responsively to an affirmative determination to drive the implantable device, drive the implantable device to apply the pulses to the heart, and
responsively to a determination not to drive the implantable device, modify one or more current parameters of the applied current.

For some applications, the implantable device includes an implantable cardioverter defibrillator (ICD). For some applications, the implantable device includes a pacemaker.

For some applications, the parameter includes a feature of an electrocardiogram (ECG) signal, and the sensing element is adapted to sense the feature.

For some applications, the control unit is adapted to determine to drive the implantable device to apply the pulses only if the control unit determines that only driving the electrode device to apply the current is unlikely to resolve the LTA.

There is further provided, in accordance with an embodiment of the present invention, a method including:

sensing, from within a body of a subject, an electrical parameter of a heart of the subject;

applying, from a first implantation site within the body, pulses to the heart responsive to the parameter, the pulses selected from the list consisting of: pacing pulses and anti-arrhythmic energy;

applying, at a second implantation site within the body, a current that increases parasympathetic tone of the subject and affects a heart rate of the subject, the second implantation site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and coordinating an aspect of applying the pulses with an aspect of applying the current, without providing a controller that regulates both the applying of the pulses and the applying of the current.

For some applications, sensing the electrical parameter includes implanting, in the subject, a device for sensing the electrical parameter, and applying the pulses includes applying the pulses from the device.

There is still further provided, in accordance with an embodiment of the present invention, a method for classifying an arrhythmia including:

sensing an electrical parameter of a heart of a subject;

detecting an occurrence of arrhythmia responsively to the sensed electrical parameter;

upon detecting the occurrence of the arrhythmia, applying to a site of the subject a current that increases parasympathetic tone of the subject, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

determining whether the applied current affects a physiological parameter selected from the list consisting of: heart rate and heart rate variability; and responsively to a determination that the applied current affects the physiological parameter, determining that the arrhythmia is not of ventricular origin.

For some applications, determining that the arrhythmia is not ventricular tachycardia (VT) of ventricular origin includes determining that the arrhythmia is neither VT nor ventricular fibrillation (VF).

There is additionally provided, in accordance with an embodiment of the present invention, a method including:

implanting in a subject an implantable cardioverter defibrillator (ICD);

configuring the ICD to apply therapeutic pulses to a heart of the subject upon detection of ventricular arrhythmia; and upon the detection of the ventricular arrhythmia, applying to a site of the subject a current that increases parasympathetic tone of the subject, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject.

There is yet additionally provided, in accordance with an embodiment of the present invention, a method including:

sensing a physiological parameter of a subject;

applying to a site of the subject a current that increases parasympathetic tone of the subject, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject; and responsively to the sensed physiological parameter, configuring the current to treat bundle branch block of the subject.

There is also provided, in accordance with an embodiment of the present invention, a method for surgically implanting an electrode device in a vicinity of a nerve, including:

placing the electrode device around the nerve;

introducing conductive solution into the electrode device such that the solution is in contact with both the electrode device and the nerve;

during implantation of the electrode device, measuring an impedance between one or more electrodes of the electrode device and an electrical contact point in electrical communication with the electrode device; and responsively to the impedance measurement, determining whether the electrodes are positioned appropriately, and whether sufficient conductive solution is in the electrode device.

For some applications, the conductive solution includes saline solution, and introducing the conductive solution includes introducing the saline solution.

For some applications, the nerve includes a vagus nerve, and placing the electrode device around the nerve includes placing the electrode device around the vagus nerve.

For some applications, the method includes, responsively to the impedance measurement, determining whether the electrodes are correctly sized for the nerve. For some applications, determining whether the electrodes are positioned appropriately includes determining whether the electrodes are in good electrical contact with the nerve.

For some applications, determining whether the electrodes are positioned appropriately includes interpreting a value of the impedance measurement between 100 and 300 ohms as an indication that the electrodes are not positioned appropriately. For some applications, determining whether the electrodes are positioned appropriately includes interpreting a value of the impedance measurement between 300 and 1000 ohms as an indication that the electrodes are positioned appropriately. For some applications, determining whether sufficient conductive solution is in the electrode device includes interpreting a value of the impedance measurement greater than 1000 ohms as an indication that insufficient conductive solution is in the electrode device.

For some applications, the one or more electrodes of the electrode device include at least first and second electrodes, the electrical contact point includes the first one of the electrodes, and measuring the impedance includes measuring the impedance between the first and second electrodes.

For some applications, the electrical contact point is located outside of the electrode device, and measuring the impedance includes measuring the impedance between the one or more electrodes and the electrical contact point located outside of the electrode device.

There is further provided, in accordance with an embodiment of the present invention, a method including:

sensing, from within a body of a subject, a physiological parameter of a heart of the subject;

detecting a life-threatening arrhythmia (LTA) responsively to the sensed physiological parameter;

responsively to the detection of the LTA, applying to a site of the subject a current that increases parasympathetic tone of the subject, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

determining whether the LTA has been resolved;

responsively to a determination that the LTA has not been resolved, determining whether to apply, from within the body, pulses to the heart selected from the list consisting of: pacing pulses and anti-arrhythmic energy;

responsively to an affirmative determination to apply the pulses, applying the pulses to the heart; and responsively to a determination not to apply the pulses, applying the current to the site.

There is additionally provided, in accordance with an embodiment of the present invention, a method including:

applying to a site of a subject a current that increases parasympathetic tone of the subject, the site selected from the list consisting of: a vagus nerve of the subject, an epicardial fat pad of the subject, a pulmonary vein of the subject, a carotid artery of the subject, a carotid sinus of the subject, a coronary sinus of the subject, a vena cava vein of the subject, a right ventricle of the subject, and a jugular vein of the subject;

sensing, from within a body of the subject, a physiological parameter of a heart of the subject;

detecting a life-threatening arrhythmia (LTA) responsively to the sensed physiological parameter;

responsively to the detection of the LTA, modifying at least one current parameter of the applied current;

determining whether the LTA has been resolved;

responsively to a determination that the LTA has not been resolved, determining whether to apply, from within the body, pulses to the heart selected from the list consisting of: pacing pulses and anti-arrhythmic energy;

responsively to an affirmative determination to apply the pulses, applying the pulses to the heart; and responsively to a determination not to apply the pulses, modifying one or more current parameters of the applied current.

The present invention will be more fully understood from the following detailed description of embodiments thereof, taken together with the drawings, in which:

BRIEF DESCRIPTION OF THE DRAWINGS

FIG. 2C is a simplified perspective illustration of the electrode device of FIG. 2A, in accordance with an embodiment of the present invention;

FIGS. 7 and 8 are flow charts that schematically illustrate respective methods for treating life-threatening arrhythmia (LTA), in accordance with respective embodiments of the present invention.

DETAILED DESCRIPTION OF EMBODIMENTS

Figure 1:
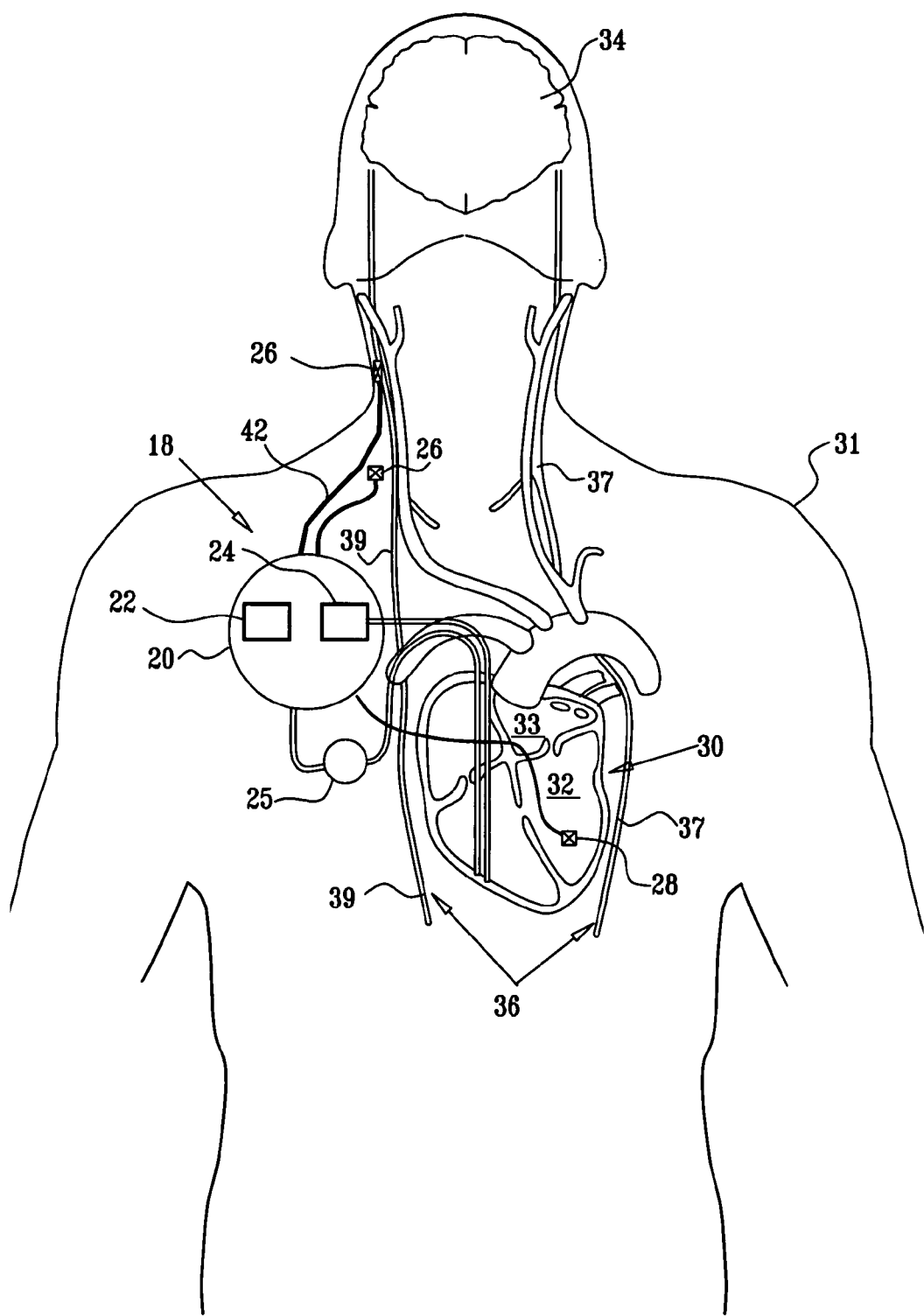
FIG. 1 is a block diagram that schematically illustrates a vagal stimulation system applied to a vagus nerve of a subject, in accordance with an embodiment of the present invention.

FIG. 1 is a block diagram that schematically illustrates a vagal stimulation system 18 comprising a multipolar electrode device 26, in accordance with an embodiment of the present invention. Electrode device 26 is applied to a portion of a vagus nerve 36 (a left vagus nerve 37 and/or a right vagus nerve 39), which innervates a heart 30 of a subject 31. Alternatively, electrode device 26 is applied to an epicardial fat pad, a pulmonary vein, a carotid artery, a carotid sinus, a coronary sinus, a vena cava vein, a right ventricle, or a jugular vein (configurations not shown). Typically, system 18 is utilized for treating a heart condition such as heart failure and/or cardiac arrhythmia. Vagal stimulation system 18 further comprises an implantable or external control unit 20, which typically communicates with electrode device 26 over a set of leads 42. Typically, control unit 20 drives electrode device 26 to (i) apply signals to induce the propagation of efferent nerve impulses towards heart 30, and (ii) suppress artificially-induced afferent nerve impulses towards a brain 34 of the subject, in order to minimize unintended side effects of the signal application. The efferent nerve pulses in vagus nerve 36 are typically induced by electrode device 26 in order to regulate the heart rate of the subject.

For some applications, control unit 20 is adapted to receive feedback from one or more of the electrodes in electrode device 26, and to regulate the signals applied to the electrode device responsive thereto.

Control unit 20 is typically adapted to receive and analyze one or more sensed physiological parameters or other parameters of the subject, such as heart rate, electrocardiogram (ECG), blood pressure, indicators of decreased cardiac contractility, cardiac output, norepinephrine concentration, left ventricular end diastolic pressure (LVEDP), or motion of the subject. In order to receive these sensed parameters, control unit 20 may comprise, for example, an ECG monitor 24, connected to a site on the subject's body such as heart 30, for example using one or more subcutaneous sensors or ventricular and/or atrial intracardiac sensors. The control unit may also comprise an accelerometer 22 for detecting motion of the subject. Alternatively, ECG monitor 24 and/or accelerometer 22 comprise separate implanted devices placed external to control unit 20, and, optionally, external to the subject's body. Alternatively or additionally, control unit 20 receives signals from one or more physiological sensors 28, such as blood pressure sensors. Sensors 28 are typically implanted in the subject, for example in a left ventricle 32 of heart 30. For example, sensors 28 may comprise a pressure gauge for measuring LVEDP, which gauge may be adapted to be placed in left ventricle 32, a left atrium 33 of heart 30, or in a pulmonary artery.

Figure 2A:
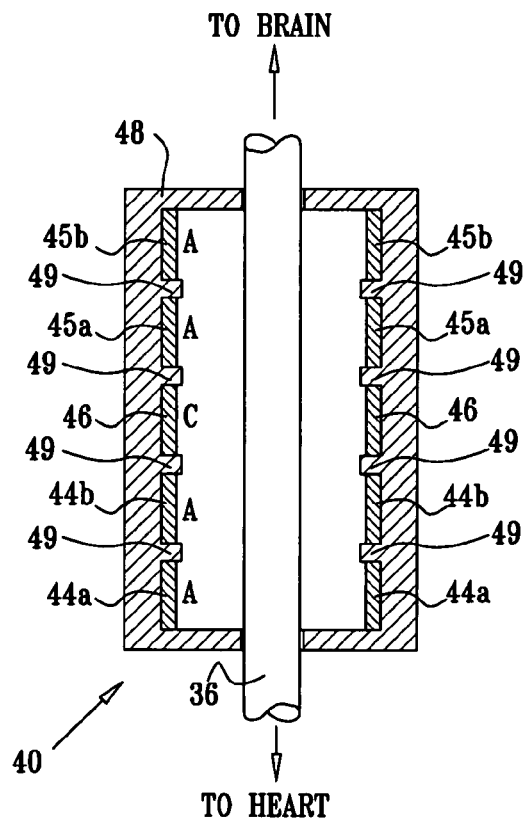
FIG. 2A is a simplified cross-sectional illustration of a multipolar electrode device applied to a vagus nerve, in accordance with an embodiment of the present invention.

FIG. 2A is a simplified cross-sectional illustration of a generally-cylindrical electrode device 40 applied to vagus nerve 36, in accordance with an embodiment of the present invention. For some applications, electrode device 26 (FIG. 1) comprises electrode device 40. Alternatively, electrode device 26 comprises an electrode device known in the art of nerve stimulation, such as those described in some of the references incorporated herein by reference. Electrode device 40 comprises a central cathode 46 for applying a negative current ("cathodic current") in order to stimulate vagus nerve 36, as described below. Electrode device 40 additionally comprises a set of one or more anodes 44 (44a, 44b, herein: "efferent anode set 44"), placed between cathode 46 and the edge of electrode device 40 closer to heart 30 (the "efferent edge"). Efferent anode set 44 applies a positive current ("efferent anodal current") to vagus nerve 36, for blocking action potential conduction in vagus nerve 36 induced by the cathodic current, as described below. Typically, electrode device 40 comprises an additional set of one or more anodes 45 (45a, 45b, herein: "afferent anode set 45"), placed between cathode 46 and the edge of electrode device 40 closer to brain 34. Afferent anode set 45 applies a positive current ("afferent anodal current") to vagus nerve 36, in order to block propagation of action potentials in the direction of the brain during application of the cathodic current.

For some applications, the one or more anodes of efferent anode set 44 are directly electrically coupled to the one or more anodes of afferent anode set 45, such as by a common wire or shorted wires providing current to both anode sets substantially without any intermediary elements. Typically, coatings on the anodes, shapes of the anodes, positions of the anodes, sizes of the anodes and/or distances of the various anodes from the nerve are regulated so as to produce desired ratios of currents and/or desired activation functions delivered through or caused by the various anodes. For example, by varying one or more of these characteristics, the relative impedance between the respective anodes and central cathode 46 is regulated, whereupon more anodal current is driven through the one or more anodes having lower relative impedance. In these applications, central cathode 46 is typically placed closer to one of the anode sets than to the other, for example, so as to induce asymmetric stimulation (i.e., not necessarily unidirectional in all fibers) between the two sides of the electrode device. The closer anode set typically induces a stronger blockade of the cathodic stimulation.

Figure 2B:
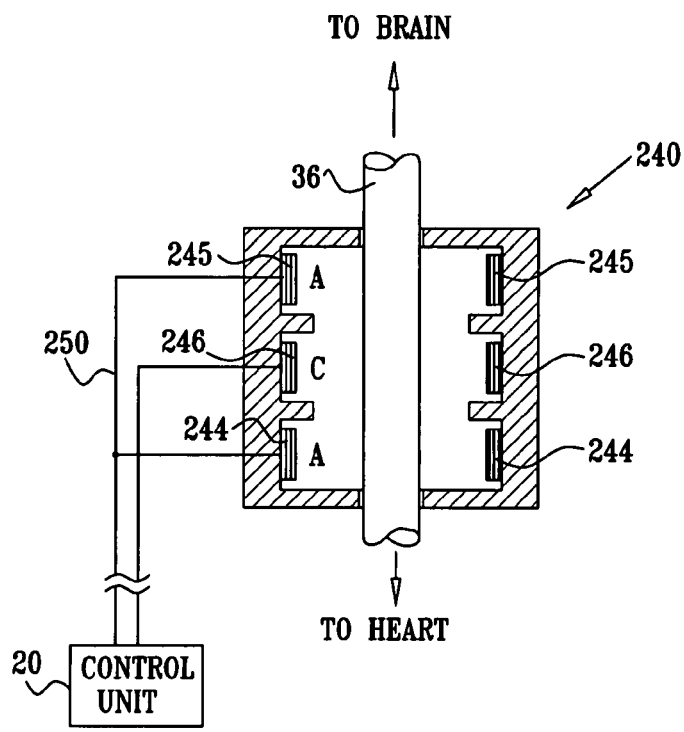
FIG. 2B is a simplified cross-sectional illustration of a generally-cylindrical electrode device applied to a vagus nerve, in accordance with an embodiment of the present invention.

Reference is now made to FIG. 2B, which is a simplified cross-sectional illustration of a generally-cylindrical electrode device 240 applied to vagus nerve 36, in accordance with an embodiment of the present invention. Electrode device 240 comprises exactly one efferent anode 244 and exactly one afferent anode 245, which are electrically coupled to each other, such as by a common wire 250 or shorted wires providing current to both anodes 244 and 245, substantially without any intermediary elements. The cathodic current is applied by a cathode 246 with an amplitude sufficient to induce action potentials in large- and medium-diameter fibers (e.g., A- and B-fibers), but insufficient to induce action potentials in small-diameter fibers (e.g., C-fibers).

Reference is again made to FIG. 2A. Cathodes 46 and anode sets 44 and 45 (collectively, "electrodes") are typically mounted in an electrically-insulating cuff 48 and separated from one another by insulating elements such as protrusions 49 of the cuff. Typically, the width of the electrodes is between about 0.5 and about 2 millimeters, or is equal to approximately one-half the radius of the vagus nerve. The electrodes are typically recessed so as not to come in direct contact with vagus nerve 36. For some applications, such recessing enables the electrodes to achieve generally uniform field distributions of the generated currents and/or generally uniform values of the activation function defined by the electric potential field in the vicinity of vagus nerve 24. Alternatively or additionally, protrusions 49 allow vagus nerve 24 to swell into the canals defined by the protrusions, while still holding the vagus nerve centered within cuff 48 and maintaining a rigid electrode geometry. For some applications, cuff 48 comprises additional recesses separated by protrusions, which recesses do not contain active electrodes. Such additional recesses accommodate swelling of vagus nerve 24 without increasing the contact area between the vagus nerve and the electrodes.

For some applications, the distance between the electrodes and the axis of the vagus nerve is between about 1 and about 4 millimeters, and is greater than the closest distance from the ends of the protrusions to the axis of the vagus nerve. Typically, protrusions 49 are relatively short (as shown). For some applications, the distance between the ends of protrusions 49 and the center of the vagus nerve is between about 1 and 3 millimeters. (Generally, the diameter of the vagus nerve is between about 2 and 3 millimeters.) Alternatively, for some applications, protrusions 49 are longer and/or the electrodes are placed closer to the vagus nerve in order to reduce the energy consumption of electrode device 40.

In an embodiment of the present invention, efferent anode set 44 comprises a plurality of anodes 44, typically two anodes 44a and 44b, spaced approximately 0.5 to 2.0 millimeters apart. Application of the efferent anodal current in appropriate ratios from a plurality of anodes generally minimizes the "virtual cathode effect," whereby application of too large an anodal current stimulates rather than blocks fibers. In an embodiment, anode 44a applies a current with an amplitude equal to about 0.5 to about 5 milliamps (typically one-third of the amplitude of the current applied by anode 44b). When such techniques are not used, the virtual cathode effect generally hinders blocking of smaller-diameter fibers, as described below, because a relatively large anodal current is generally necessary to block such fibers.

Anode 44a is typically positioned in cuff 48 to apply current at the location on vagus nerve 36 where the virtual cathode effect is maximally generated by anode 44b. For applications in which the blocking current through anode 44b is expected to vary substantially, efferent anode set 44 typically comprises a plurality of virtual-cathode-inhibiting anodes 44a, one or more of which is activated at any time based on the expected magnitude and location of the virtual cathode effect.

Likewise, afferent anode set 45 typically comprises a plurality of anodes 45, typically two anodes 45a and 45b, in order to minimize the virtual cathode effect in the direction of the brain. In certain electrode configurations, cathode 46 comprises a plurality of cathodes in order to minimize the "virtual anode effect," which is analogous to the virtual cathode effect.

FIG. 2C is a simplified perspective illustration of electrode device 40 (FIG. 2A), in accordance with an embodiment of the present invention. When applied to vagus nerve 36, electrode device 40 typically encompasses the nerve. As described, control unit 20 typically drives electrode device 40 to (i) apply signals to vagus nerve 36 in order to induce the propagation of efferent action potentials towards heart 30, and (ii) suppress artificially-induced afferent action potentials towards brain 34. The electrodes typically comprise ring electrodes adapted to apply a generally uniform current around the circumference of the nerve, as best shown in FIG. 2C.

Alternatively, ordinary, non-cuff electrodes are used, such as when the electrodes are placed on the epicardial fat pads instead of on the vagus nerve.

In an embodiment of the present invention, a method for surgically implanting electrode device 26 comprises: (a) placing the electrode device around vagus nerve 36, (b) during the implantation procedure, introducing conductive solution (e.g., saline solution) into the electrode device such that the solution is in contact with both the electrodes and the nerve, and (c) measuring an inter-electrode impedance during the implantation procedure. Such an impedance measurement enables the surgeon to determine during the procedure (a) whether the electrodes are positioned appropriately, (b) whether sufficient conductive solution has been introduced into and remained in electrode device 26, (c) whether the electrodes are the correct size for the nerve, and (d) whether the electrodes are in good contact with the nerve. Expected values for the impedance measurement, and their typical interpretations, include:

a low value, such as between about 100 and about 300 ohms, which typically occurs if the electrodes are in poor contact with the nerve, such as because the diameter of the electrode is larger than that of the nerve. When there is such poor contact, the electrodes are short-circuited by the conductive solution, resulting in the low impedance;

a high value, such as greater than about 1000 ohms, which typically occurs if electrode device 26 is not filled properly with conductive solution, which causes a disconnect between the electrodes and the nerve; or a medium value, such as between about 300 and about 1000 ohms, which indicates that the electrodes are in good contact with the nerve, so that most of the current travels through the nerve.

If the impedance differs from an expected value, the surgeon corrects the placement by, for example, repositioning the electrode device, removing the electrode device and implanting another electrode device having a different size, and/or introducing additional conductive solution into the electrode device. The techniques of this embodiment are also applicable to implanting electrode devices on a body tissue other than the vagus nerve.

Figure 3:
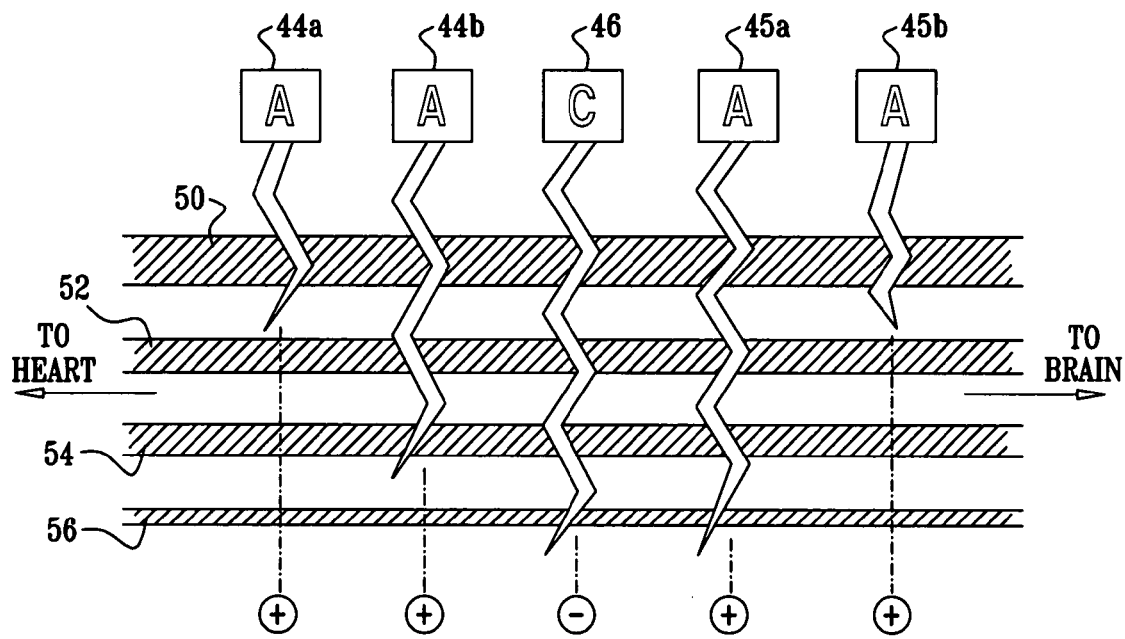
FIG. 3 is a conceptual illustration of the application of current to a vagus nerve, in accordance with an embodiment of the present invention.

FIG. 3 is a conceptual illustration of the application of current to vagus nerve 36 in order to achieve smaller-to-larger diameter fiber recruitment, in accordance with an embodiment of the present invention. When inducing efferent action potentials towards heart 30, control unit 20 drives electrode device 40 to selectively recruit nerve fibers beginning with smaller-diameter fibers and to progressively recruit larger-diameter fibers as the desired stimulation level increases. This smaller-to-larger diameter recruitment order mimics the body's natural order of recruitment.

Typically, in order to achieve this recruitment order, the control unit stimulates myelinated fibers essentially of all diameters using cathodic current from cathode 46, while simultaneously inhibiting fibers in a larger-to-smaller diameter order using efferent anodal current from efferent anode set 44. For example, FIG. 3 illustrates the recruitment of a single, smallest nerve fiber 56, without the recruitment of any larger fibers 50, 52 and 54. The depolarizations generated by cathode 46 stimulate all of the nerve fibers shown, producing action potentials in both directions along all the nerve fibers. Efferent anode set 44 generates a hyperpolarization effect sufficiently strong to block only the three largest nerve fibers 50, 52 and 54, but not fiber 56. This blocking order of larger-to-smaller diameter fibers is achieved because larger nerve fibers are inhibited by weaker anodal currents than are smaller nerve fibers. Stronger anodal currents inhibit progressively smaller nerve fibers. When the action potentials induced by cathode 46 in larger fibers 50, 52 and 54 reach the hyperpolarized region in the larger fibers adjacent to efferent anode set 44, these action potentials are blocked. On the other hand, the action potentials induced by cathode 46 in smallest fiber 56 are not blocked, and continue traveling unimpeded toward heart 30. Anode pole 44a is shown generating less current than anode pole 44b in order to minimize the virtual cathode effect in the direction of the heart, as described above.

When desired, in order to increase the parasympathetic stimulation delivered to the heart, the number of fibers not blocked is progressively increased by decreasing the amplitude of the current applied by efferent anode set 44. The action potentials induced by cathode 46 in the fibers now not blocked travel unimpeded towards the heart. As a result, the parasympathetic stimulation delivered to the heart is progressively increased in a smaller-to-larger diameter fiber order, mimicking the body's natural method of increasing stimulation. Alternatively or additionally, in order to increase the number of fibers stimulated, while simultaneously decreasing the average diameter of fibers stimulated, the amplitudes of the currents applied by cathode 46 and efferent anode set 44 are both increased (thereby increasing both the number of fibers stimulated and blocked). In addition, for any given number of fibers stimulated (and not blocked), the amount of stimulation delivered to the heart can be increased by increasing the PPT, frequency, and/or pulse width of the current applied to vagus nerve 36.

In order to suppress artificially-induced afferent action potentials from traveling towards the brain in response to the cathodic stimulation, control unit 20 typically drives electrode device 40 to inhibit fibers 50, 52, 54 and 56 using afferent anodal current from afferent anode set 45. When the afferent-directed action potentials induced by cathode 46 in all of the fibers reach the hyperpolarized region in all of the fibers adjacent to afferent anode set 45, the action potentials are blocked. Blocking these afferent action potentials generally minimizes any unintended side effects, such as undesired or counterproductive feedback to the brain, that might be caused by these action potentials. Anode 45b is shown generating less current than anode 45a in order to minimize the virtual cathode effect in the direction of the brain, as described above.

In an embodiment of the present invention, the amplitude of the cathodic current applied in the vicinity of the vagus nerve is between about 2 milliamps and about 10 milliamps. Such a current is typically used in embodiments that employ techniques for achieving generally uniform stimulation of the vagus nerve, i.e., stimulation in which the stimulation applied to fibers on or near the surface of the vagus nerve is generally no more than about 400% greater than stimulation applied to fibers situated more deeply in the nerve. This corresponds to stimulation in which the value of the activation function at fibers on or near the surface of the vagus nerve is generally no more than about four times greater than the value of the activation function at fibers situated more deeply in the nerve. For example, as described hereinabove with reference to FIG. 2A, the electrodes may be recessed so as not to come in direct contact with vagus nerve 24, in order to achieve generally uniform values of the activation function. Typically, but not necessarily, embodiments using approximately 5 mA of cathodic current have the various electrodes disposed approximately 0.5 to 2.5 mm from the axis of the vagus nerve. Alternatively, larger cathodic currents (e.g., 10-30 mA) are used in combination with electrode distances from the axis of the vagus nerve of greater than 2.5 mm (e.g., 2.5-4.0 mm), so as to achieve an even greater level of uniformity of stimulation of fibers in the vagus nerve.

In an embodiment of the present invention, the cathodic current is applied by cathode 46 with an amplitude sufficient to induce action potentials in large- and medium-diameter fibers 50, 52, and 54 (e.g., A- and B-fibers), but insufficient to induce action potentials in small-diameter fibers 56 (e.g., C-fibers). Simultaneously, an anodal current is applied by anode 44b in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked by anode 45a, as described above. Alternatively, the afferent anodal current is configured to not fully block afferent action potentials, or is simply not applied. In these cases, artificial afferent action potentials are nevertheless generally not generated in C-fibers, because the applied cathodic current is not strong enough to generate action potentials in these fibers.

These techniques for efferent stimulation of only B-fibers are typically used in combination with techniques described hereinabove for achieving generally uniform stimulation of the vagus nerve. Such generally uniform stimulation enables the use of a cathodic current sufficiently weak to avoid stimulation of C-fibers near the surface of the nerve, while still sufficiently strong to stimulate B-fibers, including B-fibers situated more deeply in the nerve, i.e., near the center of the nerve. For some applications, when employing such techniques for achieving generally uniform stimulation of the vagus nerve, the amplitude of the cathodic current applied by cathode 46 may be between about 3 and about 10 milliamps, and the amplitude of the anodal current applied by anode 44b may be between about 1 and about 7 milliamps. (Current applied at a different site and/or a different time is used to achieve a net current injection of zero.)

In an embodiment of the present invention, stimulation of the vagus nerve is applied responsive to one or more sensed parameters. Control unit 20 is typically configured to commence or halt stimulation, or to vary the amount and/or timing of stimulation in order to achieve a desired target heart rate, typically based on configuration values and on parameters including one or more of the following:

- Heart rate—the control unit can be configured to drive electrode device 26 to stimulate the vagus nerve only when the heart rate exceeds a certain value.
- ECG readings—the control unit can be configured to drive electrode device 26 to stimulate the vagus nerve based on certain ECG readings, such as readings indicative of designated forms of arrhythmia. Additionally, ECG readings are typically used for achieving a desire heart rate, as described below with reference to FIG. 4.
- Blood pressure—the control unit can be configured to regulate the current applied by electrode device 26 to the vagus nerve when blood pressure exceeds a certain threshold or falls below a certain threshold.
- Indicators of decreased cardiac contractility—these indicators include left ventricular pressure (LVP). When LVP and/or d(LVP)/dt exceeds a certain threshold or falls below a certain threshold, control unit 20 can drive electrode device 26 to regulate the current applied by electrode device 26 to the vagus nerve.
- Motion of the subject—the control unit can be configured to interpret motion of the subject as an indicator of increased exertion by the subject, and appropriately reduce parasympathetic stimulation of the heart in order to allow the heart to naturally increase its rate.
- Heart rate variability—the control unit can be configured to drive electrode device 26 to stimulate the vagus nerve based on heart rate variability, which is typically calculated based on certain ECG readings.
- Norepinephrine concentration—the control unit can be configured to drive electrode device 26 to stimulate the vagus nerve based on norepinephrine concentration.
- Cardiac output—the control unit can be configured to drive electrode device 26 to stimulate the vagus nerve based on cardiac output, which is typically determined using impedance cardiography.
- Baroreflex sensitivity—the control unit can be configured to drive electrode device 26 to stimulate the vagus nerve based on baroreflex sensitivity.
- LVEDP—the control unit can be configured to drive electrode device 26 to stimulate the vagus nerve based on LVEDP, which is typically determined using a pressure gauge, as described hereinabove with reference to FIG. 1.

The parameters and behaviors included in this list are for illustrative purposes only, and other possible parameters and/or behaviors will readily present themselves to those skilled in the art, having read the disclosure of the present patent application.

In an embodiment of the present invention, control unit 20 is configured to drive electrode device 26 to stimulate the vagus nerve so as to reduce the heart rate of the subject towards a target heart rate. The target heart rate is typically (a) programmable or configurable, (b) determined responsive to one or more sensed physiological values, such as those described hereinabove (e.g., motion, blood pressure, etc.), and/or (c) determined responsive to a time of day or circadian cycle of the subject. Parameters of stimulation are varied in real time in order to vary the heart-rate-lowering effects of the stimulation. For example, such parameters may include the amplitude of the applied current. Alternatively or additionally, in an embodiment of the present invention, the stimulation is applied in bursts (i.e., series of pulses), which are synchronized or are not synchronized with the cardiac cycle of the subject, such as described hereinbelow with reference to FIG. 4. Parameters of such bursts typically include, but are not limited to:

- Timing of the stimulation within the cardiac cycle. Delivery of each of the bursts typically begins after a fixed or variable delay following an ECG feature, such as each R- or P-wave. For some applications, the delay is between about 20 ms and about 700 ms after the R-wave (e.g., about 100 ms after the R-wave), or between about 100 and about 500 ms after the P-wave.
- Pulse duration (width). Longer pulse durations typically result in a greater heart-rate-lowering effect. For some applications, the pulse duration is between about 0.1 and about 4 ms, such as between about 100 microseconds and about 2.5 ms, e.g., about 1 ms.
- Pulse repetition interval within each burst. Maintaining a pulse repetition interval (the time from the initiation of a pulse to the initiation of the following pulse within the same burst) greater than about 3 ms generally results in maximal stimulation effectiveness for multiple pulses within a burst. For some applications, the pulse repetition interval is between about 1 and about 20 ms, such as between about 3 and about 10 ms, e.g., about 6 ms.
- Pulses per trigger (PPT). A greater PPT (the number of pulses in each burst after a trigger such as an R-wave) typically results in a greater heart-rate-lowering effect. For some applications, PPT is between about 0 and about 20 pulses, such as between about 1 and about 10 pulses, e.g., 3 pulses. For some applications, PPT is varied while pulse repetition interval is kept constant.
- Amplitude. A greater amplitude of the signal applied typically results in a greater heart-rate-lowering effect. The amplitude is typically less than about 20 milliamps, e.g., between about 0.1 and about 9 milliamps, e.g., about 2.5 milliamps. For some applications, the amplitude is between about 2 and about 6 milliamps.
- Duty cycle (number of bursts per heart beat). Application of stimulation every heartbeat (i.e., with a duty cycle of 1) typically results in a greater heart-rate-lowering effect. For less heart rate reduction, stimulation is applied less frequently than every heartbeat (e.g., duty cycle=60%-90%), or only once every several heartbeats (e.g., duty cycle=5%-40%).
- Choice of vagus nerve. Stimulation of the right vagus nerve typically results in greater heart rate reduction than stimulation of the left vagus nerve.
- "On"/"off" ratio and timing. For some applications, the device operates intermittently, alternating between "on" and "off" states, the length of each state typically being between 0 and about 1 day, such as between 0 and about 300 seconds (with a O-length "off" state equivalent to always "on"). No stimulation is applied during the "off" state. Greater heart rate reduction is typically achieved if the device is "on" a greater portion of the time.

For some applications, values of one or more of the parameters are determined in real time, using feedback, i.e., responsive to one or more inputs, such as sensed physiological values. For example, the intermittency ("on"/"off") parameter may be determined in real time using such feedback. The inputs used for such feedback typically include one or more of the following: (a) motion or activity of the subject (e.g., detected using an accelerometer), (b) the average heart rate of the subject, (c) the average heart rate of the subject when the device is in "off" mode, (d) the average heart rate of the subject when the device is in "on" mode, and/or (e) the time of day. The average heart rate is typically calculated over a period of at least about 10 seconds. For some applications, the average heart rate during an "on" or "off" period is calculated over the entire "on" or "off" period. For example, the device may operate in continuous "on" mode when the subject is exercising and therefore has a high heart rate, and the device may alternate between "on" and "off" when the subject is at rest. As a result, the heart-rate-lowering effect is concentrated during periods of high heart rate, and the nerve is allowed to rest when the heart rate is generally naturally lower. For some applications, the device determines the ratio of "on" to "off" durations, the duration of the "on" periods, and/or the durations of the "off" periods using feedback. Optionally, the device determines the "on"/"off" parameter in real time using the integral feedback techniques described hereinbelow, and/or other feedback techniques described hereinbelow, mutatis mutandis.

For some applications, heart rate regulation is achieved by setting two or more parameters in combination. For example, if it is desired to apply 5.2 pulses of stimulation, the control unit may apply 5 pulses of 1 ms duration each, followed by a single pulse of 0.2 ms duration. For other applications, the control unit switches between two values of PPT, so that the desired PPT is achieved by averaging the applied PPTs. For example, a sequence of PPTs may be 5, 5, 5, 5, 6, 5, 5, 5, 5, 6, . . . , in order to achieve an effective PPT of 5.2.

In an embodiment of the present invention, control unit 20 is configured to apply vagal stimulation using feedback, as described hereinabove, wherein a parameter of the feedback is a target heart rate that is a function of an average heart rate of the subject. For some applications, the target heart rate is set equal or approximately equal to the average heart rate of the subject. Alternatively, the target heart rate is set at a rate greater than the average heart rate of the subject, such as a number of beats per minute (BPM) greater than the average heart rate, or a percentage greater than the average heart rate, e.g., about 1% to about 50% greater. Further alternatively, the target heart rate is set at a rate less than the average heart rate of the subject, such as a number of BPM less than the average heart rate, or a percentage less than the average heart rate, e.g., about 1% to about 20% less. For some applications, the target heart rate is set responsively to the duty cycle and the heart rate response of the subject. In an embodiment, control unit 20 determines the target heart rate in real time, periodically or substantially continuously, by sensing the heart rate of the subject and calculating the average heart rate of the subject. The average heart rate is typically calculated substantially continuously, or periodically. Typically, standard techniques are used for calculating the average, such as moving averages or IIR filters. The number of beats that are averaged typically varies between several beats to all beats during the past week.

In an embodiment of the present invention, control unit 20 is configured to apply the bursts using short "on" periods and, optionally, short "off" periods. Each of the short "on" periods typically has a duration of less than about 10 seconds, e.g., less than about 5 seconds. When short "off" periods are used, each of the "off" periods typically has a duration of between about 5 and about 10 seconds. For example, the "on" periods may have a duration of about 3 seconds, and the "off" periods may have a duration of about 6 seconds. (Stimulation having the configuration described in this paragraph is referred to hereinbelow as "fast intermittent stimulation.") The use of such short periods generally allows stimulation of any given strength (e.g., as measured by amplitude of the signal, or by PPT of the signal) to be applied as effectively as when using longer "on"/"off" periods, but with fewer potential side effects. In addition, the use of such short "on" periods generally allows side-effect-free application of stimulation at a strength that might increase the risk of side effects if applied for longer "on" periods. It is believed by the inventors that the use of such short periods generally reduces side effects by preventing build-up of sympathetic tone. In general, the parasympathetic reaction to vagal stimulation occurs more quickly than the sympathetic reaction to vagal stimulation. The short "on" periods are sufficiently long to stimulate a desired meaningful parasympathetic reaction, but not sufficiently long to stimulate an undesired, potentially side-effect-causing sympathetic reaction.

In an experiment performed in accordance with a preferred embodiment of the present invention, vagal stimulation was applied to a dog using two sets of stimulation parameters, and side effects were monitored. The first set of stimulation parameters included continuous stimulation (i.e., stimulation every heart beat, without "on" and "off" periods), an amplitude of 6 milliamps, and a PPT of 2. Stimulation using this first set of parameters induced cough in the dog. The second set of stimulation parameters included "on" periods of 3 seconds and "off" periods of 6 seconds, an amplitude of 6 milliamps, and a PPT of 6. Stimulation with this second set of parameters did not induce cough in the dog. Both sets of parameters delivered the same amount of total stimulation, as expressed by current*pulses over any time period including an equal number of "on" and "off" periods.

For some applications, a desired number of pulses per time period or per heart beat is delivered more effectively and/or with a reduced risk of side effects, by using short "on" periods. For example, assume that it is desired to apply one pulse per trigger. Without the use of short "on" periods, one pulse per trigger could be achieved by applying one PPT constantly. Using short "on" periods, one pulse per trigger could instead be achieved by applying 3 PPT for 3 heart beats (the "on" period), followed by an "off" period of 6 heart beats without stimulation. In both cases, in any given 9-heart-beat period, the same number of pulses (9) are applied. However, the use of short "on" periods generally increases the effectiveness and reduces the potential side effects of the stimulations.

In an embodiment of the present invention, control unit 20 is configured to apply vagal stimulation in alternating short "high" stimulation and short "low" stimulation periods. Stimulation is applied with a greater strength during the "high" periods than during the "low" periods. "Low" strength, as used herein, including the claims, is to be understood as not including zero strength, i.e., as excluding the non-application of stimulation. Each of the short "high" periods typically has a duration of less than about 30 seconds (e.g., less than about 5 seconds), and each of the short "low" periods typically has a duration of less than about 30 seconds (e.g., less than about 5 seconds). For some applications, the "high" stimulation periods have a greater PPT than the "low" stimulation periods. Alternatively or additionally, the "high" stimulation periods have a greater amplitude than the "low" stimulation periods. Further alternatively or additionally, control unit 20 adjusts one or more of the other parameters described herein in order to apply the "high" stimulation periods with a greater strength than the "low" stimulation periods.

In an embodiment of the present invention, control unit 20 is configured to apply vagal stimulation intermittently using "on"/"off" periods, the durations of which are expressed in heart beats, rather than in units of time. In other words, the control unit alternatingly applies the stimulation for a first number of heart beats, and withholds applying the stimulation for a second number of heart beats. For example, the control unit may alternatingly apply the stimulation for between about 1 and about 30 heart beats, and withhold applying the stimulation for between about 5 and about 300 heart beats. Expressing the duration of the "on"/"off" periods in heart beats results in a constant duty cycle (expressed as "on"/ ("on"+"off")), while expressing the duration in units of time results in a variable duty cycle. In addition, expressing the duration of the "on"/"off" periods in heart beats results in the duration of the "on" and "off" periods varying based on the heart rate (at higher heart rates, the "on" and "off" periods are shorter). Furthermore, expressing the duration of the "on"/"off" periods in heart beats tends to synchronize the stimulation with breathing, which is usually more rapid when the heart rate increases, such as during exercise.

For one particular application, the control unit alternatingly applies the stimulation for exactly one heart beat, and withholds applying the stimulation for exactly one heart beat, i.e., the control unit applies the stimulation every other heart beat. Expressing the duration of "on"/"off" periods in heart beats typically allows precise control of the amount of stimulation applied and the physiological parameter that is being modified, e.g., heart rate.

In an embodiment of the present invention, control unit 20 uses a slow-reacting heart rate regulation algorithm to modify heart-rate-controlling parameters of the stimulation, i.e., the algorithm varies stimulation parameters slowly in reaction to changes in heart rate. For example, in response to a sudden increase in heart rate, e.g., an increase from a target heart rate of 60 beats per minute (BPM) to 100 BPM over a period of only a few seconds, the algorithm slowly increases the stimulation level over a period of minutes. If the heart rate naturally returns to the target rate over this period, the stimulation levels generally do not change substantially before returning to baseline levels.

For example, the heart of a subject is regulated while the subject is inactive, such as while sitting. When the subject suddenly increases his activity level, such as by standing up or climbing stairs, the subject's heart rate increases suddenly. In response, the control unit adjusts the stimulation parameters slowly to reduce the subject's heart rate. Such a gradual modification of stimulation parameters allows the subject to engage in relatively stressful activities for a short period of time before his heart rate is substantially regulated, generally resulting in an improved quality of life.

In an embodiment of the present invention, control unit 20 is configured to apply vagal stimulation intermittently using "on"/"off" periods, the duration of one of which type of periods is expressed in heart beats, and of the other is expressed in units of time. For example, the duration of the "on" periods may be expressed in heart beats (e.g., 2 heart beats), and the duration of the "off" periods may be expressed in seconds (e.g., 2 seconds). In other words, in this example, the control unit alternatingly applies the stimulation for a number of heart beats, and withholds applying the stimulation for a number of seconds. For example, the control unit may alternatingly apply the stimulation for between about 1 and about 100 heart beats, and withhold applying the stimulation for between about 1 and about 100 seconds. Expressing the duration of the "on"/"off" periods in this manner results in an automatic reduction of the duty cycle as the heart rate increases, because, at higher heart rates, more heart beats occur during the "off" periods. As a result, stimulation is automatically reduced at higher rates, which may allow for increased activity and improved quality of life.

In an embodiment of the present invention, control unit 20 is adapted to detect bradycardia (i.e., that an average detected R-R interval exceeds a preset bradycardia limit), and to terminate heart rate regulation substantially immediately upon such detection, such as by ceasing vagal stimulation. Alternatively or additionally, the control unit uses an algorithm that reacts quickly to regulate heart rate when the heart rate crosses limits that are predefined (e.g., a low limit of 40 beats per minute (BPM) and a high limit of 140 BPM), or determined in real time, such as responsive to sensed physiological values.

In an embodiment of the present invention, control unit 20 is configured to operate intermittently. Typically, upon each resumption of operation, control unit 20 sets the stimulation parameters to those in effect immediately prior to the most recent cessation of operation. For some applications, such parameters applied upon resumption of operation are maintained without adjustment for a certain number of heartbeats (e.g., between about one and about ten), in order to allow the heart rate to stabilize after resumption of operation.

For some applications, control unit 20 is configured to operate intermittently with gradual changes in stimulation. For example, the control unit may operate according to the following "on"/"off" pattern: (a) "off" mode for 30 minutes, (b) a two-minute "on" period characterized by a gradual increase in stimulation so as to achieve a target heart rate, (c) a six-minute "on" period of feedback-controlled stimulation to maintain the target heart rate, and (d) a two-minute "on" period characterized by a gradual decrease in stimulation to return the heart rate to baseline. The control unit then repeats the cycle, beginning with another 30-minute "off" period.

In an embodiment of the present invention, control unit 20 is configured to operate in an adaptive intermittent mode. The control unit sets the target heart rate for the "on" period equal to a fixed or configurable fraction of the average heart rate during the previous "off" period, typically bounded by a preset minimum. For example, assume that for a certain subject the average heart rates during sleep and during exercise are 70 and 150 BPM, respectively. Further assume that the target heart rate for the "on" period is set at 70% of the average heart rate during the previous "off" period, with a minimum of 60 BPM. During sleep, stimulation is applied so as to produce a heart rate of MAX(60 BPM, 70% of 70 BPM)=60 BPM, and is thus applied with parameters similar to those that would be used in the simple intermittent mode described hereinabove. Correspondingly, during exercise, stimulation is applied so as to produce a heart rate of MAX(60 BPM, 70% of 150 BPM)=105 BPM.

In an embodiment of the present invention, a heart rate regulation algorithm used by control unit 20 has as an input a time derivative of the sensed heart rate. The algorithm typically directs the control unit to respond slowly to increases in heart rate and quickly to decreases in heart rate.

In an embodiment of the present invention, the heart rate regulation algorithm utilizes sensed physiological parameters for feedback. For some applications, the feedback is updated periodically by inputting the current heart rate. For some applications, such updating occurs at equally-spaced intervals. Alternatively, the feedback is updated by inputting the current heart rate upon each detection of a feature of the ECG, such as an R-wave. In order to convert non-fixed R-R intervals into a form similar to canonical fixed intervals, the algorithm adds the square of each R-R interval, thus taking into account the non-uniformity of the update interval, e.g., in order to properly analyze feedback stability using standard tools and methods developed for canonical feedback.

In an embodiment of the present invention, control unit 20 implements a detection blanking period, during which the control unit does not detect heart beats. In some instances, such non-detection may reduce false detections of heart beats. One or both of the following techniques are typically implemented:

Absolute blanking. An expected maximal heart rate is used to determine a minimum interval between expected heart beats. During this interval, the control unit does not detect heart beats, thereby generally reducing false detections. For example, the expected maximal heart rate may be 200 BPM, resulting in a minimal detection interval of 300 milliseconds. After detection of a beat, the control unit disregards any signals indicative of a beat during the next 300 milliseconds.

Stimulation blanking. During application of a stimulation burst, and for an interval thereafter, the control unit does not detect heart beats, thereby generally reducing false detections of stimulation artifacts as beats. For example, assume stimulation is applied with the following parameters: a PPT of 5 pulses, a pulse width of 1 ms, and a pulse repetition interval of 5 ms. The control unit disregards any signals indicative of a beat during the entire 25 ms duration of the burst and for an additional interval thereafter, e.g., 50 ms, resulting in a total blanking period of 75 ms beginning with the start of the burst.

In an embodiment of the present invention, the heart rate regulation algorithm is implemented using only integer arithmetic. For example, division is implemented as integer division by a power of two, and multiplication is always of two 8-bit numbers. For some applications, time is measured in units of $1/128$ of a second.

In an embodiment of the present invention, control unit 20 implements an integral feedback controller, which can most generally be described by:

$$K = K_I * \int e \, dt$$

in which K represents the strength of the feedback, $K_I$ is a coefficient, and $\int e \, dt$ represents the cumulative error. It is to be understood that such an integral feedback controller can be implemented in hardware, or in software running in control unit 20.

In an embodiment of such an integral controller, heart rate is typically expressed as an R-R interval (the inverse of heart rate). Parameters of the integral controller typically include TargetRR (the target R-R interval) and TimeCoeff (which determines the overall feedback reaction time).

Typically, following the detection of each R-wave, the previous R-R interval is calculated and assigned to a variable (LastRR). e (i.e., the difference between the target R-R interval and the last measured R-R interval) is then calculated as:

$$e = \text{TargetRR} - \text{LastRR}$$

e is typically limited by control unit 20 to a certain range, such as between −0.25 and +0.25 seconds, by reducing values outside the range to the endpoint values of the range. Similarly, LastRR is typically limited, such as to 255/128 seconds. The error is then calculated by multiplying LastRR by e:

$$\text{Error} = e * \text{LastRR}$$

A cumulative error (representing the integral in the above generalized equation) is then calculated by dividing the error by TimeCoeff and adding the result to the cumulative error, as follows:

$$\text{Integral} = \text{Integral} + \text{Error}/2^{\text{TimeCoeff}}$$

The integral is limited to positive values less than, e.g., 36,863. The number of pulses applied in the next series of pulses (pulses per trigger, or PPT) is equal to the integral/4096.

The following table illustrates example calculations using a heart rate regulation algorithm that implements an integral controller, in accordance with an embodiment of the present invention. In this example, the parameter TargetRR (the target heart rate) is set to 1 second (128/128 seconds), and the parameter TimeCoeff is set to 0. The initial value of Integral is 0. As can be seen in the table, the number of pulses per trigger (PPT) increases from 0 during the first heart beat, to 2 during the fourth heart beat of the example.

|  | Heart Beat Number | | | |
| --- | --- | --- | --- | --- |
|  | 1 | 2 | 3 | 4 |
| Heart rate (BPM) | 100 | 98 | 96 | 102 |
| R-R interval (ms) | 600 | 610 | 620 | 590 |
| R-R (1/128 sec) | 76 | 78 | 79 | 75 |
| e (1/128 sec) | 52 | 50 | 49 | 53 |
| Limited e | 32 | 32 | 32 | 32 |
| Error | 2432 | 2496 | 2528 | 2400 |
| Integral | 2432 | 4928 | 7456 | 9856 |
| PPT | 0 | 1 | 1 | 2 |

In an embodiment of the present invention, the heart rate regulation algorithm corrects for missed heart beats (either of physiological origin or because of a failure to detect a beat). Typically, to perform this correction, any R-R interval which is about twice as long as the immediately preceding R-R interval is interpreted as two R-R intervals, each having a length equal to half the measured interval. For example, the R-R interval sequence (measured in seconds) 1, 1, 1, 2.2 is interpreted by the algorithm as the sequence 1, 1, 1, 1.1, 1.1. Alternatively or additionally, the algorithm corrects for premature beats, typically by adjusting the timing of beats that do not occur approximately halfway between the preceding and following beats. For example, the R-R interval sequence (measured in seconds) 1, 1, 0.5, 1.5 is interpreted as 1, 1, 1, 1, using the assumption that the third beat was premature.

In an embodiment of the present invention, control unit 20 is configured to operate in one of the following modes:

vagal stimulation is not applied when the heart rate of the subject is lower than the low end of the normal range of a heart rate of the subject and/or of a typical human subject;

vagal stimulation is not applied when the heart rate of the subject is lower than a threshold value equal to the current low end of the range of the heart rate of the subject, i.e., the threshold value is variable over time as the low end generally decreases as a result of chronic vagal stimulation treatment;

vagal stimulation is applied only when the heart rate of the subject is within the normal of range of a heart rate of the subject and/or of a typical human subjects;

vagal stimulation is applied only when the heart rate of the subject is greater than a programmable threshold value, such as a rate higher than a normal rate of the subject and/or a normal rate of a typical human subject. This mode generally removes peaks in heart rate; or vagal stimulation is applied using fixed programmable parameters, i.e., not in response to any feedback, target heart rate, or target heart rate range. These parameters may be externally updated from time to time, for example by a physician.

In an embodiment of the present invention, the amplitude of the applied stimulation current is calibrated by fixing a number of pulses in the series of pulses (per cardiac cycle), and then increasing the applied current until a desired predetermined heart rate reduction is achieved. Alternatively, the current is calibrated by fixing the number of pulses per series of pulses, and then increasing the current to achieve a substantial reduction in heart rate, e.g., 40%.

In embodiments of the present invention in which vagal stimulation system 18 comprises implanted device 25 for monitoring and correcting the heart rate, control unit 20 typically uses measured parameters received from device 25 as additional inputs for determining the level and/or type of stimulation to apply. Control unit 20 typically coordinates its behavior with the behavior of device 25. Control unit 20 and device 25 typically share sensors 28 in order to avoid redundancy in the combined system.

Optionally, vagal stimulation system 18 comprises a patient override, such as a switch that can be activated by the subject using an external magnet. The override typically can be used by the subject to activate vagal stimulation, for example in the event of arrhythmia apparently undetected by the system, or to deactivate vagal stimulation, for example in the event of apparently undetected physical exertion.

Figure 4:
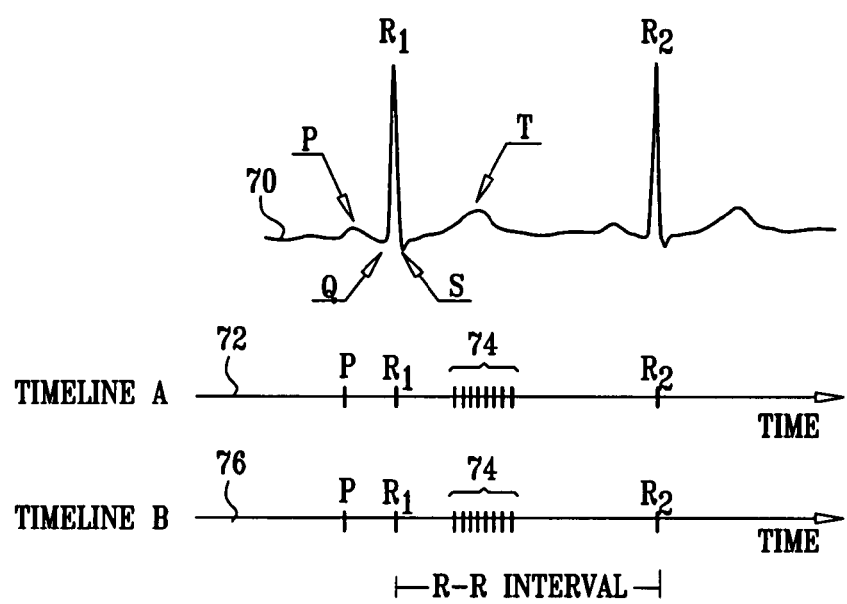
FIG. 4 is a simplified illustration of an electrocardiogram (ECG) recording and of example timelines showing the timing of the application of a series of stimulation pulses, in accordance with an embodiment of the present invention.

FIG. 4 is a simplified illustration of an ECG recording 70 and example timelines 72 and 76 showing the timing of the application of a burst of stimulation pulses 74, in accordance with an embodiment of the present invention. Stimulation is typically applied to vagus nerve 36 in a closed-loop system in order to achieve and maintain the desired target heart rate, determined as described above. Precise graded slowing of the heart beat is typically achieved by varying the number of nerve fibers stimulated, in a smaller-to-larger diameter order, and/or the intensity of vagus nerve stimulation, such as by changing the stimulation amplitude, pulse width, PPT, and/or delay. Stimulation with blocking, as described herein, is typically applied during each cardiac cycle in burst of pulses 74, typically containing between about 1 and about 20 pulses, each of about 1-3 milliseconds duration, over a period of about 1-200 milliseconds. Advantageously, such short pulse durations generally do not substantially block or interfere with the natural efferent or afferent action potentials traveling along the vagus nerve. Additionally, the number of pulses and/or their duration is sometimes varied in order to facilitate achievement of precise graded slowing of the heart beat.

In an embodiment of the present invention (e.g., when the heart rate regulation algorithm described hereinabove is not implemented), to apply the closed-loop system, the target heart rate is expressed as a ventricular R-R interval (shown as the interval between $R_1$ and $R_2$ in FIG. 4). The actual R-R interval is measured in real time and compared with the target R-R interval. The difference between the two intervals is defined as a control error. Control unit 20 calculates the change in stimulation necessary to move the actual R-R towards the target R-R, and drives electrode device 26 to apply the new calculated stimulation. Intermittently, e.g., every 1, 10, or 100 beats, measured R-R intervals or average R-R intervals are evaluated, and stimulation of the vagus nerve is modified accordingly.

In an embodiment, vagal stimulation system 18 is further configured to apply stimulation responsive to pre-set time parameters, such as intermittently, constantly, or based on the time of day.

Alternatively or additionally, one or more of the techniques of smaller-to-larger diameter fiber recruitment, selective fiber population stimulation and blocking, and varying the intensity of vagus nerve stimulation by changing the stimulation amplitude, pulse width, PPT, and/or delay, are applied in conjunction with methods and apparatus described in one or more of the patents, patent applications, articles and books cited herein.

In an embodiment of the present application, control unit 20 is configured to apply vagal stimulation when the heart rate of the subject is below a threshold value, in order to increase the heart rate. The threshold value is typically determined for each subject, e.g., based on the subject's hemodynamic needs and/or individual response to vagal stimulation. For example, for some subjects, the threshold value may be less than about 80 beats per minute, such as between 67 and 73 beats per minute. The threshold value is typically determined for each subject, e.g., based on the subject's hemodynamic needs and/or individual response to vagal stimulation. For some applications, the control unit is configured to apply fast intermittent stimulation, as defined hereinabove.

Figure 5:
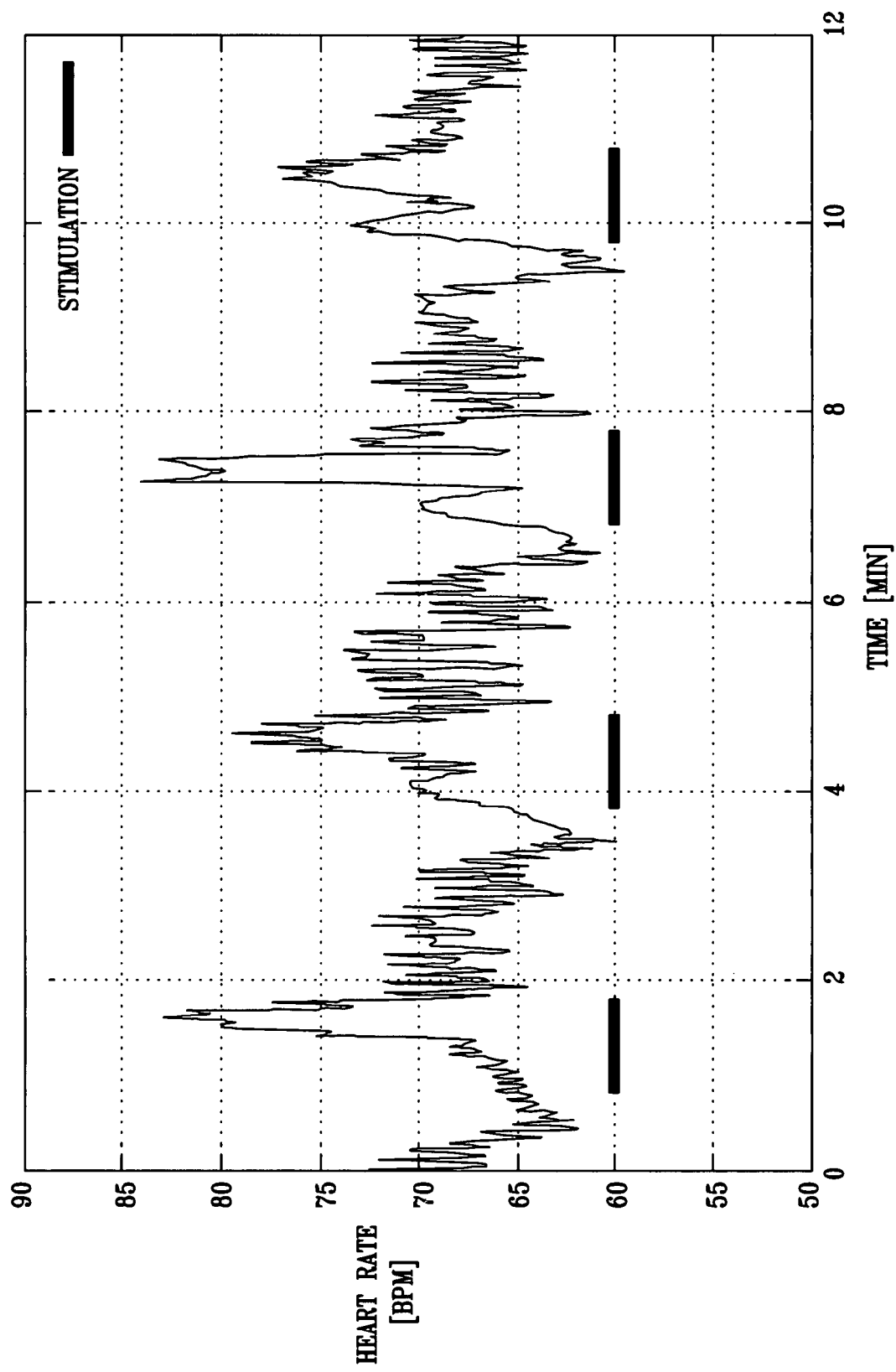
FIGS. 5 and 6 are graphs illustrating experimental results measured in accordance with an embodiment of the present invention.

FIG. 5 is a graph illustrating experimental results measured in accordance with an embodiment of the present invention. Vagal stimulation was applied to a conscious dog during alternating "on" and "off" periods having durations of 1 minute and 2 minutes, respectively. As can be seen in the graph, upon application of the vagal stimulation the heart rate increased substantially.

In an embodiment of the present invention, control unit 20 is configured to apply vagal stimulation (a) when the heart rate of the subject is above a first threshold value, in order to reduce the heart rate, and (b) when the heart rate is below a second threshold value, which is lower than the first threshold value, in order to increase the heart rate. Typically, the same stimulation is applied in both cases (a) and (b), and the stimulation has the desired decreasing or increasing effect depending upon the heart rate, without specific configuration based on the heart rate. The threshold values are typically determined for each subject, e.g., based on the subject's hemodynamic needs and/or individual response to vagal stimulation. For typical subjects, the first threshold value is generally greater than about 80 BPM, and the second threshold value is generally less than about 80 BPM. In addition to the heart-rate-lowering benefits described hereinabove, stimulation using the configuration of this embodiment generally has one or more of the following benefits: (a) maintenance of at least a minimal cardiac output, (b) improvements of the wellbeing of the subject when sleeping or at rest, (c) prevention of nocturnal dyspnea and polyuria, and (d) blood pressure regulation.

In an embodiment of the present invention, control unit 20 is configured to apply vagal stimulation having a strength that is inversely related, e.g., inversely proportional, to a heart rate of the subject, i.e., as the heart rate increases, the strength of the stimulation is decreased. For some applications, the control unit withholds applying the vagal stimulation when the heart rate exceeds a threshold value. The threshold value, and the relationship between the strength of stimulation and the heart rate, are typically determined for each subject, e.g., based on the subject's hemodynamic needs and/or individual response to vagal stimulation. For typical subjects, the threshold value is generally greater than about 50 BPM. For some applications, the threshold value is set at a rate less than an average heart rate of the subject, such as calculated by the control unit, or by a healthcare worker and input into the control unit. For example, the threshold value may be set at a number of BPM less than the average heart rate, or a percentage less than the average heart rate, e.g., about 1% to about 40% less. Alternatively, the threshold value is set equal to the average heart rate minus a certain number of standard deviations. For some applications, such stimulation is applied during sleep, e.g., only or mostly during sleep. For some applications, a sleeping period of the patient is determined by an accelerometer, electroencephalogram (EEG), or a clock.

Such a configuration generally results in the beneficial effects of vagal stimulation that are not necessarily dependent on the heart-rate reduction effects of such stimulation. (See the above-cited article by Vanoli E et al.) Such a configuration generally also results in an improved quality of life for the subject, because the heart rate is allowed to increase to meet the subject's physiological demands.

Such vagal stimulation is generally useful for treating conditions such as AF, heart failure, atherosclerosis, restenosis, myocarditis, cardiomyopathy, post-myocardial infarct remodeling, and hypertension. In addition, such treatment is believed by the inventors to reduce the risk of sudden cardiac death in some patients (such as those with hypertrophic cardiomyopathy or congenital long QT syndrome). Furthermore, such treatment is believed by the inventors to be beneficial for the treatment of some non-cardiovascular conditions, such as an autoimmune disease, an autoimmune inflammatory disease, multiple sclerosis, encephalitis, myelitis, immune-mediated neuropathy, myositis, dermatomyositis, polymyositis, inclusion body myositis, inflammatory demyelinating polyradiculoneuropathy, Guillain Barre syndrome, myasthenia gravis, inflammation of the nervous system, SLE (systemic lupus erythematosus), rheumatoid arthritis, vasculitis, polyarteritis nodosa, Sjogren syndrome, mixed connective tissue disease, glomerulonephritis, thyroid autoimmune disease, Graves' disease, Hashimoto's thyroiditis, sepsis, meningitis, a bacterial infection, a viral infection, a fungal infection, sarcoidosis, hepatitis, and portal vein hypertension, obesity, constipation, irritable bowel syndrome, pancreatitis, type I diabetes, anemia, and type II diabetes, and to increase the glomerular filtration rate (GFR) in patients such as those suffering from kidney failure.

Such vagal stimulation is also beneficial for treating some conditions or under some circumstances in which heart rate reduction is not indicated or is contraindicated. For example, such vagal stimulation is typically appropriate:
- for treating heart failure patients that suffer from bradycardia when taking beta-blockers;
- at nighttime, when heart rate is naturally lower;
- during exercise, such as when the heart rate is already within a desired range and further decreases may reduce exercise tolerance;
- for patients receiving heart-rate lowering drugs, who have achieved a heart rate within a desired range prior to beginning vagal stimulation, and therefore would not benefit from further heart rate reduction;
- for patients suffering from low cardiac output, for whom heart rate reduction may further reduce cardiac output;
- during acute myocardial infarction with cardiogenic shock;
- for patients who experience discomfort or a reduction in exercise capacity when the heart rate is reduced; and
- for patients having a tendency towards bradycardia when receiving vagal stimulation.

In an embodiment, such inversely-proportional stimulation is applied in respective bursts of pulses in each of a plurality of cardiac cycles of the subject, and synchronized with the cardiac cycle of the subject. For some applications, the stimulation is configured to minimize the heart-rate-lowering effects of the stimulation, for example by applying such synchronized stimulation using one or more of the following parameters:
- Timing of the stimulation: delivery of the burst of pulses begins after a variable delay following each P-wave, the length of the delay equal to between about two-thirds and about 90% of the length of the patient's cardiac cycle. Such a delay is typically calculated on a real-time basis by continuously measuring the length of the patient's cardiac cycle.
- Pulse duration: each pulse typically has a duration of between about 200 microseconds and about 2.5 milliseconds for some applications, or, for other applications, between about 2.5 milliseconds and about 5 milliseconds.
- Pulse amplitude: the pulses are typically applied with an amplitude of between about 0.5 and about 5 milliamps, e.g., about 1 milliamp.
- Pulse repetition interval: the pulses within the burst of pulses typically have a pulse repetition interval (the time from the initiation of a pulse to the initiation of the following pulse) of between about 2 and about 10 milliseconds, e.g., about 2.5 milliseconds.
- Pulse period: the burst of pulses typically has a total duration of between about 0.2 and about 40 milliseconds, e.g., about 1 millisecond.
- Pulses per trigger (PPT): the burst of pulses typically contains between about 1 and about 10 pulses, e.g., about 2 pulses.
- Vagus nerve: the left vagus nerve is typically stimulated in order to minimize the heart-rate-lowering effects of vagal stimulation.
- Duty cycle: stimulation is typically applied only once every several heartbeats, or once per heartbeat, when a stronger effect is desired.
- On/off status: for some applications, stimulation is always "on", i.e., constantly applied (in which case, parameters closer to the lower ends of the ranges above are typically used). For other applications, on/off cycles vary between a few seconds to several dozens of seconds, e.g., "on" for about 36 seconds, "off" for about 120 seconds, "on" for about 3 seconds, "off" for about 9 seconds.

For some applications, one or more of these minimal heart-rate-lowering parameters are used for stimulation in other embodiments of the present invention.

In an embodiment of the present invention, control unit 20 comprises or is coupled to an implanted device 25 for monitoring and correcting the heart rate, such as an implantable cardioverter defibrillator (ICD) or a pacemaker (e.g., a bi-ventricular or standard pacemaker). For example, implanted device 25 may be incorporated into a control loop executed by control unit 20, in order to increase the heart rate when the heart rate for any reason is too low.

In an embodiment, at least one of control unit 20 and/or a control unit of the ICD or pacemaker is configured to coordinate an aspect of its operation with an aspect of operation of the other control unit. For example, the aspect of the operation may be an aspect of timing of the operation. Typically, control unit 20 and the control unit of the ICD or pacemaker are not under common control, i.e., an additional controller is not provided for coordinating the aspect of operation. For some applications, control unit 20 or the control unit of the ICD is configured to coordinate the aspect of operation without communicating with the other control unit. Alternatively, for some applications, the control units directly communicate with each other in order to coordinate the aspect of operation. For some applications, control unit 20 is configured to apply vagal stimulation with stimulation and/or feedback parameters that reduce the likelihood of the vagal stimulation causing the ICD or pacemaker to falsely detect arrhythmia. Alternatively or additionally, for some applications, control unit 20 is configured to apply vagal stimulation with stimulation and/or feedback parameters that reduce the likelihood of the occurrence of a "tug-of-war" between vagal stimulation system 18 and the ICD or pacemaker.

According to a first technique for reducing the likelihood of false detection of arrhythmia and/or a tug-of-war with the ICD or pacemaker, control unit 20 is configured to apply vagal stimulation in bursts that are synchronized with the cardiac cycle of the subject. The control unit applies each burst during the refractory period of the heart and the ICD blanking period (the period during which the ICD does not attempt to detect the next heart beat), i.e., typically beginning shortly after detection of each QRS complex (e.g., within between 0 and about 100 milliseconds after detection), as detected by the ICD or the pacemaker, or by stimulation system 18. The control unit typically completes application of each burst within about 100 milliseconds of the detection of the QRS complex. For some applications, the control unit determines the occurrence of the QRS complex based on the detection of the P-wave immediately preceding the QRS complex.

According to a second technique for reducing the likelihood of false detection of arrhythmia and/or a tug-of-war with the ICD, the ICD is configured to generate a communication signal during application of stimulation to the heart. Control unit 20 is configured to receive the signal, and, responsive thereto, to withhold applying vagal stimulation until the ICD completes its application of stimulation. For some applications, control unit 20 waits a certain period of time after the ICD completes stimulation, before again applying vagal stimulation.

According to a third technique for reducing the likelihood of false detection of arrhythmia and/or a tug-of-war with ICD, the ICD is configured to generate a communication signal upon detection of ventricular fibrillation (VF) or ventricular tachycardia (VT). Control unit 20 is configured to receive the signal, and, responsive thereto, to withhold applying vagal stimulation until the ICD indicates that the VF or VT has resolved. Alternatively or additionally, control unit 20 is configured to directly detect the VF, VT, and/or SVT.

According to a fourth technique for reducing the likelihood of false detection of arrhythmia and/or a tug-of-war with the ICD, stimulation system 18 and the ICD are each assigned a discrete range of heart rates at which to apply their respective stimulations. For example, the ICD may be configured to defibrillate, attempt rapid pacing, or pace only at heart rates greater than about 190 BPM or less than about 60 BPM, while control unit 20 is configured to apply vagal stimulation only when the heart rate is between about 70 and about 180 BPM.

According to a fifth technique for reducing the likelihood of false detection of arrhythmia and/or a tug-of-war with the ICD, the ICD is configured to identify the stimulus artifact of the vagal stimulation, and to treat this artifact as noise.

According to a sixth technique for reducing the likelihood of false detection of arrhythmia and/or a tug-of-war with the ICD, stimulation system 18 is configured to have a maximum allowable number of PPT (e.g., 2), which typically results in a stimulation period that is too brief for the ICD to detect.

According to a seventh technique for reducing the likelihood of false detection of arrhythmia and/or a tug-of-war with the ICD, the ICD is configured to generate a communication signal at every R-wave detection. Control unit 20 is configured to receive the signal, thereby avoiding any potential discrepancy between control unit 20 and the ICD regarding the precise timing of each R-wave. Such synchronization also enables determination of a common reference time point in each cardiac cycle. For example, the ICD may be configured to use this common reference point as the starting time for a blanking period, as described in the ninth technique hereinbelow.

According to an eighth technique for reducing the likelihood of false detection of arrhythmia and/or a tug-of-war with the ICD, control unit 20 is configured to generate a communication signal to the ICD during each application of vagal stimulation. The ICD receives the signal, and, responsively thereto, withholds applying stimulation while the control unit is applying vagal stimulation.

According to a ninth technique for reducing the likelihood of false detection of arrhythmia and/or a tug-of-war with the ICD, the ICD is configured to have an extended blanking period, during which the ICD does not attempt to detect the next heart beat. Control unit 20 is configured to apply vagal stimulation only during this extended blanking period. Because the ICD does not sense during this period, the ICD cannot falsely identify the vagal stimulation as a feature of the cardiac cycle, such as an R-wave.

According to a tenth technique for reducing the likelihood of false detection of arrhythmia and/or a tug-of-war with the ICD: (a) the ICD is configured to detect an occurrence of arrhythmia only if the arrhythmia continues for a certain number (X) of consecutive heart beats, and (b) control unit 20 is configured to not stimulate during more than a certain number (Y) of consecutive heart beats, where Y is less than X.

According to an eleventh technique for reducing the likelihood of false detection of arrhythmia and/or a tug-of-war with the ICD, control unit 20 and/or the ICD is programmed with a flag, which indicates to the device that it must take into consideration the presence of the other device. If the flag indicates that no other device is present, techniques for avoiding conflicts between the devices do not need to be employed. Control unit 20 and the ICD typically communicate with one another in order to set the flag.

For some applications, two or more of these techniques for reducing the likelihood of false detection of arrhythmia and/or a tug-of-war with the ICD are used in combination.

In an embodiment, upon detection of suspected arrhythmia, either by the ICD or by stimulation system 18, control unit 20 applies vagal stimulation in order to reduce the ventricular rate. The ICD is configured to apply defibrillation to the heart if the vagal stimulation is not sufficiently effective in reducing the ventricular rate.

In an embodiment of the present invention, control unit 20 is configured to classify an arrhythmia detected by the ICD or system 18. Ventricular tachycardia (VT) and ventricular fibrillation (VF) originate in the ventricles. Because vagal stimulation affects the SA and AV nodes, vagal stimulation does not have a meaningful effect on heart rate during VT or VF. To classify a detected arrhythmia, control unit 20 applies vagal stimulation, and determines its effect on heart rate and/or heart rate variability. If the vagal stimulation affects heart rate or variability, control unit 20 makes a determination that the arrhythmia probably did not originate in the ventricles, and therefore is probably neither VT nor VF.

In an embodiment of the present invention, control unit 20 implements one or more counters, either in software running the control unit, or in hardware. Such counters include, but are not limited to:
- a counter that counts the number of stimulations, e.g., the number of bursts, applied to the vagus nerve during a certain period of time;
- a counter that counts the total number of pulses applied to the vagus nerve during a certain period of time. For example, if control unit 20 applies 2 bursts each having 3 PPT, the counter counts 6 pulses; and/or
- a counter that counts the number of detected heart beats during a certain period of time.

For some applications, such as when control unit 20 operates using feedback, as described hereinabove, an average number of pulses per stimulation burst (i.e., average PPT) is calculated by dividing the total number of pulses applied in a given period by the number of stimulation bursts applied in the period. This calculation is typically performed by control unit 20, or by a physician using the data generated by the counters. The average PPT is an indication of the strength of stimulation the control unit needed to apply, based on feedback, in order to maintain the heart rate at the desired target rate. A physician may use this indication to adjust parameters of the stimulation. For example, if the physician believes the average PPT is too high, he may increase the strength of the stimulation by adjusting another parameter, such as the amplitude of the applied signal, which should result in a lower average PPT. Alternatively, the physician may adjust the target heart rate in order to cause a lower average PPT.

For some applications, control unit 20 monitors in real time the average PPT. For example, a sudden increase in average PPT (calculated over an appropriate time period) may be interpreted as a possible technical failure or change in the physiological state of the subject (e.g., decompensation of the underlying disease). It is to be appreciated that tasks described herein as being performed by a physician may also be performed by a suitably-configured algorithm.

In an embodiment of the present invention, control unit 20 operates using feedback, as described hereinabove, and is configured to target a number of pulses applied during each burst of stimulation, responsive to the feedback. Such feedback sometimes results in variations in the average number of pulses per burst. In this embodiment, control unit 20 is configured to monitor the average number of pulses per burst in a given time period. Such monitoring is performed either periodically or substantially continuously. If the average number of pulses per burst exceeds a maximum threshold value over the given time period, the control unit modifies one or more stimulation or feedback parameters, such that the average number of pulses per burst declines below the maximum threshold value. For example, the maximum threshold value may be between about 2 and about 4 pulses per burst, e.g., about 3 pulses per burst. Appropriate parameters for modification include, but are not limited to, (a) one or more of the feedback parameters, such as the target heart rate (e.g., TargetRR), and/or the feedback integral coefficient, and/or (b) one or more stimulation parameters, such as stimulation amplitude, and pulse width, and/or maximum number of pulses within a burst. Alternatively or additionally, for some applications, if the average falls below a minimum threshold value, the control unit modifies one or more stimulation or feedback parameters, such that the average number of pulses per burst increases above the minimum threshold value.

In an embodiment of the present invention, control unit 20 operates using feedback, as described hereinabove, which results in a variable number of bursts per heart beat and/or per unit time. (For example, a burst may be applied every 1-60 heart beats, or every 0.3-60 seconds, as dictated by a feedback algorithm.) Such feedback sometimes results in high- and/or low-frequency variations in the duty cycle. Control unit 20 is configured to monitor the average duty cycle in a given time period. Such monitoring is performed either periodically or substantially continuously. If the average exceeds a maximum threshold value, the control unit modifies one or more stimulation or feedback parameters, such that the average duty cycle declines below the maximum threshold value. Appropriate parameters for modification include, but are not limited to, the target heart rate (e.g., TargetRR), the feedback integral coefficient, stimulation amplitude, pulse width, and maximum number of pulses within a burst. Alternatively or additionally, for some applications, if the average falls below a minimum threshold value, the control unit modifies one or more stimulation or feedback parameters, such that the average duty cycle increases above the maximum threshold value. For some applications, control unit 20 implements the techniques of this embodiment in combination with the techniques for monitoring the average number of pulses per burst described above.

In an embodiment of the present invention, in which control unit 20 is configured to operate in intermittent "on"/"off" periods, as described hereinabove, the monitored average duty cycle is used in combination with the ratio of the "on" duration to "off" duration in order to determine the magnitude of the heart-rate-lowering effect of the vagal stimulation. A duty cycle less than the "on"/"off" ratio indicates that the stimulation is causing lowering of the heart rate, while a duty cycle equal to the "on"/"off" ratio indicates that no such lowering of the heart rate is occurring. Typically, control unit 20 monitors the average duty cycle over a time period that includes at least one full "on" period and one full "off" period, such as several "on" and "off" periods. For example, assume that control unit 20 is configured to stimulate in alternating "on" periods of 60 seconds and "off" periods of 120 seconds. During the "on" periods the average heart rate is 60 BPM, and during the "off" periods the average heart rate is 120 BPM. Using these exemplary values, the duty cycle would be 60 bursts/300 heart beats=0.2, and the "on"/"off" ratio would be 60 seconds/180 seconds=0.33. The duty cycle is less than the "on"/"off" ratio, indicating that the stimulation is effectively lowering the heart rate. If, on the other hand, the heart rate remained 120 BPM during the "on" periods, the duty cycle would be 120 bursts/360 heart beats=0.33, while the "on"/"off" ratio would remain 0.33. This equality would indicate that the stimulation is having no heart-rate-lowering effect.

In an embodiment of the present invention, control unit 20 operates using feedback, as described hereinabove, and is configured to set a maximum allowable level of stimulation. Control unit 20 does not apply stimulation beyond this maximum level even if the feedback algorithm calls for increased stimulation. Typically, the maximum allowable level of stimulation is expressed as an average amount of energy over a time period of at least about 1 minute, e.g., about 30 minutes. A physician typically sets the maximum level based on considerations such as possible side effects of stimulation, safety, and physiological tolerance. Alternatively or additionally, the maximum level is preconfigured based on generally-applicable safety considerations. The maximum level of stimulation is typically implemented by setting a maximum level (typically predetermined) of one or more of the following parameters:

Maximum PPT, e.g., between about 2 and about 20, such as about 8.

Maximum duty cycle, e.g., between about 5% and about 100%, e.g., 20%, in a time frame of between about 5 seconds and several weeks, e.g., one day.

Maximum continuous stimulation period, expressed in either heart beats or units of time.

Peak power consumption, e.g., about 1 watt.

A physician may increase one or more of these values (e.g., maximum PPT), for example, if a subject adapts to stimulation, or decrease one or more of these values (e.g., maximum PPT) if side effects occur. In the event that feedback causes the value of one or more of these parameters to exceed the maximum value (e.g., the duty cycle to exceed a threshold value such as 50%, or the continuous stimulation period exceeds a threshold value such as 5 hours), control unit 20 automatically, or a physician manually, may, for example, increase the target heart rate, or apply fast intermittent stimulation (as defined hereinabove), in order to reduce the value of the parameter to an appropriate level below the maximum value. Alternatively or additionally, when feedback causes the value of one or more of these parameters to exceed the maximum, control unit 20 may notify the subject and/or the physician, so that the subject may seek medical care, and/or the physician may adjust one or more of the stimulation parameters.

In an embodiment of the present invention, control unit 20 is configured to gradually ramp the commencement and/or termination of stimulation. In order to achieve the gradual ramp, the control unit is typically configured to gradually modify one or more stimulation parameters, such as those described hereinabove, e.g., pulse amplitude, number of pulses, PPT, pulse frequency, pulse width, "on" time, and/or "off" time. Terminating stimulation gradually, rather than suddenly, may reduce the likelihood of a rebound acceleration of heart rate that sometimes occurs upon termination of vagal stimulation. As appropriate, one or more of these parameters is varied by less than 50% of the pre-termination value per heart beat, or less than 5% per heart beat, in order to achieve the gradual ramp.

In an embodiment of the present invention, control unit 20 is configured to gradually increase the strength of stimulation according to a predetermined schedule. Such a gradual increase is typically appropriate during the first several days of use of system 18 by a new subject. Subjects sometimes experience discomfort and/or pain during their initial exposure to stimulation. Such discomfort and/or pain typically ceases after an accommodation period of several days. By gradually increasing stimulation from an initially low level, control unit 20 generally prevents such discomfort and/or pain. For example, the strength of stimulation may be increased less than 50% per hour, or less than 10% per day. The control unit is typically configured to increase the strength of stimulation by adjusting one or more stimulation parameters, such as those described hereinabove, e.g., the amplitude of the applied signal.

For some applications, system 18 is configured to allow the subject to manually control the ramp-up of stimulation, e.g., by selecting when the system proceeds to successive levels of stimulation, and/or by requesting the system to return to a previous level of stimulation.

In an embodiment, these techniques for gradually increasing the strength of stimulation are applied to stimulation of nerves other than the vagus nerve, such as other nerve stimulation is known in the art.

In an embodiment of the present invention, control unit 20 is configured to store a series of one or more physiological parameters measured by system 18, in response to receiving an external command to store the parameters. This allows a physician to specify precisely when to begin recording the series, which enables the physician to monitor acute changes in the subject. For example, in order to test external and/or stimulation effects on heart rate, the physician may begin recording the series prior to: (a) instructing the subject to change his position, (b) applying carotid massage to the subject, (c) adjusting stimulation and/or feedback parameters, and/or (d) applying stimulation to the subject using stimulation parameters the physician would like to evaluate. For some applications, the recorded physiological parameters include (a) R-R intervals, as described hereinabove, (b) systolic and diastolic blood pressures, and/or (c) at least one feature of an electrocardiogram (ECG). For some applications, control unit 20 is configured to store the physiological parameters over a predefined period of time, or for a predetermined number of values of the parameters. In an embodiment, control unit 20 is configured to accept an external command to begin recording the series of parameters at a time in the future, e.g., at a certain time of day, or after a certain delay.

In an embodiment of the present invention, a subject's reaction to stimulation using stimulation system 18 is evaluated while the subject exercises. The subject typically performs the exercise using exercise equipment, such as a treadmill. For some applications, a physician initially sets stimulation parameters of system 18 while the subject is at rest with a relatively low heart rate. The subject then performs the exercise, which increases the heart rate to a level the physician considers to be at least the maximum level the subject is likely to experience during normal daily activity. Using feedback, as described hereinabove, control unit 20 reacts to the increased heart rate by modifying one or more stimulation parameters to increase the level of stimulation. This increased level of stimulation represents the maximum stimulation likely to be applied to the subject during use of system 18. Therefore, such stimulation is likely to produce the maximum potential side effects of stimulation that the subject may experience. The physician evaluates the subject at this increased level of stimulation in order to assess these side effects and the tolerance of the subject to stimulation by system 18. Based on this evaluation, the physician may modify the stimulation parameters, or make other decisions regarding the subject's treatment.

Alternatively or additionally, stimulation parameters are adjusted during the exercise in order to achieve the heart rate at which the heart is maximally effective. Such effectiveness may be measured, for example, by peak performance, peak $pO_2$, or other indicators of heart effectiveness known in the art.

In an embodiment of the present invention, for applications in which control unit 20 is configured to apply vagal stimulation intermittently, as described hereinabove, the control unit begins the stimulation with an "off" period, rather than with an "on" period. As a result, a delay having the duration of an "off" period occurs prior to beginning stimulation. Alternatively or additionally, whether or not configured to apply stimulation intermittently, control unit 20 is configured to delay beginning the application of stimulation for a certain time period (e.g., a pseudo-randomly determined time period, or a predetermined fixed period of time, such as about 5 seconds) after receiving an external command to apply the stimulation. The use of these delaying techniques generally reduces a subject's anticipation of any pain or discomfort that he may associate with stimulation, and disassociates the sensations of stimulation from the physician and/or an external control device such as a wand.

In an embodiment of the present invention, a method for facilitating the determination of vagal stimulation parameters comprises: (a) applying intermittent vagal stimulation, as described hereinabove, during a calibration period of time that includes a plurality of different naturally-occurring heart rates; (b) for each "on" period and each "off" period, calculating an average heart rate during the period; and (c) segmenting the average heart rates during the "off" periods into a plurality of heart rate ranges; and (d) separately evaluating the effect of vagal stimulation on heart rates within each heart rate range, by calculating an average difference in average heart rate between "on" and "off" periods within the given heart rate range. This analysis is used to determine separate stimulation and feedback parameters for each range of heart rates.

Figure 6:
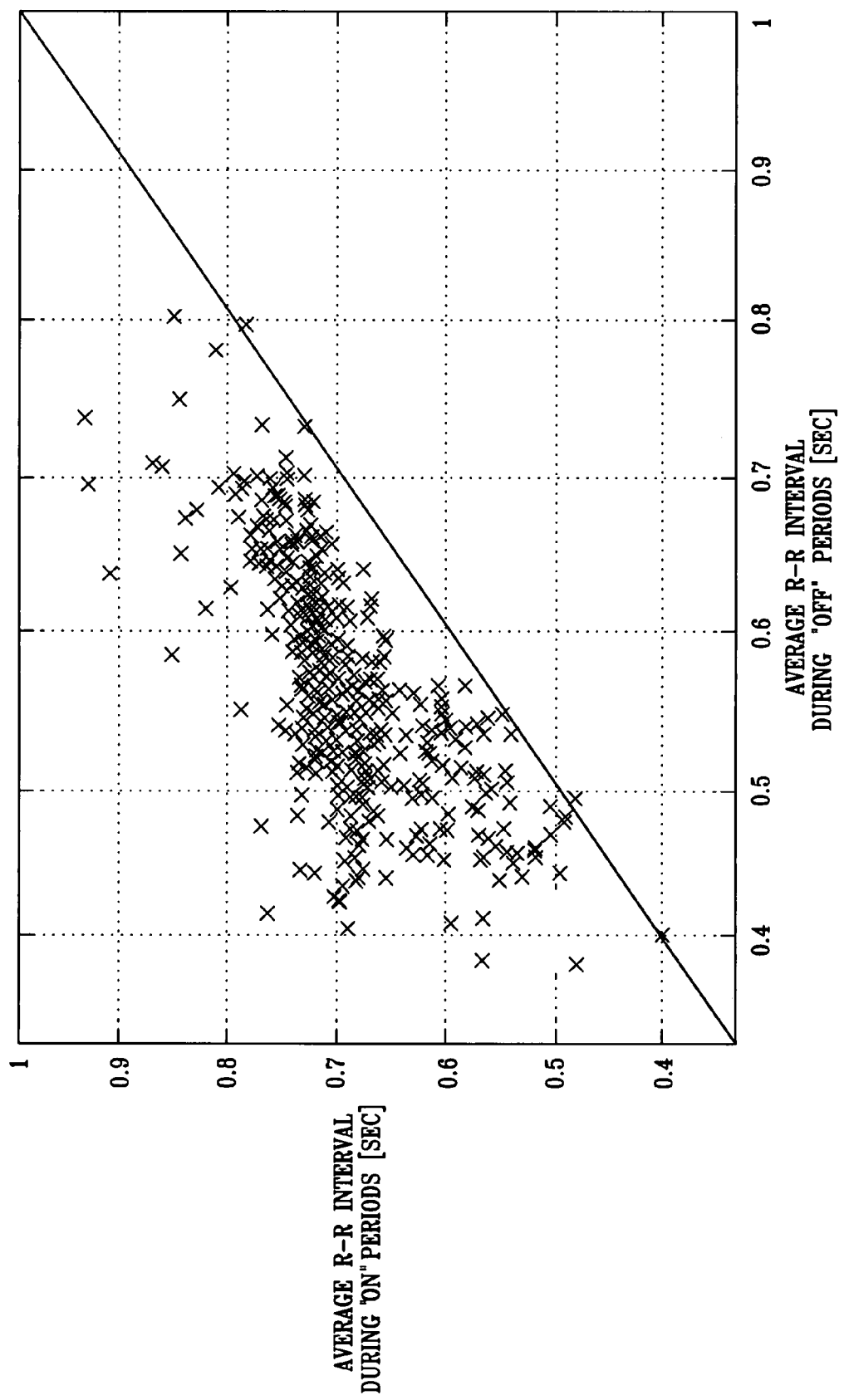

FIG. 6 is a graph illustrating experimental results measured in accordance with an embodiment of the present invention. Intermittent vagal stimulation was applied to a conscious dog during alternating "on" and "off" periods having durations of 1 minute and 2 minutes, respectively. Each point on the graph (indicated by an "x") represents a single stimulation period, including a single "on" period and the "off" periods immediately preceding and following the "on" period. The y-coordinate of each point indicates the average R-R interval during the respective "on" period, and the x-coordinate indicates the average R-R interval during the respective "off" periods immediately preceding and following the "on" period. As can be seen in the graph, nearly all of the points lie above the x=y line, indicating that the vagal stimulation lowered the heart rate during the stimulation "on" periods more than non-stimulation lowered the heart rate during the corresponding non-stimulation "off" periods. The graph of FIG. 6 thus presents an overall view of the reaction of the dog to vagal stimulation. In an embodiment of the present invention, a graph such as that shown in FIG. 6 is generated in order to enable (a) visualization and/or assessment of the effectiveness of vagal stimulation at various heart rates, and, optionally, (b) modification of applied signal parameters to improve the response at certain heart rates.

In an embodiment of the present invention, in which control unit 20 (FIG. 1) is implantable, vagal stimulation system 18 further comprises an external monitoring unit (not shown in figures). For some applications, the monitoring unit is adapted to record the timing of the application of vagal stimulation, such as the timing of the commencement and/or termination of "on" and "off" periods. Typically, the monitoring unit performs this recording in real-time while system 18 applies the vagal stimulation. (In some hardware configurations, it is not feasible to record such data in implantable control unit 20 because the control unit lacks sufficient memory.)

For some applications, in order to perform the recording, the monitoring unit monitors an electrocardiogram (ECG) of the subject, and detects an artifact in the ECG that is indicative of application of the stimulation signal. For some applications, one or more ECG monitoring patches are placed on the surface of the skin in a vicinity of electrode device 26. For stimulation that is synchronized with a feature of the subject's cardiac cycle (e.g., with an R-wave), the monitoring unit typically attempts to detect the stimulation artifact only at the known appropriate delay from the feature of the cardiac cycle, so as to reduce the likelihood of a false positive detection of stimulation. Alternatively, a dedicated recording channel of the ECG is assigned to record the electrical potential differences between the two sides of the neck, which detects substantially only the stimulation artifact, rather than the ordinary ECG signal.

Alternatively, in order to facilitate the recording, implantable control unit 20 is adapted to transmit a communication signal to the external monitoring unit upon each application of vagal stimulation. Typically, control unit 20 sends the communication signal wirelessly; alternatively, the signal is sent over wires to the monitoring unit.

For some applications, the intermittent vagal stimulation is applied with "on" periods having a duration of between about 45 and about 75 seconds each, e.g., about 1 minute each, and "off" periods having a duration of between about 90 and about 150 seconds each, e.g., about 2 minutes each. Alternatively or additionally, the intermittent vagal stimulation is applied with "off" periods having a duration of between about 1.2 and about 3.5 times greater than the "on" periods, e.g., between about 1.5 and about 2.5 times greater than the "on" periods. In order to include the plurality of different naturally-occurring heart rates, the calibration period typically includes at least several hundred "on" and "off" periods. For example, the calibration period may be about 24 hours. Alternatively, the calibration period is shorter, and includes sub-periods of rest, exercise, and recovery from exercise, in order to ensure the inclusion of the plurality of different naturally-occurring heart rates. For example, for at least part of the calibration period the subject may be subjected to an exercise test (e.g., a stress test), such as by using exercise equipment, e.g., a treadmill.

In an embodiment of the present invention, control unit 20 comprises or is coupled to an implanted device 25, such as an ICD, that is configured to apply antitachycardia pacing in order to treat ventricular tachycardia. Control unit 20 is configured to apply vagal stimulation in conjunction with antitachycardia pacing.

In an embodiment of the present invention, control unit 20 is adapted to (a) receive a sensed physiological parameter of the subject from ECG monitor 24 and/or physiological sensors 28, and (b) responsively to the sensed physiological parameter, configure the applied stimulation to treat bundle branch block of the subject.

Reference is made to FIG. 7, which is a flow chart that schematically illustrates a method for treating life-threatening arrhythmia (LTA), in accordance with an embodiment of the present invention. In this embodiment, control unit 20 comprises or is coupled to implanted device 25, such as an ICD or pacemaker, that is configured to apply anti-arrhythmic therapy, such as rapid pacing, defibrillation, and/or cardioversion. Control unit 20 is adapted to detect the LTA (for example, VF, VT, or fast VT), and evaluate the severity of the LTA. Upon detection, the control unit attempts to resolve the LTA by selecting the optimal therapy for the LTA, responsively to the evaluation. Typically, the control unit is configured to: (a) preferably, drive electrode device 26 to apply parasympathetic stimulation, and (b) less preferably, drive implanted device 25 to apply anti-arrhythmic therapy if such anti-arrhythmic therapy is indicated, e.g., if parasympathetic stimulation has not successfully resolved the LTA, or is deemed unlikely to resolve the LTA. The techniques of this embodiment thus generally reduce the use of anti-arrhythmic therapy, which is often painful or unpleasant for patients.

Turning to the flow chart, at a monitor step 100, control unit 20 monitors heart 30 by receiving one or more sensed parameters, e.g., R-waves, such as detected by ECG monitor 24. At an LTA detection step 102, control unit 20 determines whether an LTA is occurring, such as by using techniques described herein or in one or more articles, patents, and/or patent applications incorporated herein by reference, or otherwise known in the art. If an LTA is not detected, control unit 20 continues monitoring heart 30 at monitor step 100.

If, on the other hand, control unit 20 detects an LTA, at a parasympathetic stimulation step 104 the control unit applies parasympathetic stimulation to subject 31 in an attempt to resolve the LTA without application of anti-arrhythmic therapy. The control unit typically, but not necessarily, applies the parasympathetic stimulation using vagal stimulation techniques described herein or in one or more articles, patents, and/or patent applications incorporated herein by reference, or otherwise known in the art.

The control unit determines whether the LTA has been resolved, at an LTA resolution check step 106. If the LTA has been resolved, the control unit returns to monitor step 100. Otherwise, at an evaluation check step 108, the control unit determines whether anti-arrhythmic therapy is indicated, e.g., that parasympathetic stimulation is unlikely to resolve the LTA. To make this determination, the control unit typically considers such factors as the severity of the LTA, trends in the severity of the LTA, the time from the onset of the LTA, and the duration of the parasympathetic stimulation. For example, if the time from the onset of the LTA exceeds a certain threshold value, the control unit may determine that anti-arrhythmic therapy is indicated. (For some applications, the control unit modifies, e.g., reduces, the threshold value on subsequent iterations through step 106.) Alternatively, the control unit may, for example, determine that continued parasympathetic stimulation is indicated if the heart rate is less than an upper threshold indicative of continuing LTA, but greater than a lower threshold indicative of resolution of all arrhythmia (e.g., the upper threshold may be about 200 BMP, and the lower threshold may be about 160 BMP). If the control unit determines that anti-arrhythmic therapy is indicated, the control unit applies anti-arrhythmic therapy at an anti-arrhythmic therapy step 110. On the other hand, if the control unit determines that anti-arrhythmic therapy is not indicated, the control unit continues applying parasympathetic stimulation at step 104. For some applications, the control unit modifies at least one parameter of such parasympathetic stimulation during some or all of the repetitions of step 104.

Reference is made to FIG. 8, which is a flow chart that schematically illustrates another method for treating life-threatening arrhythmia (LTA), in accordance with an embodiment of the present invention. This method is similar to the method described hereinabove with reference to FIG. 7, except that according to this method control unit 20 applies chronic parasympathetic stimulation even in the absence of an LTA. At a parasympathetic stimulation and monitor step 120, the control unit applies the chronic parasympathetic stimulation and monitors heart 30. The control unit determines whether an LTA is occurring, at an LTA detection step 122. If an LTA is not detected, control unit 20 continues monitoring heart 30 at parasympathetic stimulation and monitor step 120.

If, on the other hand, control unit 20 detects an LTA, the control unit modifies at least one parameter of the parasympathetic stimulation (for example, in order to modify, e.g., increase, a strength of the stimulation), at a modify parameter step 124. The control unit continues to apply the parasympathetic stimulation, using the new parameter, at a parasympathetic stimulation step 126. At an LTA resolution check step 128, the control unit determines whether the LTA has been resolved. If the LTA has been resolved, the control unit returns to parasympathetic stimulation and monitor step 120. Otherwise, at an evaluation check step 130, the control unit determines whether anti-arrhythmic therapy is indicated, such as by using one or more of the techniques described hereinabove with reference to evaluation check step 108 of FIG. 7. If the control unit determines that anti-arrhythmic therapy is indicated, the control unit applies anti-arrhythmic therapy at an anti-arrhythmic therapy step 132. On the other hand, if the control unit determines that anti-arrhythmic therapy is not indicated, the control unit returns to step 124, at which the control unit again modifies at least one parameter of the parasympathetic stimulation. (Alternatively, for some applications, the control unit determines that no parameters need to be modified, and therefore skips step 124 and proceeds to step 126.)

Some embodiments of the present invention combine vagal stimulation with other methods of electric therapy for the heart. Among these other methods are pacing, anti-arrhythmia pacing, defibrillation and cardiac resynchronization therapy (CRT).

CRT is typically indicated for patients with intrinsic conduction abnormalities, specifically with bundle branch blocks or delays. One type of CRT apparatus comprises a control unit and an electric stimulator connected to an atrial sensing lead and two ventricular pacing leads, one for each ventricle. The pacing lead for the left ventricle is usually placed over the left ventricle through the coronary sinus, while the right ventricle lead is placed within the right ventricle. The control unit senses an atrial depolarization and applies timed pacing signals to both ventricles. Typically the pacing signal to the right ventricle is applied around 110 ms after atrial depolarization, and the pacing signal to the left ventricle follows within about 50 ms.

At the time of implantation of a CRT device, echocardiographic measurements are typically used to find suitable timing settings to provide improved cardiac performance. The timing settings typically vary as a function of heart rate, and the beneficial effect of CRT also typically varies as a function of heart rate.

It has been observed with respect to CRT that the pacing frequency should be faster than the normal heart rate (otherwise the natural rhythm or the natural conduction may prevail). Thus CRT is typically limited to patients in whom the conduction times and/or heart rate are slow.

It has also been observed with respect to CRT that the applied pacing signal does not always propagate through natural conduction pathways.

Some embodiments of the present invention provide a combination of (a) biventricular pacing with (b) sensing in any one or more of the four chambers, to facilitate control of the timing of induced contractions. In the context of the present patent application and in the claims, this is also referred to as cardiac resynchronization therapy.

Vagal stimulation has been shown to reduce sinus rate, prolong conduction through the AV node, and alter conductance of other pathways within the heart.

In some embodiments of the present invention, CRT and vagal stimulation are both applied to a patient as part of a treatment protocol. Typically, the vagal stimulation is applied using techniques described hereinabove, and the CRT and vagal stimulation achieve a synergistic effect. For some applications, the CRT improves an effect of the vagal stimulation. Alternatively or additionally, the vagal stimulation improves an effect of the CRT. For some applications, use of vagal stimulation allows CRT to be applied to a patient otherwise not eligible or suitable for CRT. For some applications, use of CRT allows vagal stimulation to be applied to a patient otherwise not eligible or suitable for vagal stimulation. In an embodiment, one or more of the benefits described in this paragraph are facilitated by at least one of the following:

Vagal stimulation is configured to prolong AV conduction time, in combination with CRT.

Vagal stimulation is configured to prolong RR interval, in combination with CRT.

Vagal stimulation and CRT are applied using separate devices not under common control.

Vagal stimulation and CRT are each configured to improve cardiac performance.

In some embodiments, CRT is applied in order to modify an effect of vagal stimulation. Vagal stimulation may cause transient conduction delays, especially AV conduction delays, even in patients with no "natural" conduction disturbances. Applying CRT together with vagal stimulation typically reduces this effect of vagal stimulation, thus improving the outcome of the patient.

In some configurations, vagal stimulation reduces atrial contraction force, thus changing the filling curve of the ventricles. In such a case, the optimal timing of ventricular contraction is typically different from the optimal timing without vagal stimulation. By using CRT, different AV timings can be set for periods with vagal stimulation compared to periods without such stimulation. This typically improves cardiac performance during vagal stimulation.

In some embodiments, vagal stimulation is used to improve CRT. Vagal stimulation may be used, for example, to slow conduction times, thus allowing resynchronization therapy in patients with shorter than optimal-for-CRT AV delays and/or with shorter than optimal-for-CRT intracardiac conduction times.

In some embodiments, in patients in whom a portion of the cardiac conduction is too fast and other portions are too slow, vagal stimulation is used to prolong the conduction time of some or all pathways, facilitating improvement of cardiac performance by CRT.

For some applications, vagal stimulation brings the heart rate to a heart rate at which the benefit of CRT is improved, thus enhancing the efficacy of CRT.

In some embodiments, vagal stimulation, by itself, is used as resynchronization therapy. In this context, vagal stimulation may be used as a sole therapy to optimize AV conduction time, and to bring about synchronization of cardiac contraction by the differential effect of vagal stimulation on each ventricle. The intensity and timing of vagal stimulation together with the specific site of stimulation can affect both the atrial-ventricle and the ventricle-ventricle conduction time intervals and reduce the overall heart rate, resulting in improved cardiac performance.

In some embodiments, a CRT device receives a communication signal from a vagal stimulator and changes its own settings responsively thereto. For instance, the CRT device may provide a longer AV time when vagal stimulation is applied, while providing a shorter AV time when no stimulation is applied. Alternatively or additionally, the CRT device may apply pacing generally only when vagal stimulation is applied, thus reducing pacing that forces conduction that is not through natural pathways. Further alternatively or additionally, the CRT device may set the VV or AV timings as a function of the patient's heart rate, parameters of the vagal stimulator device, or sensor signals from a physiological sensor.

In some embodiments, both the vagal stimulator and the CRT device are assembled in one integrated unit.

In some embodiments, a vagal stimulator changes its stimulation parameters (e.g., timing within cardiac cycle, amplitude, pulse width, or PPT) to achieve desired AV conduction times and/or QRS duration. This vagal stimulator typically comprises a sensor and/or circuitry for measuring and/or evaluating these stimulation parameters. For different patients, or in one patient at different times, the desired conduction times may be the optimal conduction times, thus reducing the use of CRT, or the desired conduction times may be longer than optimal times, allowing the CRT to work efficiently.

In some embodiments of the present invention, vagal stimulation as described herein is applied in combination with multi-chamber pacing (e.g., biventricular pacing, biatrial pacing, or pacing of at least one of the ventricles combined with pacing of at least one of the atria).

Although embodiments of the present invention are described herein, in some cases, with respect to treating specific heart conditions, it is to be understood that the scope of the present invention generally includes utilizing the techniques described herein to controllably stimulate the vagus nerve to facilitate treatments of, for example, heart failure, atrial fibrillation, and ischemic heart diseases. In particular, the techniques described herein may be performed in combination with other techniques, which are well known in the art or which are described in the references cited herein, that stimulate the vagus nerve in order to achieve a desired therapeutic end.

For some applications, techniques described herein are used to apply controlled stimulation to one or more of the following: the lacrimal nerve, the salivary nerve, the vagus nerve, the pelvic splancnic nerve, or one or more sympathetic or parasympathetic autonomic nerves. Such controlled stimulation may be applied to such nerves directly, or indirectly, such as by stimulating an adjacent blood vessel or space. Such controlled stimulation may be used, for example, to regulate or treat a condition of the lung, heart, stomach, pancreas, small intestine, liver, spleen, kidney, bladder, rectum, large intestine, reproductive organs, or adrenal gland.

As appropriate, techniques described herein are practiced in conjunction with methods and apparatus described in one or more of the following patent applications, all of which are assigned to the assignee of the present application and are incorporated herein by reference:

U.S. patent application Ser. No. 10/205,474, filed Jul. 24, 2002, entitled, "Electrode assembly for nerve control," which published as US Patent Publication 2003/0050677

U.S. Provisional Patent Application 60/383,157 to Ayal et al., filed May 23, 2002, entitled, "Inverse recruitment for autonomic nerve systems"

U.S. patent application Ser. No. 10/205,475, filed Jul. 24, 2002, entitled, "Selective nerve fiber stimulation for treating heart conditions," which published as US Patent Publication 2003/0045909

PCT Patent Application PCT/IL02/00068, filed Jan. 23, 2002, entitled, "Treatment of disorders by unidirectional nerve stimulation," and U.S. patent application Ser. No. 10/488,334, filed Feb. 27, 2004, in the US National Phase thereof U.S. patent application Ser. No. 09/944,913, filed Aug. 31, 2001, entitled, "Treatment of disorders by unidirectional nerve stimulation"

U.S. patent application Ser. No. 10/461,696, filed Jun. 13, 2003, entitled, "Vagal stimulation for anti-embolic therapy"

PCT Patent Application PCT/IL03/00430, filed May 23, 2003, entitled, "Electrode assembly for nerve control," which published as PCT Publication WO 03/099373

PCT Patent Application PCT/L03/00431, filed May 23, 2003, entitled, "Selective nerve fiber stimulation for treating heart conditions," which published as PCT Publication WO 03/099377

U.S. patent application Ser. No. 10/719,659, filed Nov. 20, 2003, entitled, "Selective nerve fiber stimulation for treating heart conditions"

A PCT patent application filed May 23, 2004, entitled, "Selective nerve fiber stimulation for treating heart conditions"

A PCT patent application filed Jun. 10, 2004, entitled, "Vagal stimulation for anti-embolic therapy"

A US patent application filed Jun. 10, 2004, entitled, "Applications of vagal stimulation"

A PCT patent application filed Jun. 10, 2004, entitled, "Applications of vagal stimulation"

A US patent application filed Dec. 22, 2004, entitled, "Construction of electrode assembly for nerve control"

"Average," as used herein, including in the claims, is to be understood broadly as including any representative value or central tendency of a set of numbers, including arithmetic and geometric mean, median, mode, midrange, and other similar mathematical techniques known in the art.

It will be appreciated by persons skilled in the art that current application techniques described herein may be appropriate for application to additional nerves or tissues, such as, for example, cardiac tissue. In addition, techniques described herein may be appropriate for implementation in pacemakers and/or ICDs, mutatis mutandis. For example, techniques described herein for configuring and/or regulating the application of an electrical current may be performed, mutatis mutandis, for applying pacing pulses or anti-arrhythmic energy to the heart.

It will also be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
   surgically implanting an electrode device having a cuff and one or more electrodes mounted in the cuff, by placing the electrode device around a nerve such that the electrodes face the nerve;
   introducing conductive solution into the electrode device such that the solution is in contact with both the electrodes and the nerve;
   during implantation of the electrode device, measuring an impedance between one or more of the electrodes and an electrical contact point in electrical communication with the electrode device; and
   responsively to the impedance measurement, determining whether the electrode device is correctly sized for the nerve, and, if not, removing the electrode device and implanting another electrode device having a different size.

2. The method according to claim 1, wherein the conductive solution includes saline solution, and wherein introducing the conductive solution comprises introducing the saline solution.

3. The method according to claim 1, wherein the nerve includes a vagus nerve, and wherein placing the electrode device around the nerve comprises placing the electrode device around the vagus nerve.

4. The method according to claim 1, wherein determining whether the electrode device is correctly sized for the nerve comprises determining whether the electrodes are in good electrical contact with the nerve.

5. The method according to claim 1, wherein determining whether the electrode device is correctly sized for the nerve comprises interpreting a value of the impedance measurement between 100 and 300 ohms as an indication that the electrodes are in poor contact with the nerve.

6. The method according to claim 1, wherein determining whether the electrode device is correctly sized for the nerve comprises interpreting a value of the impedance measurement between 300 and 1000 ohms as an indication that the electrodes are in good contact with the nerve.

7. The method according to claim 1, further comprising determining, responsively to the impedance measurement, whether sufficient conductive solution is in the electrode device, and, if not, introducing additional conductive solution into the electrode device.

8. The method according to claim 7, wherein determining whether sufficient conductive solution is in the electrode device comprises interpreting a value of the impedance measurement greater than 1000 ohms as an indication that insufficient conductive solution is in the electrode device.

9. The method according to claim 1, wherein the one or more electrodes of the electrode device include at least first and second electrodes, wherein the electrical contact point includes the first one of the electrodes, and wherein measuring the impedance comprises measuring the impedance between the first and second electrodes.

10. The method according to claim 1, wherein the electrical contact point is located outside of the electrode device, and wherein measuring the impedance comprises measuring the impedance between the one or more electrodes and the electrical contact point located outside of the electrode device.

* * * * *